(12) United States Patent
Ahn

(10) Patent No.: US 11,807,788 B2
(45) Date of Patent: *Nov. 7, 2023

(54) ORGANIC ELECTROLUMINESCENT COMPOUNDS AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventor: Hee-Choon Ahn, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 0 days.

This patent is subject to a terminal disclaimer.

(21) Appl. No.: 17/558,910

(22) Filed: Dec. 22, 2021

(65) Prior Publication Data

US 2022/0186114 A1 Jun. 16, 2022

Related U.S. Application Data

(63) Continuation of application No. 15/744,884, filed as application No. PCT/KR2016/006853 on Jun. 27, 2016, now abandoned.

(30) Foreign Application Priority Data

Aug. 19, 2015 (KR) .......................... 10-2015-0116621
Oct. 30, 2015 (KR) .......................... 10-2015-0151944
Jun. 21, 2016 (KR) .......................... 10-2016-0077395

(51) Int. Cl.
| | | |
|---|---|---|
| C09K 11/06 | (2006.01) |
| C07D 413/14 | (2006.01) |
| C07D 413/04 | (2006.01) |
| C07D 417/04 | (2006.01) |
| C07D 417/14 | (2006.01) |
| H10K 50/11 | (2023.01) |
| H10K 85/60 | (2023.01) |

(52) U.S. Cl.
CPC ............ *C09K 11/06* (2013.01); *C07D 413/04* (2013.01); *C07D 413/14* (2013.01); *C07D 417/04* (2013.01); *C07D 417/14* (2013.01); *H10K 50/11* (2023.02); *H10K 85/636* (2023.02); *H10K 85/654* (2023.02); *H10K 85/657* (2023.02); *H10K 85/6572* (2023.02); *H10K 85/6576* (2023.02); *C09K 2211/1007* (2013.01); *C09K 2211/1011* (2013.01); *C09K 2211/1033* (2013.01); *C09K 2211/1037* (2013.01); *C09K 2211/1044* (2013.01); *C09K 2211/1059* (2013.01)

(58) Field of Classification Search
CPC . H01L 51/00; H01L 51/0061; H01L 51/0067; H01L 51/0071; H01L 51/0074; H01L 51/0072; C08K 2211/1044; C08K 2211/1059; C08K 2211/1033; C08K 2211/1037; C07D 417/14; C07D 417/04; C07D 413/04; C07D 413/14; H10K 85/636; H10K 85/654; H10K 85/657; H10K 85/6576; H10K 85/6572
See application file for complete search history.

(56) References Cited

U.S. PATENT DOCUMENTS 9,028,979 B2 * 5/2015 Schildknecht ....... C07D 403/14
428/917

FOREIGN PATENT DOCUMENTS

JP 2012176929 A * 9/2012
KR 20140094408 A * 7/2014

OTHER PUBLICATIONS

Machine Translation of JP2012176929 (Year: 2012).*
Machine Translation of KR20140094408 (Year: 2014).*

* cited by examiner

*Primary Examiner* — Andrew K Bohaty
*Assistant Examiner* — Jenna N Chandhok
(74) *Attorney, Agent, or Firm* — G. Creston Campbell

(57) ABSTRACT

The present disclosure relates to organic electroluminescent compounds and an organic electroluminescent device comprising the same. The organic electroluminescent compound according to the present disclosure may be comprised in a light-emitting layer or an electron buffer layer, and is effective to produce an organic electroluminescent device having low driving voltage, excellent current and power efficiencies, and significantly improved operative lifespan.

3 Claims, No Drawings

ORGANIC ELECTROLUMINESCENT COMPOUNDS AND ORGANIC ELECTROLUMINESCENT DEVICE COMPRISING THE SAME

CLAIM OF BENEFIT OF PRIOR APPLICATION

This application claims priority under 35 U.S.C. § 120 from U.S. patent application Ser. No. 15/744,884 filed Jan. 15, 2018, which is the National Stage Entry of PCT/KR2016/006853, filed Jun. 27, 2016, both of which are incorporated by reference herein in their entirety.

TECHNICAL FIELD

The present disclosure relates to organic electroluminescent compounds and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak, by using small aromatic diamine molecules, and aluminum complexes as materials for forming a light-emitting layer [Appl. Phys. Lett. 51, 913, 1987].

An organic EL device (OLED) is a device changing electrical energy to light by applying electricity to an organic electroluminescent material, and generally has a structure comprising an anode, a cathode, and an organic layer between the anode and the cathode. The organic layer of an organic EL device may be comprised of a hole injection layer, a hole transport layer, an electron blocking layer, a light-emitting layer (which comprises host and dopant materials), an electron buffer layer, a hole blocking layer, an electron transport layer, an electron injection layer, etc., and the materials used for the organic layer are categorized by their functions in hole injection material, hole transport material, electron blocking material, light-emitting material, electron buffer material, hole blocking material, electron transport material, electron injection material, etc. In the organic EL device, due to an application of a voltage, holes are injected from the anode to the light-emitting layer, electrons are injected from the cathode to the light-emitting layer, and excitons of high energies are formed by a recombination of the holes and the electrons. By this energy, organic luminescent compounds reach an excited state, and light emission occurs by emitting light from energy due to the excited state of the organic luminescent compounds returning to a ground state.

The most important factor determining luminous efficiency in an organic EL device is light-emitting materials. A light-emitting material must have high quantum efficiency, and high electron and hole mobility, and the formed light-emitting material layer must be uniform and stable. Light-emitting materials are categorized into blue, green, and red light-emitting materials dependent on the color of the light emission, and additionally yellow or orange light-emitting materials. In addition, light-emitting materials can also be categorized into host and dopant materials according to their functions. Recently, the development of an organic EL device providing high efficiency and long lifespan is an urgent issue. In particular, considering EL characteristic requirements for a middle or large-sized panel of OLED, materials showing better characteristics than conventional ones must be urgently developed. The host material, which acts as a solvent in a solid state and transfers energy, needs to have high purity and a molecular weight appropriate for vacuum deposition. Furthermore, the host material needs to have high glass transition temperature and high thermal degradation temperature to achieve thermal stability, high electro-chemical stability to achieve a long lifespan, ease of forming an amorphous thin film, good adhesion to materials of adjacent layers, and non-migration to other layers.

Also, the electron buffer layer can improve the problem that when exposed to a high temperature in the process of the manufacture of panels, the current properties of the device may be changed in the devices, thereby lowering the light-emitting luminance, and thus the properties of compounds comprised in the electron buffer layer are important.

Japanese patent application laid-open No. 2001-23777 discloses an organic electroluminescent device using a phenanthrene compound, in which a 5-membered heteroaryl containing nitrogen is condensed with the middle benzene ring of the phenanthrene backbone, as a host material.

DISCLOSURE OF THE INVENTION

Problems to be Solved

The organic electroluminescent device comprising the compound disclosed in Japanese patent application laid-open No. 2001-23777 shows excellent color purity characteristics of blue, but needs for improving driving voltage, current efficiency, and operative lifespan of the organic electroluminescent device have still remained.

In this regard, the present inventors have found that low driving voltage, excellent efficiency, and a significantly improved operative lifespan of an organic electroluminescent device could be achieved by using a phenanthrene compound, in which a 5-membered heteroaryl is condensed with a side benzene ring of the phenanthrene backbone, as a host or in the electron buffer layer.

The object of the present disclosure is to provide organic electroluminescent compounds being effective to produce an organic electroluminescent device having low driving voltage, excellent current and power efficiencies, and significantly improved operative lifespan.

Solution to Problems

The present inventors found that the above objective can be achieved by an organic electroluminescent compound represented by the following formula 1:

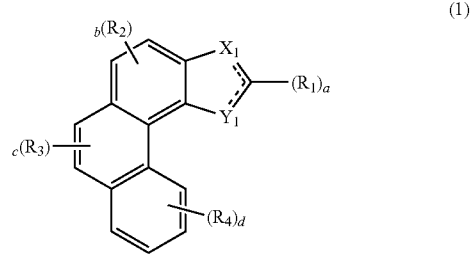

(1)

wherein
$X_1$ represents —N=, —NR$_7$—, —O—, or —S—;
$Y_1$ represents —N=, —NR$_8$—, —O—, or —S—;

with the provisos that when $X_1$ represents —N=, then $Y_1$ represents —$NR_8$—, —O—, or —S—, and when $X_1$ represents —$NR_7$—, then $Y_1$ represents —N=, —O—, or —S—, with the provisos that $X_1$ and $Y_1$ are not simultaneously —O—; $X_1$ and $Y_1$ are not simultaneously —S—; $X_1$ and $Y_1$ are not —O— and —S—, respectively; and $X_1$ and $Y_1$ are not —S— and —O—, respectively;

$R_1$ represents a substituted or unsubstituted (C6-C30)aryl, or a substituted or unsubstituted (3- to 30-membered) heteroaryl;

$R_2$ to $R_4$, $R_7$, and $R_8$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one heteroatom selected from nitrogen, oxygen, and sulfur;

a represents 1; b and c, each independently, represent 1 or 2; d represents an integer of 1 to 4; and the heteroaryl contains at least one heteroatom selected from B, N, O, S, Si, and P.

Effects of the Invention

By using the organic electroluminescent compound of the present disclosure in a light-emitting layer as a host or in an electron buffer layer, efficiency, and lifespan of the organic electroluminescent device are significantly improved compared to the conventional organic electroluminescent compounds. In particular, the organic electroluminescent compound of the present disclosure shows properties more suitable to the current trend of increasing demand for high resolution by maintaining high efficiency at high luminance and having a significantly improved lifespan.

EMBODIMENTS OF THE INVENTION

Hereinafter, the present disclosure will be described in detail. However, the following description is intended to explain the disclosure, and is not meant in any way to restrict the scope of the disclosure.

The present disclosure relates to an organic electroluminescent compound represented by formula 1, an organic electroluminescent material comprising the organic electroluminescent compound, and an organic electroluminescent device comprising the organic electroluminescent compound.

The organic electroluminescent compound of formula 1 may be represented by any one of the following formulae 2 to 4:

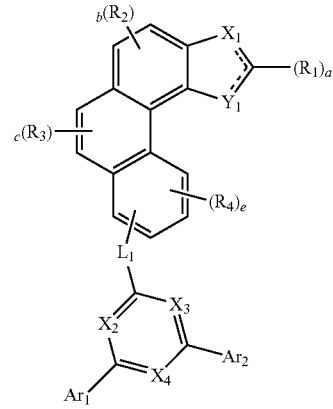

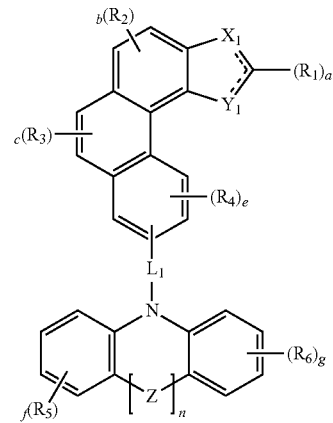

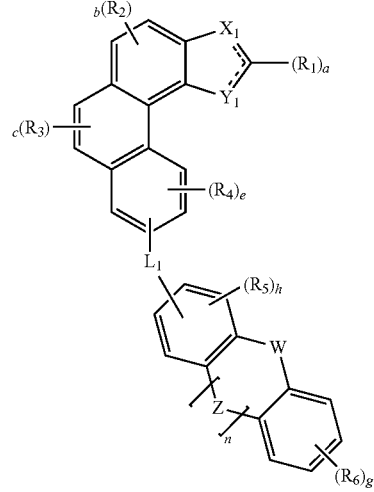

In formulae 1 to 4, $R_1$ represents a substituted or unsubstituted (C6-C30)aryl, or a substituted or unsubstituted (3- to 30-membered)heteroaryl; preferably, a substituted or unsubstituted (C6-C30)aryl, or a substituted (5- to 25-membered) heteroaryl; and more preferably, a substituted or unsubstituted (C6-C30)aryl, or a substituted (5- to 20-membered) heteroaryl. For example, $R_1$ may be an unsubstituted phenyl, an unsubstituted biphenyl, an unsubstituted naphthyl, a fluorenyl substituted with methyl, a benzofluorenyl substituted with methyl, a carbazolyl substituted with phenyl, a benzocarbazolyl substituted with phenyl, an indolocarbazolyl substituted with phenyl, an unsubstituted dibenzofuranyl, an unsubstituted dibenzothiophenyl, a spiro[fluorene-fluorene], or a spiro[fluorene-benzofluorene].

In formulae 1 to 4, $R_2$ to $R_9$, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di- (C6-C30)arylamino, or a substituted or unsubstituted (C1-C30)alkyl(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one heteroatom selected from nitrogen, oxygen, and sulfur; preferably, each independently, hydrogen, a substituted or unsubstituted (C6-C25)aryl, a substituted or unsubstituted (3- to 25-membered) heteroaryl, or a substituted or unsubstituted mono- or di- (C6-C25)arylamino; or are linked to an adjacent substituent (s) to form a substituted or unsubstituted, mono- or polycyclic, (C3-C25) alicyclic or aromatic ring, whose carbon atom(s) may be replaced with at least one heteroatom selected from nitrogen, oxygen, and sulfur; more preferably, each independently, hydrogen, a substituted or unsubstituted (C6-C20)aryl, a substituted or unsubstituted (5- to 25-membered)heteroaryl, or a substituted or unsubstituted di(C6-C18)arylamino; or are linked to an adjacent substituent(s) to form a substituted or unsubstituted, mono- or polycyclic, (C3-C25) alicyclic or aromatic ring, whose carbon atom(s) may be replaced with at least one heteroatom selected from nitrogen and sulfur; and the heteroaryl contains at least one heteroatom selected from B, N, O, S, Si, and P. For example, $R_2$ to $R_4$, each independently, may be selected from the group consisting of hydrogen, a substituted phenyl, a substituted triazinyl, a substituted pyrimidinyl, a substituted or unsubstituted carbazolyl, a substituted benzocarbazolyl, an unsubstituted dibenzocarbazolyl, and a substituted or unsubstituted diphenylamino, or may be linked to an adjacent substituent(s) to form a substituted indene ring, or a substituted benzothiophene ring. Also, for example, $R_5$ and $R_6$, each independently, may be selected from the group consisting of hydrogen, a substituted or unsubstituted phenyl, a substituted or unsubstituted carbazolyl, an unsubstituted benzocarbazolyl, and an unsubstituted dibenzocarbazolyl, or may be linked to an adjacent substituent(s) to form an unsubstituted benzene ring, an indole ring substituted with phenyl, a benzoindole ring substituted with phenyl, an indene ring substituted with methyl, or a benzoindene ring substituted with methyl.

In formulae 1 to 4, $X_1$ represents —N=, —NR$_7$—, —O—, or —S—; $Y_1$ represents —N=, —NR$_8$—, —O—, or —S—; with the provisos that when $X_1$ represents —N=, then $Y_1$ represents —NR$_8$—, —O—, or —S—, and when $X_1$ represents —NR$_7$—, then $Y_1$ represents —N=, —O—, or —S—, with the provisos that $X_1$ and $Y_1$ are not simultaneously —O—; $X_1$ and $Y_1$ are not simultaneously —S—; $X_1$ and $Y_1$ are not —O— and —S—, respectively; and $X_1$ and $Y_1$ are not -S— and —O—, respectively. Herein, $R_7$ and $R_8$ may be a substituted phenyl.

In formulae 1 to 4, a represents 1; and b and c, each independently, represent 1 or 2, preferably 1.

In formula 1, d represents an integer of 1 to 4, preferably 1 or 2.

In formulae 2 to 4, $L_1$ represents a single bond, a substituted or unsubstituted (C6-C30)arylene, or a substituted or unsubstituted (3- to 30-membered)heteroarylene; preferably, a single bond, or a substituted or unsubstituted (C6-C18) arylene; more preferably, a single bond, or an unsubstituted (C6-C12)arylene; and for example, a single bond, or an unsubstituted phenyl.

In formula 2, $X_2$ to $X_4$, each independently, represent —N= or —CR$_9$=; preferably, at least one of $X_2$ to $X_4$ represents —N=; and more preferably, at least two of $X_2$ to $X_4$ represent —N=. Herein, $R_9$ may be hydrogen.

In formula 2, $Ar_1$ and $Ar_2$, each independently, represent a substituted or unsubstituted (C6-C30)aryl, or a substituted or unsubstituted (3- to 30-membered)heteroaryl; preferably, a substituted or unsubstituted (C6-C25)aryl, or a substituted or unsubstituted (3- to 25-membered)heteroaryl; more preferably, an unsubstituted (C6-C20)aryl, or a substituted or unsubstituted (5- to 20-membered)heteroaryl; and for example, an unsubstituted phenyl, an unsubstituted biphenyl, an unsubstituted naphthyl, an unsubstituted dibenzothiophenyl, a fluorenyl substituted with methyl, a benzofluorenyl substituted with methyl, a carbazolyl substituted with phenyl, a benzocarbazolyl substituted with phenyl, or an unsubstituted benzonaphthothiophenyl.

In formulae 2 to 4, e represents an integer of 1 to 3, preferably 1 or 2.

In formulae 3 and 4, Z represents a single bond, or a substituted or unsubstituted (C1-C6)alkylene; and preferably, a single bond.

In formula 3, n represents 0 or 1; and f and g, each independently, represent an integer of 1 to 4, preferably 1 or 2.

In formula 4, n represents 0 or 1, preferably 1; g represents an integer of 1 to 4, preferably 1 or 2; and h represents an integer of 1 to 3, preferably 1 or 2.

In formula 4, W represents —NR$_{10}$—, —O—, —S—, or —CR$_{11}$R$_{12}$—, preferably —NR$_{10}$—.

In formula 4, $R_{10}$ represents a substituted or unsubstituted (C6-C30)aryl, or a substituted or unsubstituted (3- to 30-membered)heteroaryl; preferably, a substituted or unsubstituted (C6-C20)aryl; more preferably, an unsubstituted (C6-C18)aryl; and for example, an unsubstituted phenyl.

In formula 4, $R_{11}$ and $R_{12}$, each independently, represent a substituted or unsubstituted (C1-C30)alkyl, a substituted or unsubstituted (C6-C30)aryl, or a substituted or unsubstituted (3- to 30-membered)heteroaryl; preferably, each independently, represent a substituted or unsubstituted (C1-C20) alkyl; more preferably, each independently, represent an unsubstituted (C1-C15)alkyl; and for example, an unsubstituted methyl.

Herein, "(C1-C30)alkyl" is meant to be a linear or branched alkyl having 1 to 30 carbon atoms constituting the chain, in which the number of carbon atoms is preferably 1 to 20, more preferably 1 to 10, and includes methyl, ethyl, n-propyl, isopropyl, n-butyl, isobutyl, tert-butyl, etc.; "(C3-C30)cycloalkyl" is a mono- or polycyclic hydrocarbon having 3 to 30 ring backbone carbon atoms, in which the number of carbon atoms is preferably 3 to 20, more preferably 3 to 7, and includes cyclopropyl, cyclobutyl, cyclopentyl, cyclohexyl, etc.; "(C6-C30)aryl(ene)" is a monocyclic or fused ring derived from an aromatic hydrocarbon having 6 to 30 ring backbone carbon atoms, in which the number of carbon atoms is preferably 6 to 20, more preferably 6 to 15, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, etc.; and "(3- to 30-membered) heteroaryl(ene)" is an aryl having 3 to 30 ring backbone atoms, preferably 5 to 25 ring backbone atoms, including at least one, preferably 1 to 4 heteroatoms selected from the group consisting of B, N, O, S, Si, and P; may be a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, quinoxalinyl, carbazolyl, benzocarbazolyl, dibenzocarbazolyl, phenoxazinyl, phenanthridinyl, benzodioxolyl, etc. Furthermore, "halogen" includes F, Cl, Br, and I.

Herein, "substituted" in the expression "substituted or unsubstituted" means that a hydrogen atom in a certain functional group is replaced with another atom or group, i.e. a substituent. The substituents of the substituted alkyl(ene), the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted mono- or di-alkylamino, the substituted mono- or di-arylamino, the substituted alkylarylamino, and the substituted mono- or polycyclic, alicyclic or aromatic ring in $R_1$ to $R_{12}$, $L_1$, $Ar_1$, $Ar_2$, and Z of formulae 1 to 4, each independently, are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with (C1-C6)alkyl or (C6-C30)aryl; a (C6-C30)aryl unsubstituted or substituted with cyano, (3- to 30-membered)heteroaryl, or mono- or di-(C6-C30)arylamino; a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di- (C1-C30)alkylamino; a mono- or di- (C6-C30)arylamino; a (C1-C30)alkyl(C6-C30)arylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl; preferably, each independently, are at least one selected from the group consisting of a (C1-C6)alkyl; a (C6-C30)aryl unsubstituted or substituted with (3- to 30-membered)heteroaryl or di(C6-C30)arylamino; a (3- to 30-membered)heteroaryl unsubstituted or substituted with (C1-C6)alkyl or (C6-C30)aryl; and a mono- or di- (C6-C30)arylamino; or are linked to an adjacent substituent(s) to form a substituted or unsubstituted, mono- or polycyclic, (C5-C30) alicyclic or aromatic ring, whose carbon atom(s) may be replaced with at least one heteroatom selected from nitrogen, oxygen, and sulfur; and for example, an unsubstituted methyl, a phenyl unsubstituted or substituted with carbazolyl or diphenylamino, an unsubstituted biphenyl, an unsubstituted naphthyl, a fluorenyl substituted with methyl, a benzofluorenyl substituted with methyl, an unsubstituted a dibenzothiophenyl, a carbazolyl unsubstituted or substituted with phenyl, a benzocarbazolyl unsubstituted or substituted with phenyl, an unsubstituted dibenzocarbazolyl, a pyrimidinyl substituted with phenyl, an unsubstituted benzonaphthothiophenyl, or an unsubstituted di(C6-C12)arylamino, or are linked to an adjacent substitutent(s) to form an indole ring substituted with phenyl, a benzoindole ring substituted with phenyl, an unsubstituted benzene ring, a benzindene ring substituted with methyl, or an indene ring substituted with methyl.

The organic electroluminescent compound represented by formula 1 includes the following compounds, but is not limited thereto:

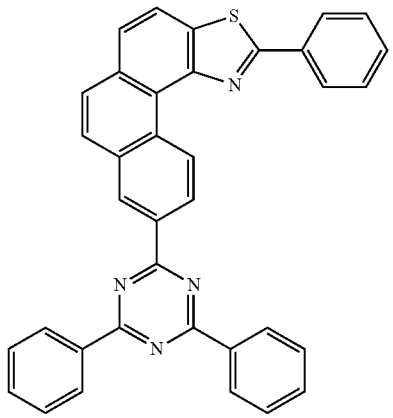

C-1

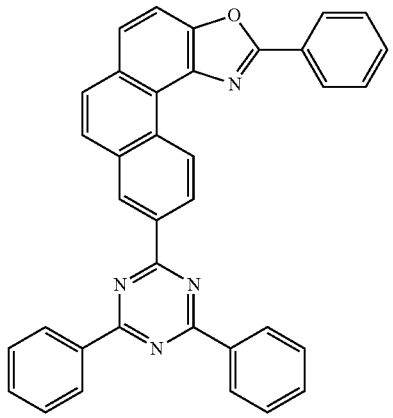

C-2

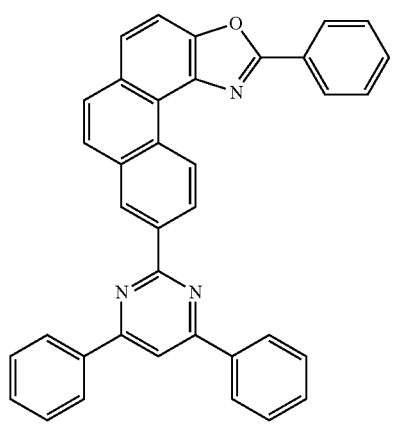
C-3
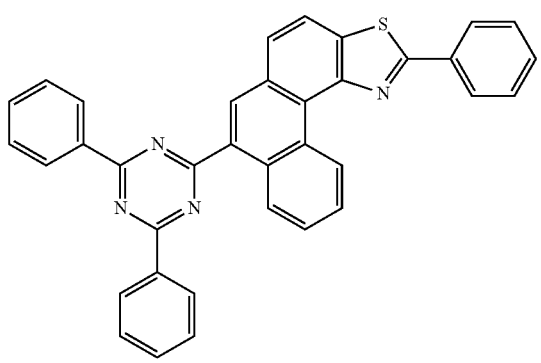
C-6
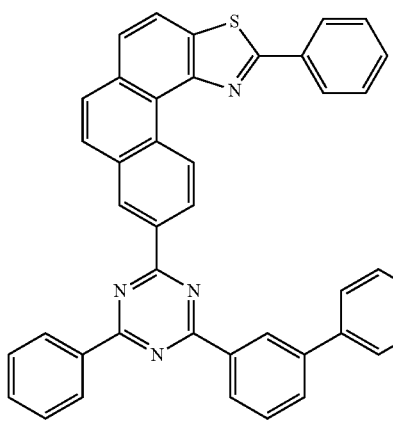
C-4
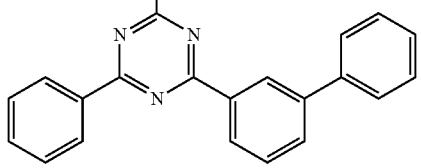
C-7
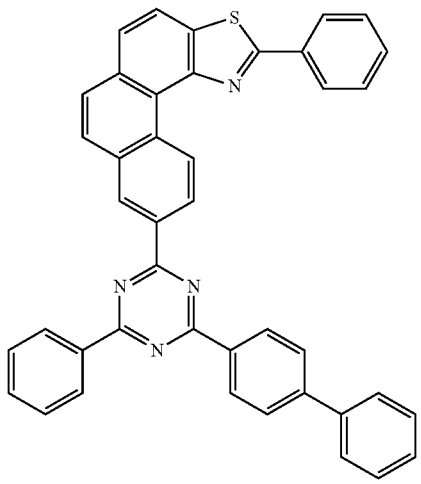
C-5
C-8

C-9
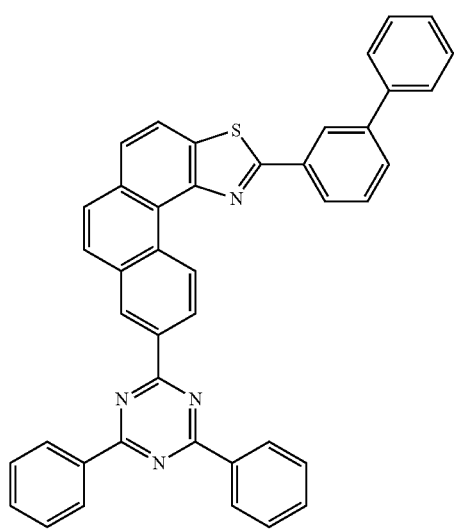
C-10
C-11
C-12
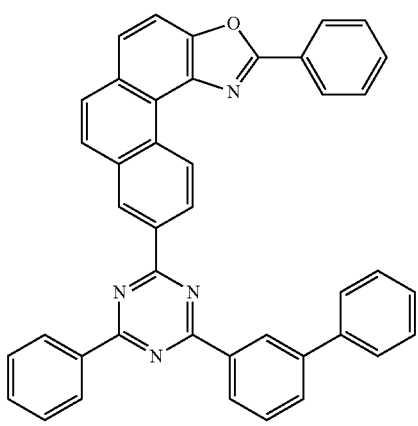
C-13
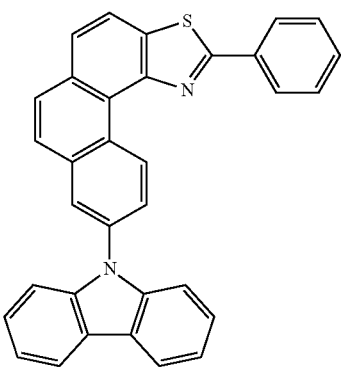
C-14
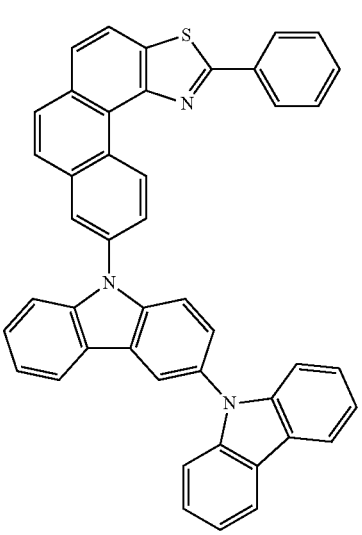

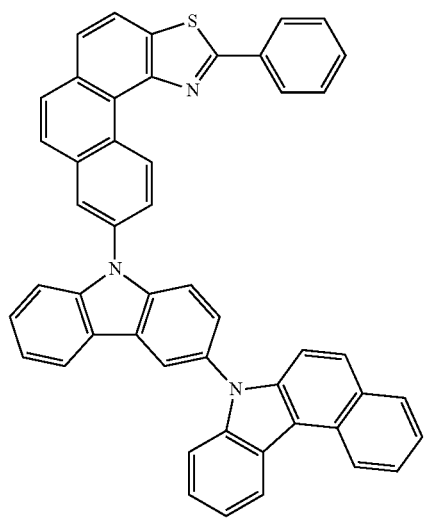
C-15
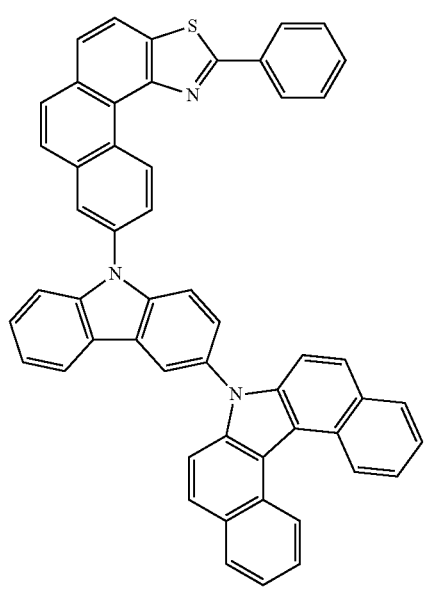
C-16
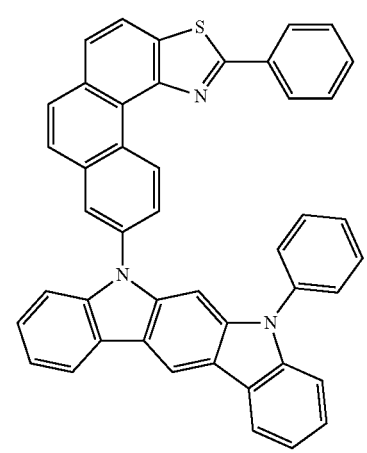
C-17
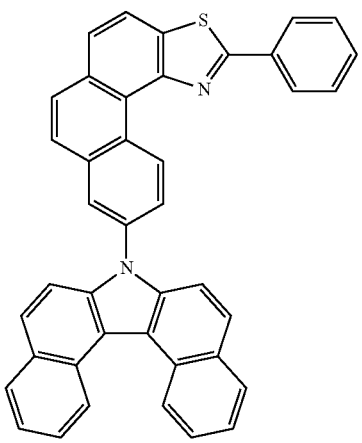
C-18
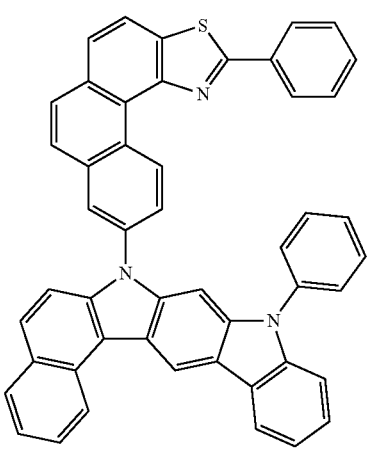
C-19
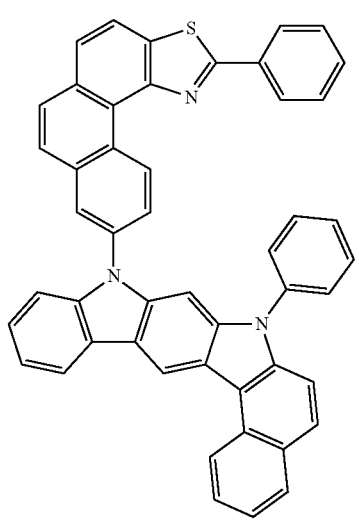
C-20

C-21
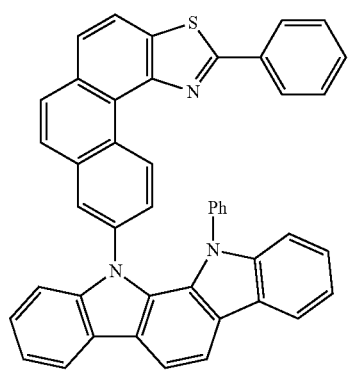
C-22
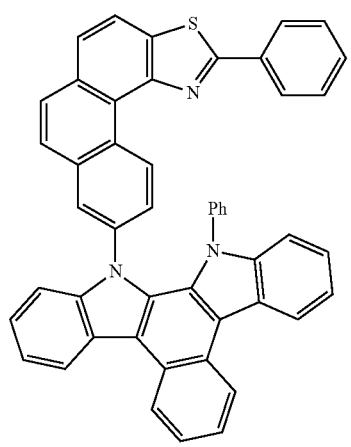
C-23
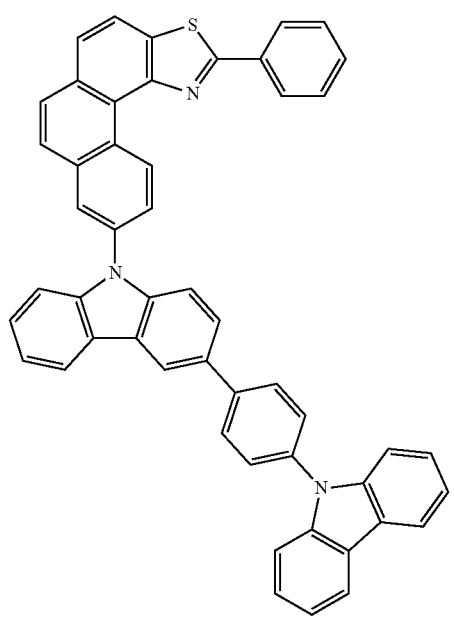
C-24
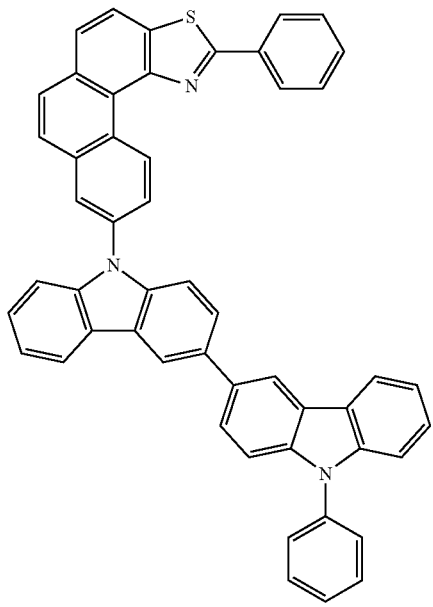
C-25
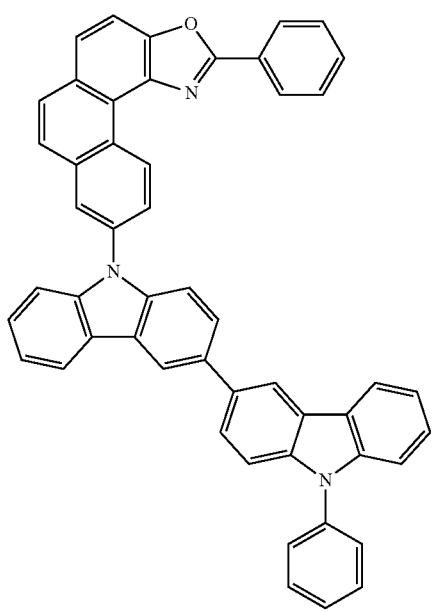

-continued
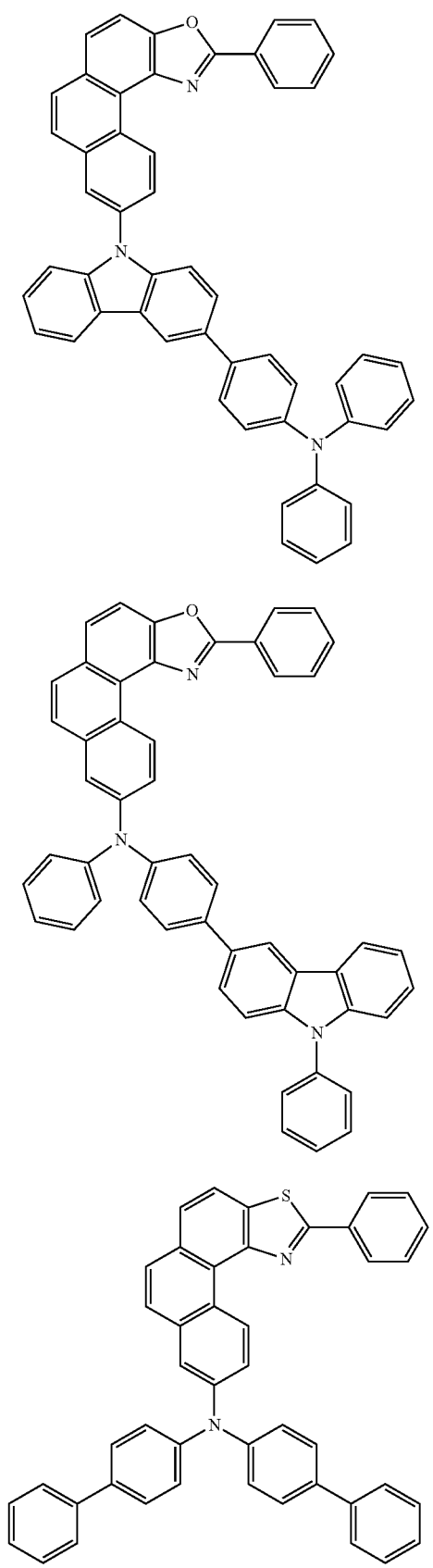
C-26
C-27
C-28
-continued
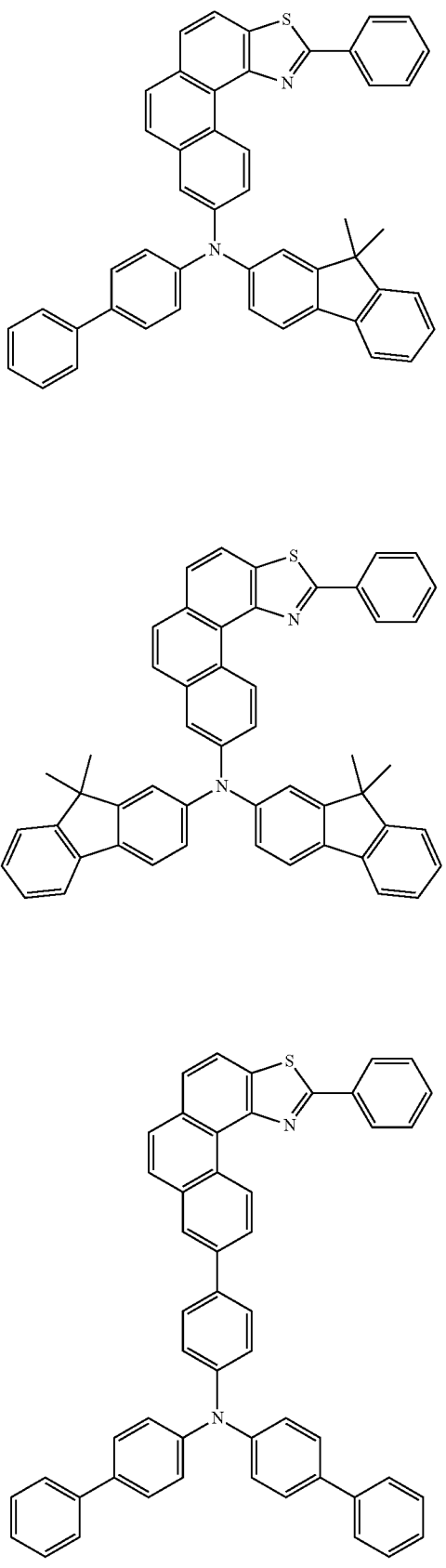
C-29
C-30
C-31

C-32
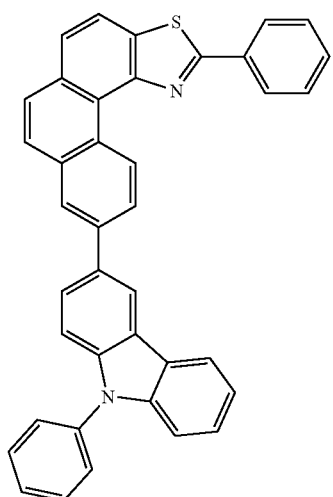
C-33
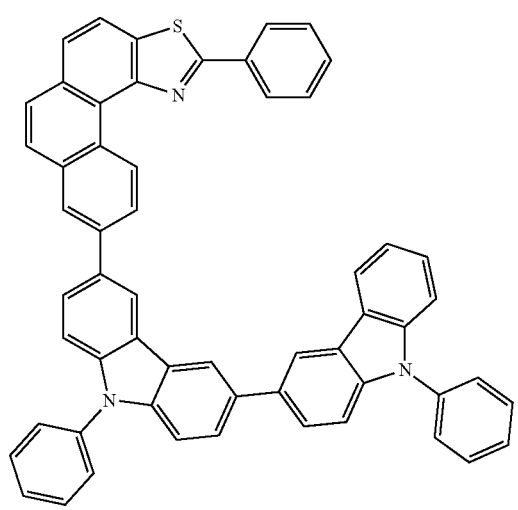
C-34
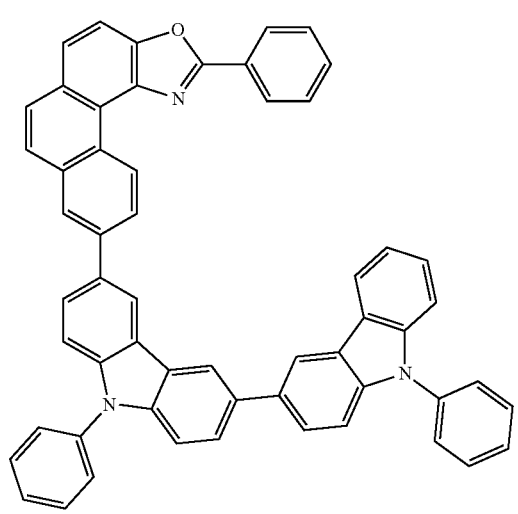
C-35
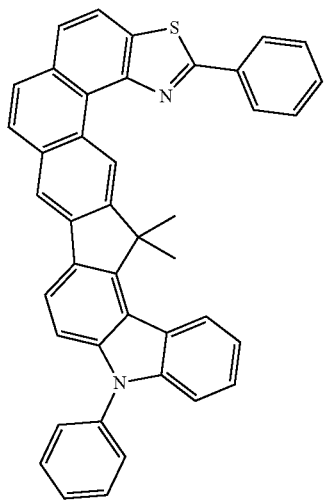
C-36
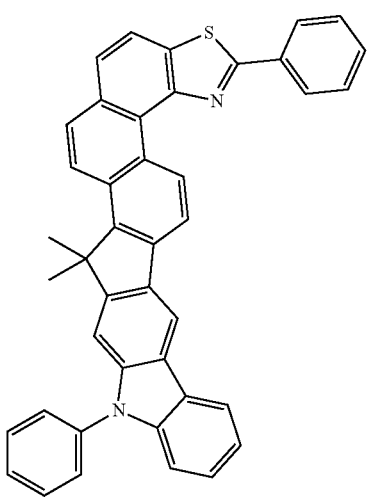
C-37
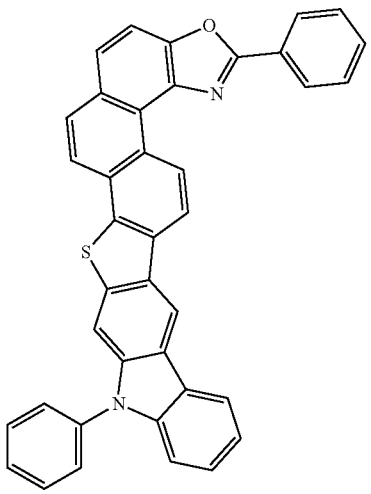

C-38
C-39
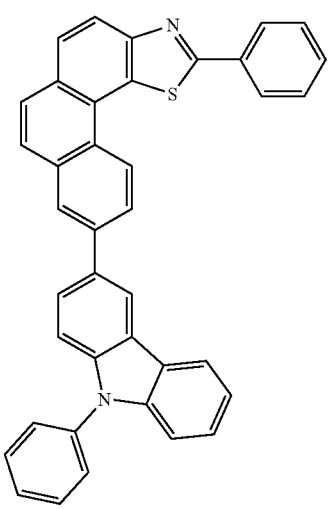
C-40
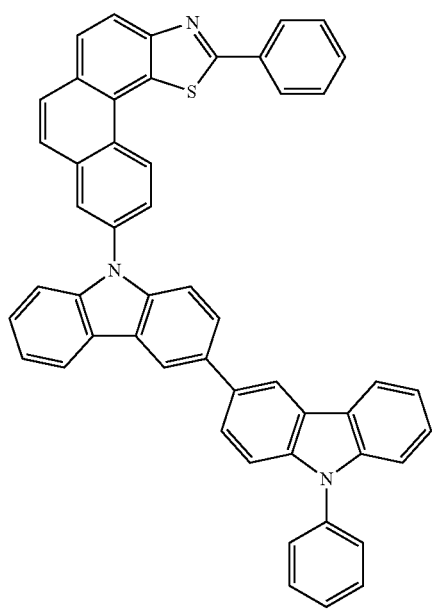
C-41
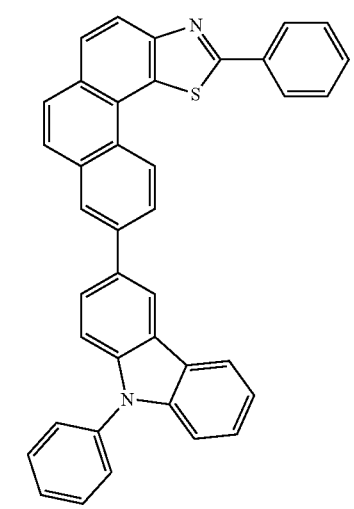
C-42
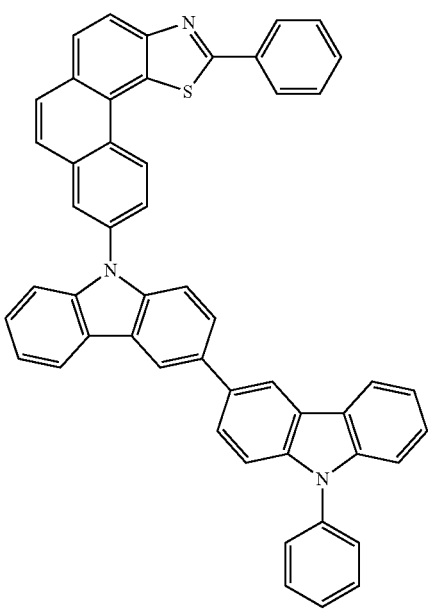

C-43
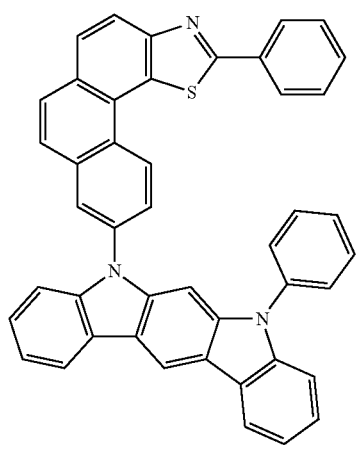
C-44
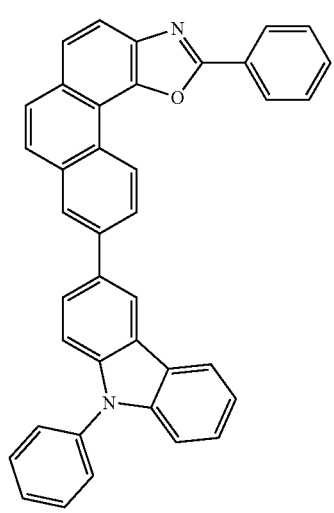
C-45
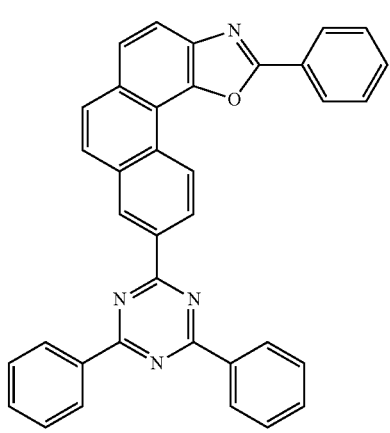
C-46
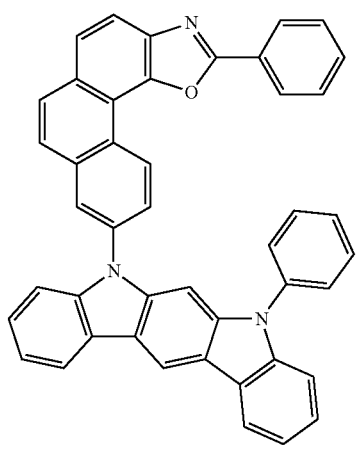
C-47
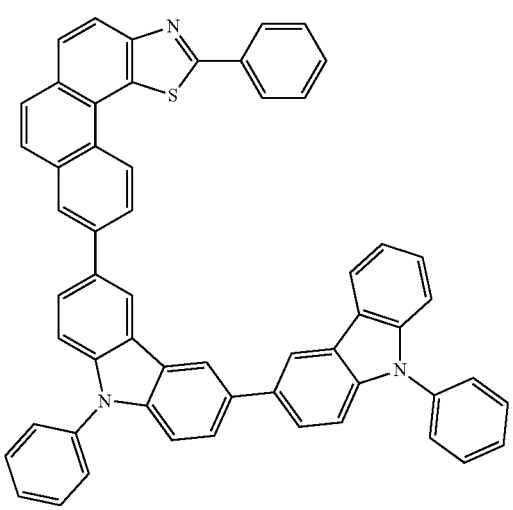
C-48
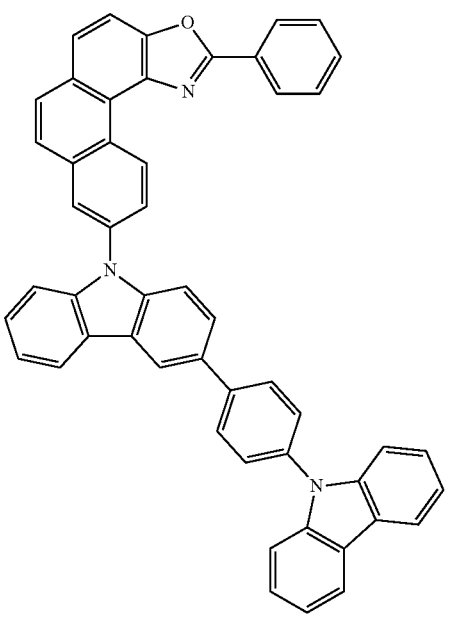

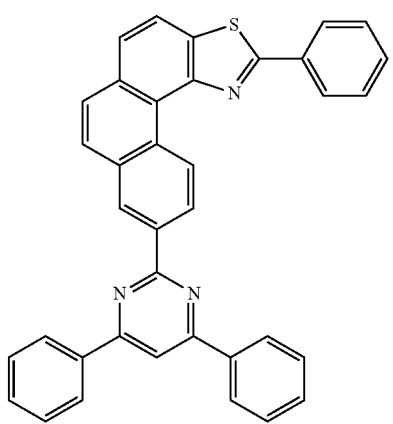
C-49
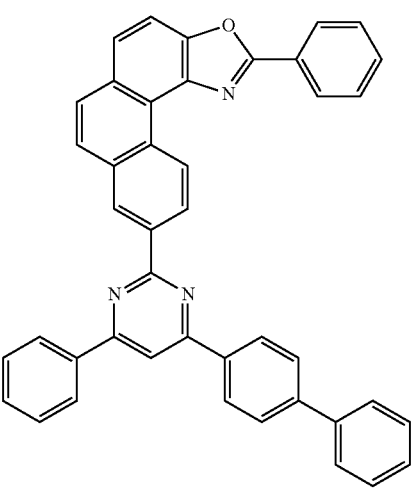
C-52
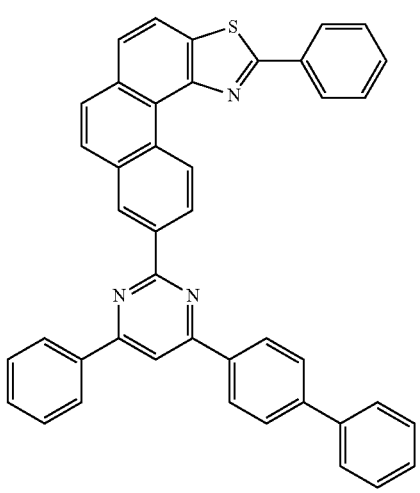
C-50
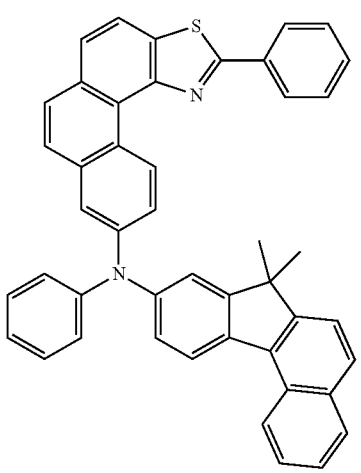
C-53
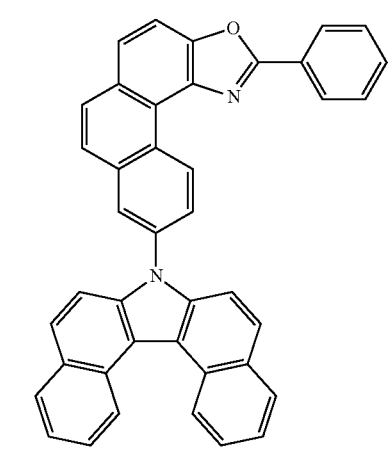
C-51
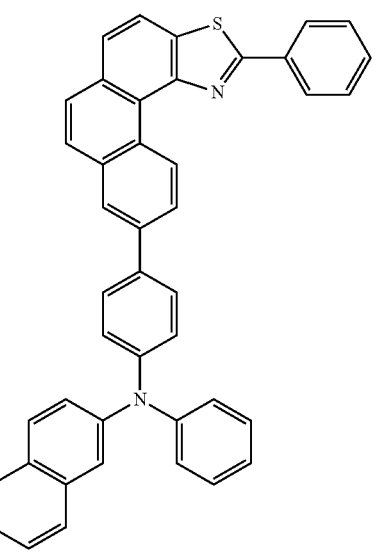
C-54

C-55 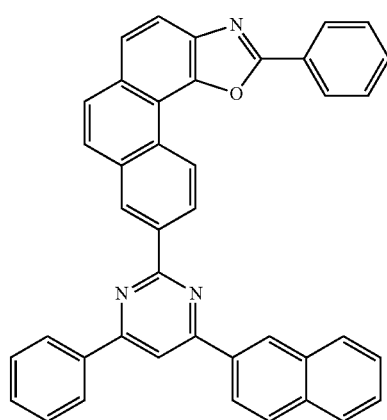
C-58 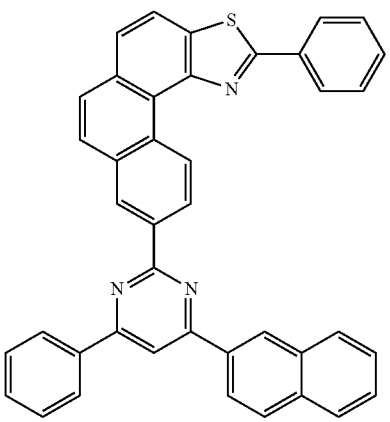
C-56 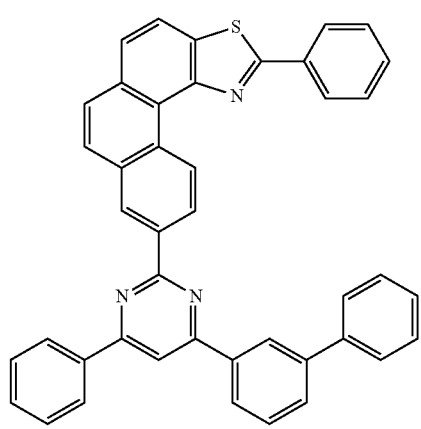
C-59 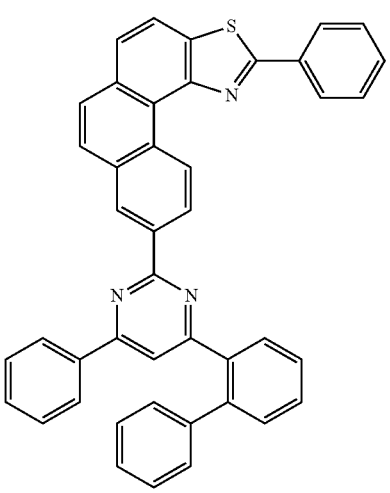
C-57 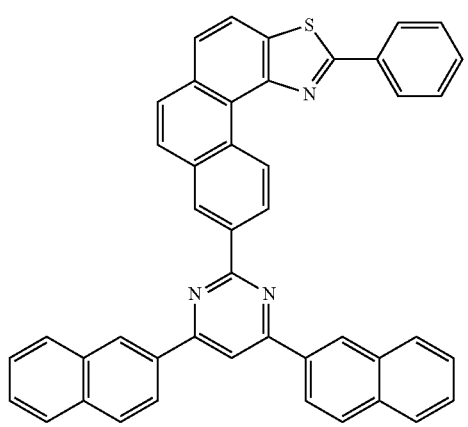
C-60 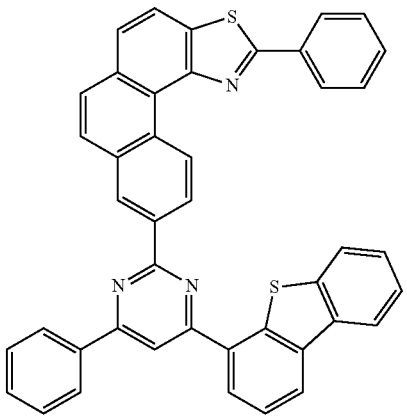

C-61
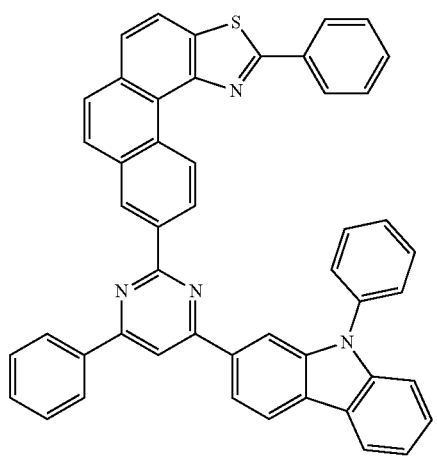
C-62
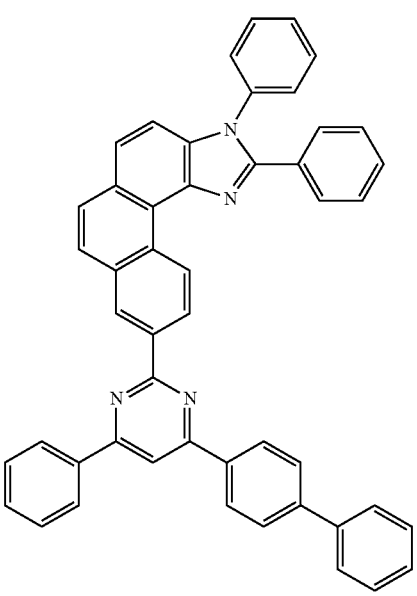
C-63
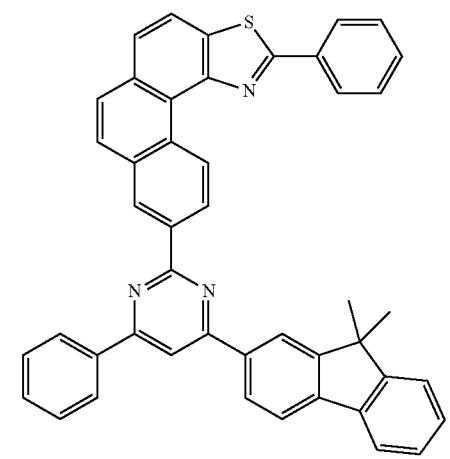
C-64
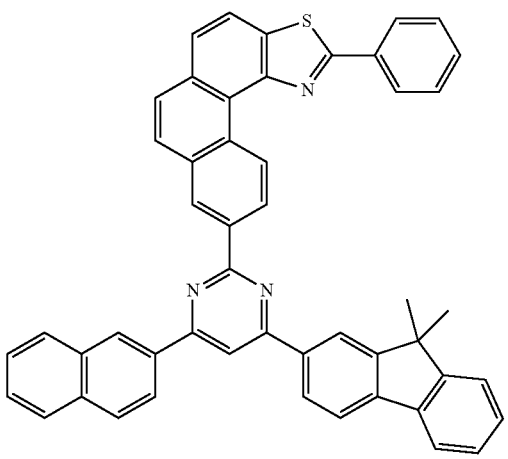
C-65
C-66
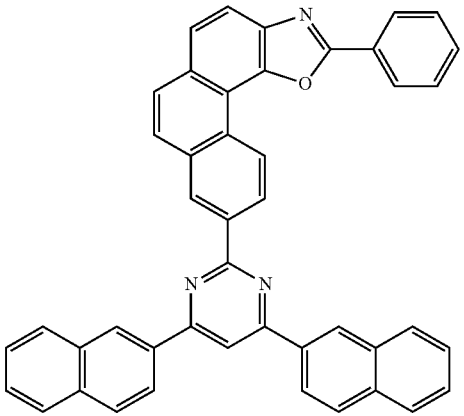

C-67
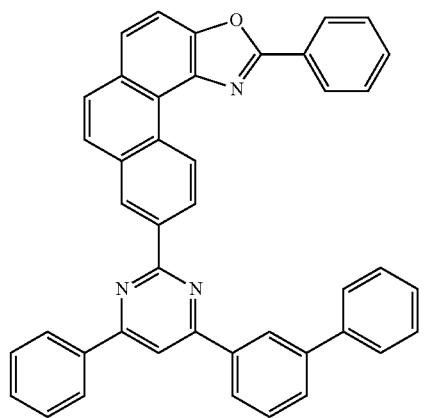
C-68
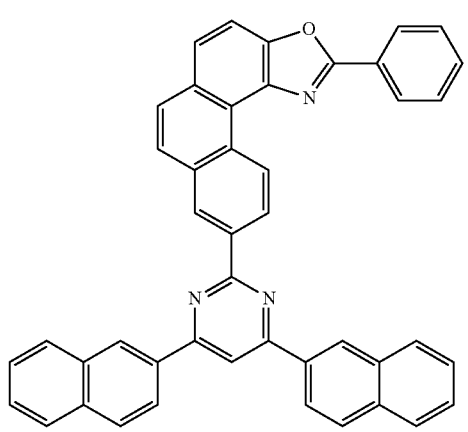
C-69
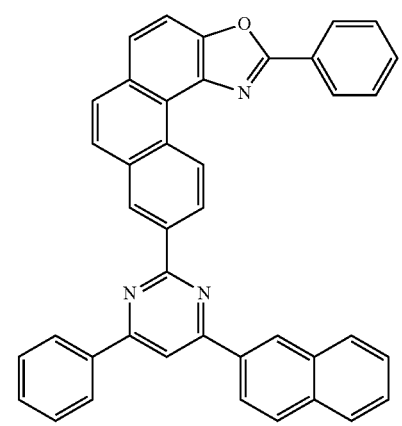
C-70
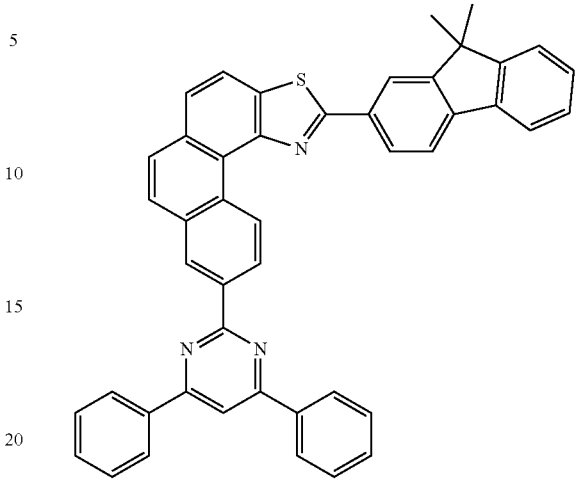
C-71
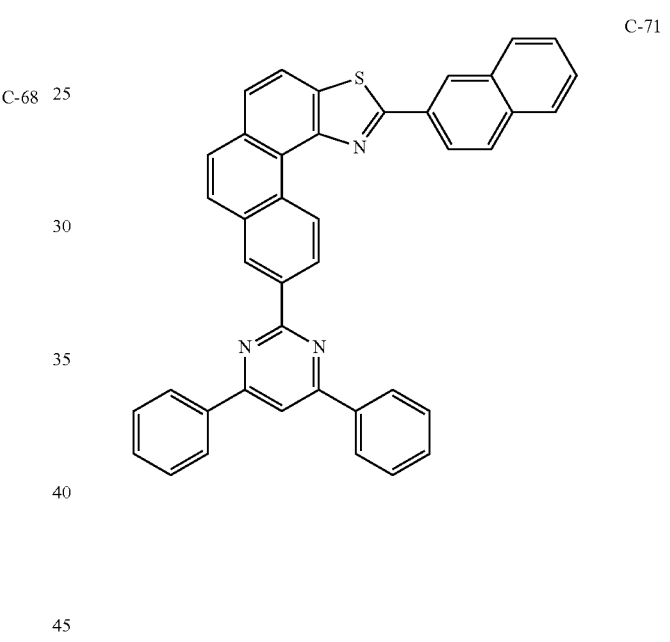
C-72
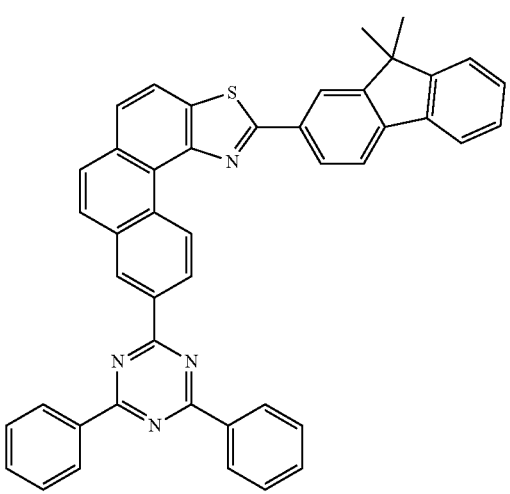

-continued
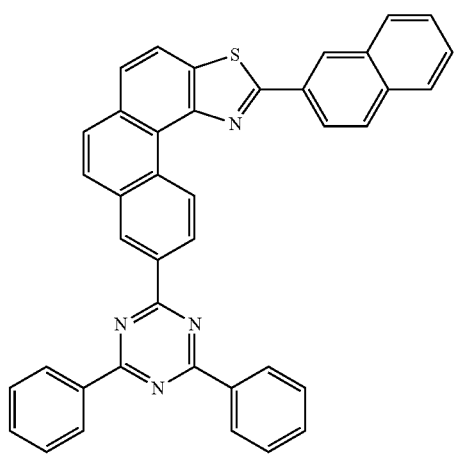
C-73
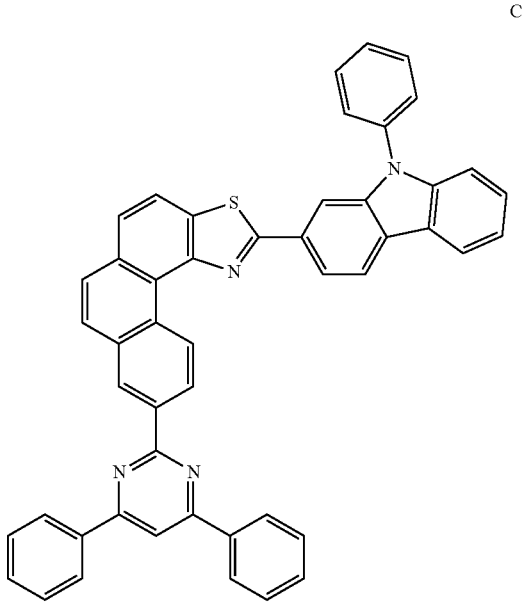
C-74
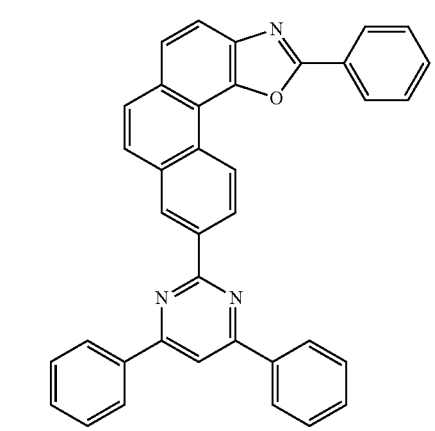
C-75
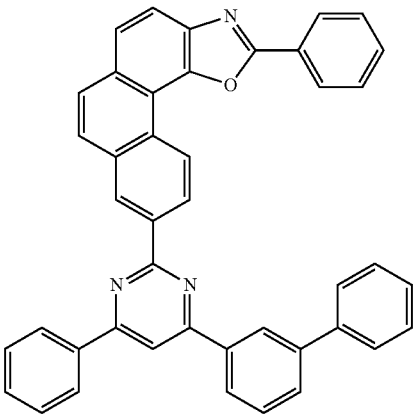
C-76
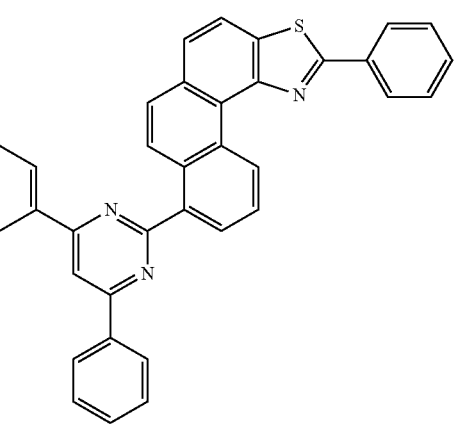
C-77
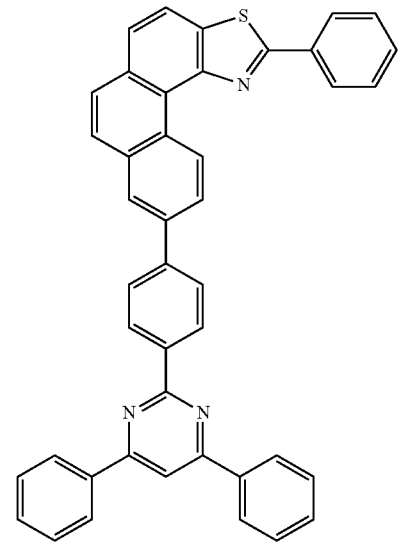
C-78

-continued
C-79
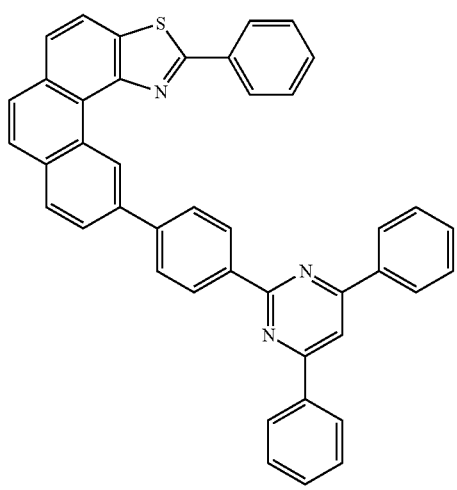
C-80
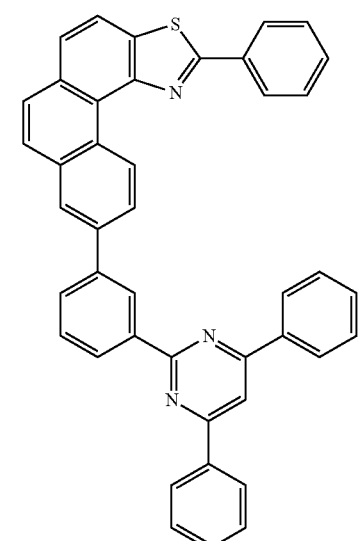
C-81
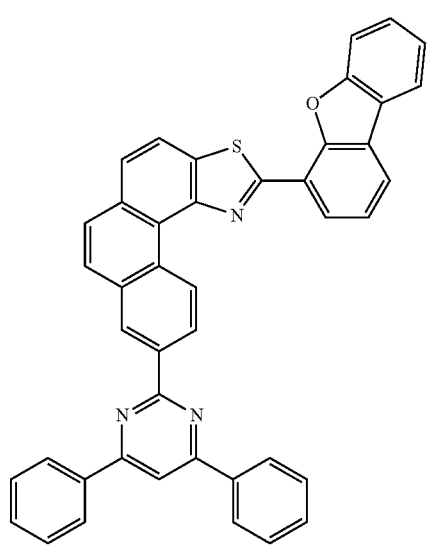
C-82
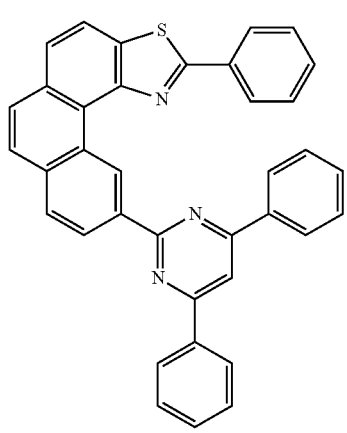
C-83
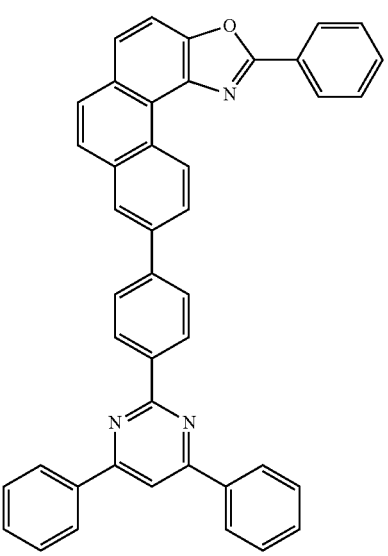
C-84
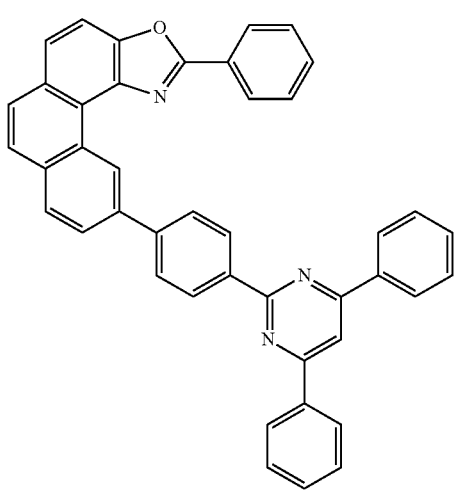

C-85
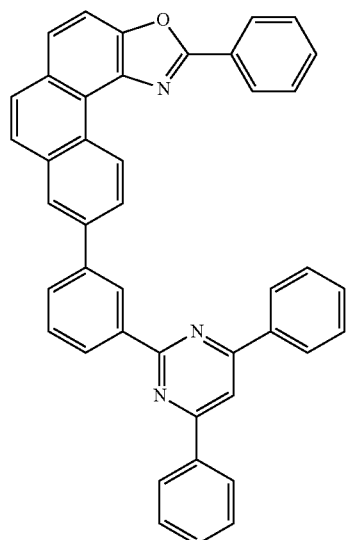
C-86
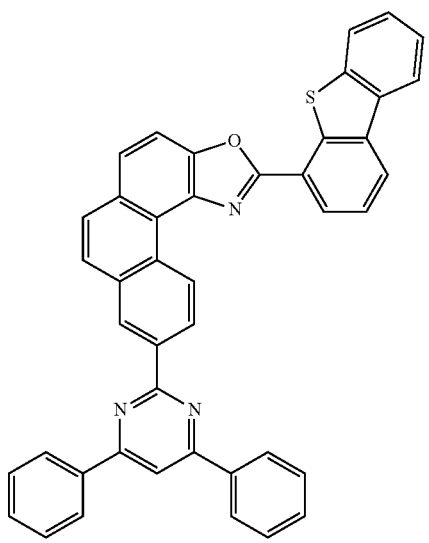
C-87
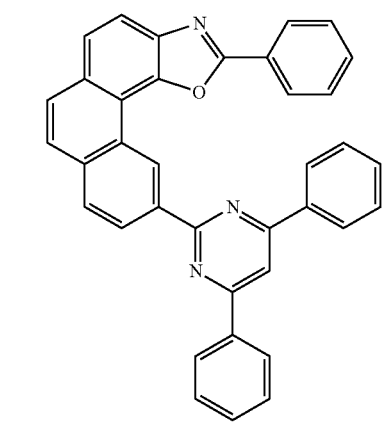
C-88
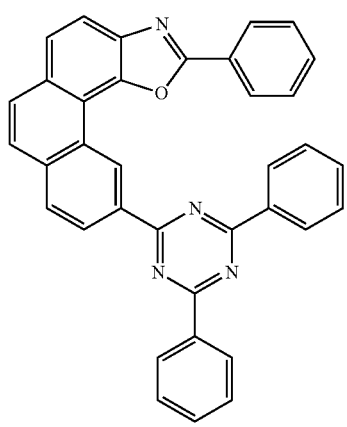
C-89
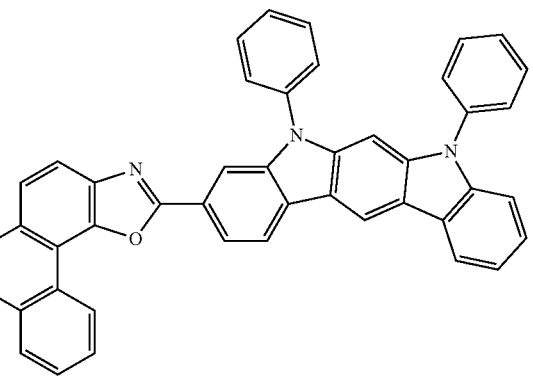
C-90
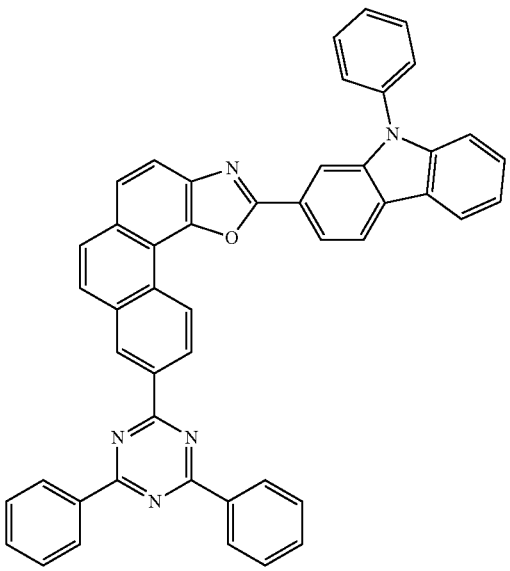

C-91
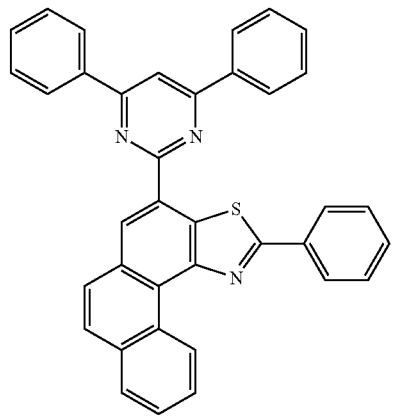
C-92
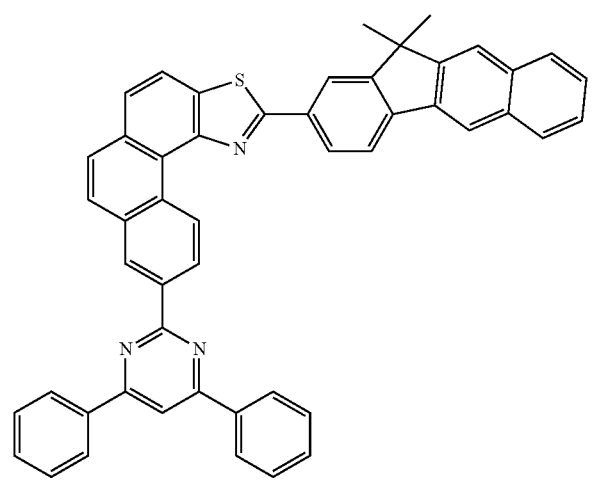
C-93
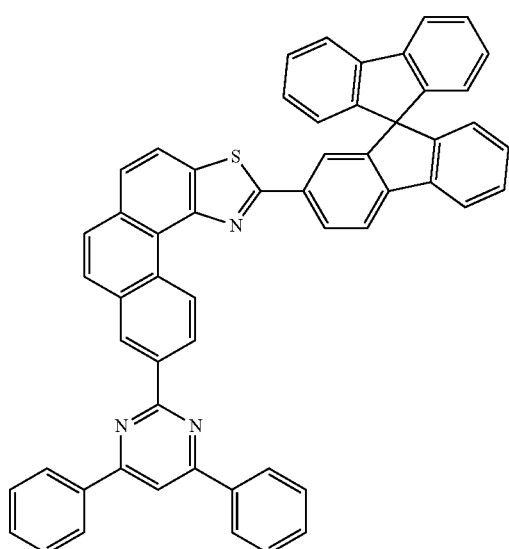
C-94
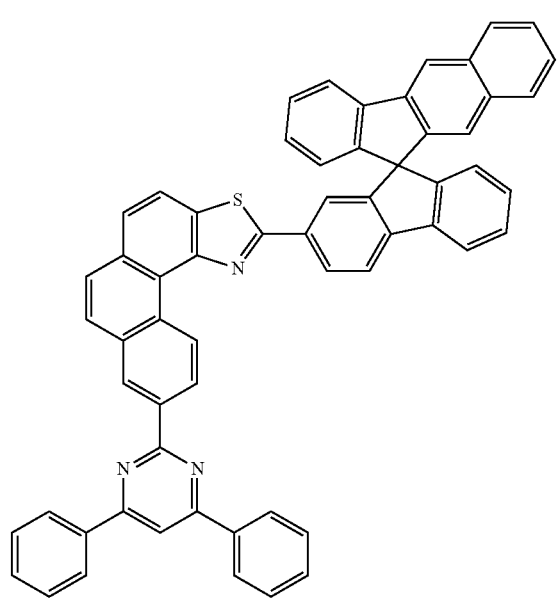
C-95
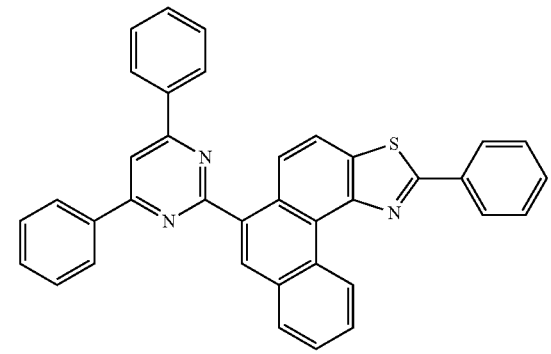
C-96
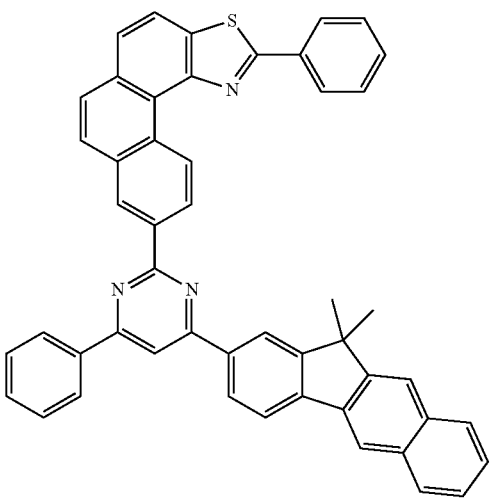

C-97

C-98

C-99

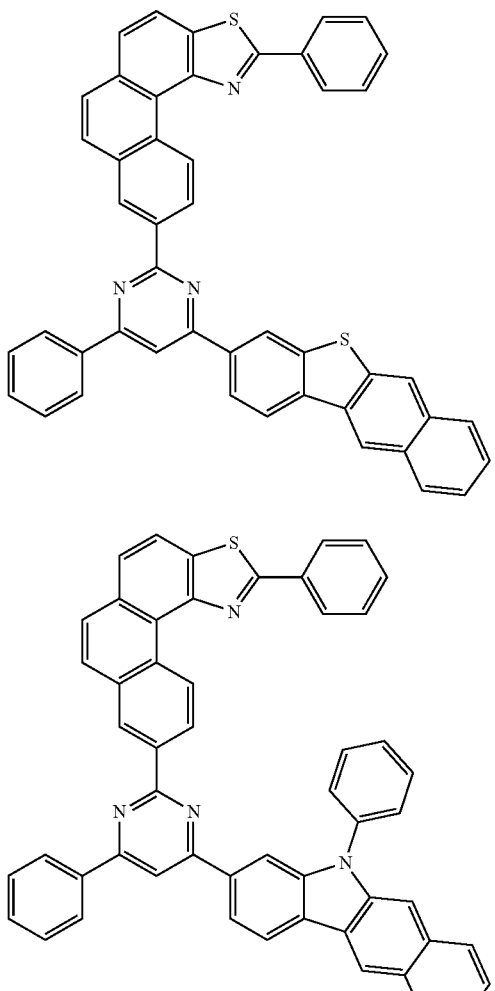

C-100

C-101

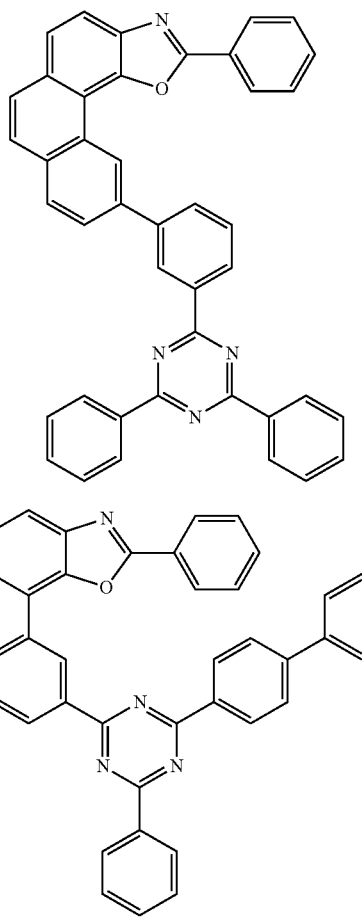

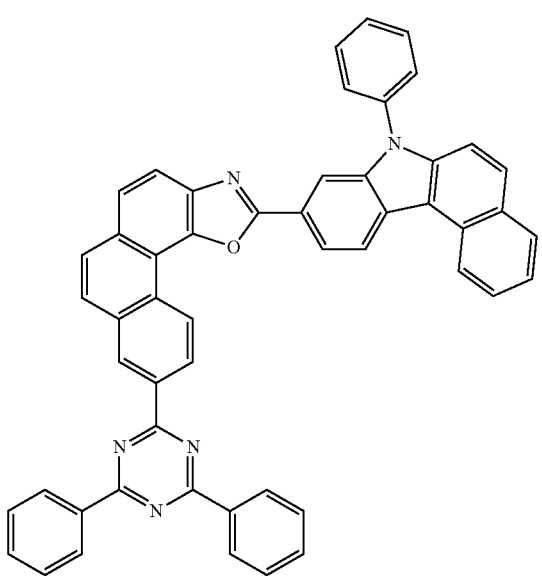

The present disclosure further provides an organic electroluminescent material comprising the organic electroluminescent compound of formula 1, and an organic electroluminescent device comprising the organic electroluminescent material.

The organic electroluminescent material can be comprised of the organic electroluminescent compound of the present disclosure alone, or can further include conventional materials generally used in organic electroluminescent materials.

The organic electroluminescent device of the present disclosure may comprise a first electrode, a second electrode, and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, an electron transport layer, an electron buffer layer, an electron injection layer, an interlayer, a hole blocking layer, and an electron blocking layer.

The organic electroluminescent compound of formula 1 of the present disclosure can be comprised in the light-emitting layer as a host material or in an electron buffer layer. Preferably, the light-emitting layer may comprise at least one dopant. If necessary, another compound besides the organic electroluminescent compound of formula 1 may be comprised as a second host material.

Another embodiment of the present disclosure provides an electron buffer material comprising the organic electroluminescent compound of formula 1, and an organic electroluminescent device comprising the electron buffer material.

The organic electroluminescent device of the present disclosure comprises a first electrode; a second electrode opposing the first electrode; a light-emitting layer between the first electrode and the second electrode; and an electron transport zone and an electron buffer layer between the light-emitting layer and the second electrode. The electron buffer layer may comprise a compound represented by formula 1. When using the above compound, the driving voltage, the efficiency, and the lifespan of the device can be improved.

The dopant used in the present disclosure is preferably at least one phosphorescent dopant. The phosphorescent dopant material used for the organic electroluminescent device of the present disclosure is not limited, but may be preferably selected from metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant to be comprised in the organic electroluminescent device of the present disclosure may be selected from the group consisting of the compounds represented by the following formulae 10 to 12.

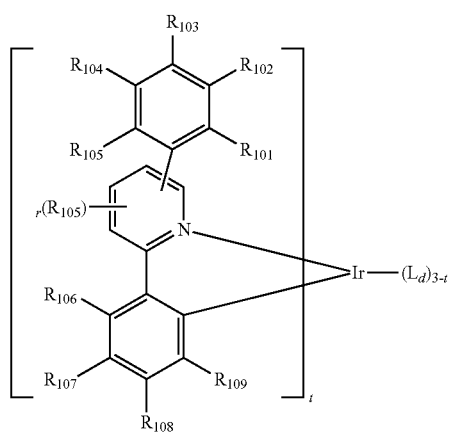

(10)

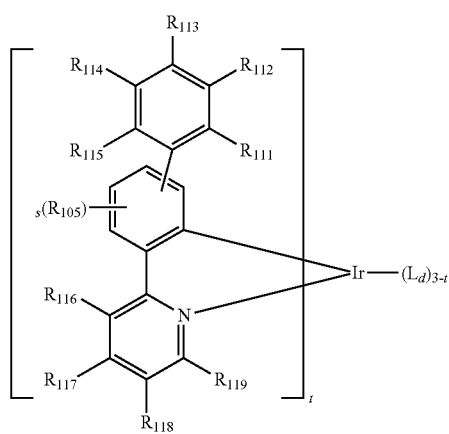

(11)

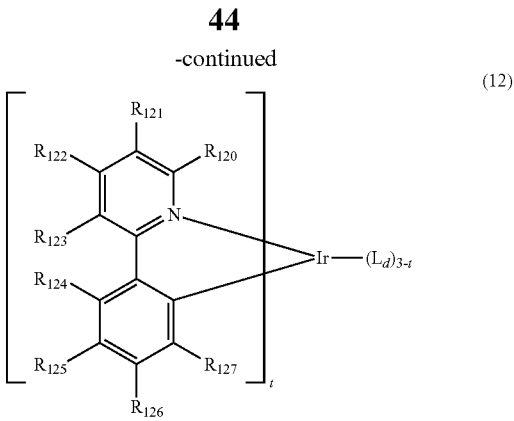

(12)

wherein $L_d$ is selected from the following structures:

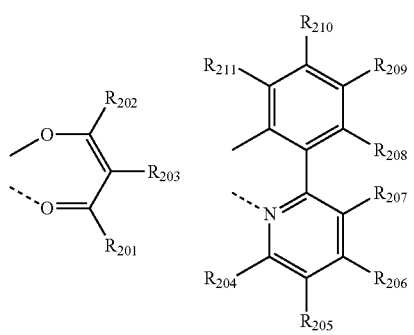

$R_{100}$ represents hydrogen, a substituted or unsubstituted (C1-C30)alkyl, or a substituted or unsubstituted (C3-C30) cycloalkyl;

$R_{101}$ to $R_{109}$ and $R_{111}$ to $R_{123}$, each independently, represent hydrogen, deuterium, a halogen, a substituted or unsubstituted (C1-C30)alkyl, a substituted or unsubstituted (C3-C30)cycloalkyl, a cyano, or a substituted or unsubstituted (C1-C30)alkoxy; and adjacent substituents of $R_{120}$ to $R_{123}$ may be linked to each other to form a substituted or unsubstituted fused ring, e.g., a substituted or unsubstituted quinoline;

$R_{124}$ to $R_{127}$, each independently, represent hydrogen, deuterium, a halogen, a substituted or unsubstituted (C1-C30)alkyl, or a substituted or unsubstituted (C6-C30)aryl; and adjacent substituents of $R_{124}$ to $R_{127}$ may be linked to each other to form a substituted or unsubstituted fused ring, e.g., a substituted or unsubstituted fluorene, a substituted or unsubstituted dibenzothiophene, or a substituted or unsubstituted dibenzofuran;

$R_{201}$ to $R_{211}$, each independently, represent hydrogen, deuterium, a halogen, a substituted or unsubstituted a (C1-C30)alkyl, a substituted or unsubstituted (C3-C30)cycloalkyl, or a substituted or unsubstituted (C6-C30)aryl; and adjacent substituents of $R_{201}$ to $R_{211}$ may be linked to each other to form a substituted or unsubstituted fused ring, e.g., a substituted or unsubstituted dibenzofuran, or a substituted or unsubstituted dibenzothiophene;

r and s, each independently, represent an integer of 1 to 3; where r or s is an integer of 2 or more, each of $R_{100}$ may be the same or different; and t represents an integer of 1 to 3.

Specifically, the phosphorescent dopant materials include the following:

D-1
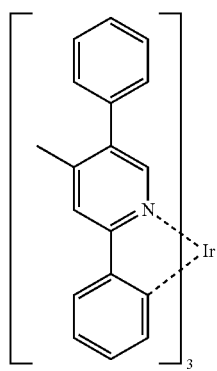
D-2
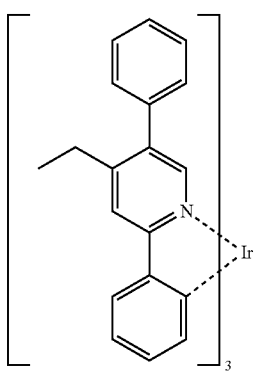
D-3
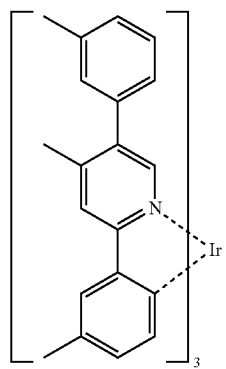
D-4
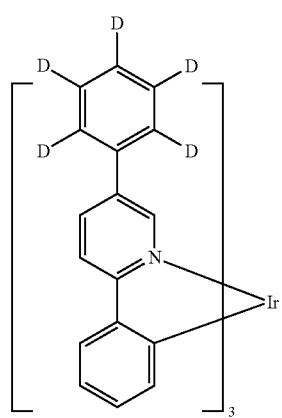
D-5
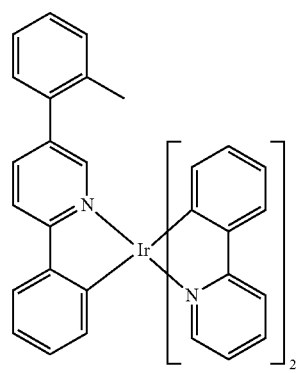
D-6
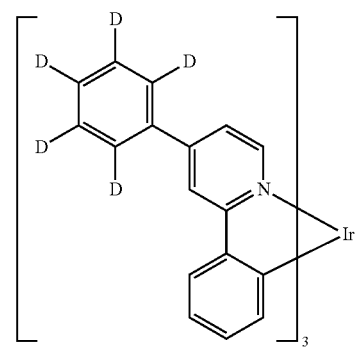
D-7
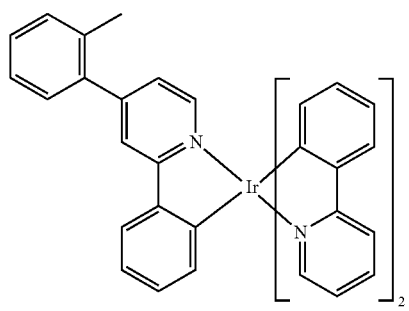
D-8
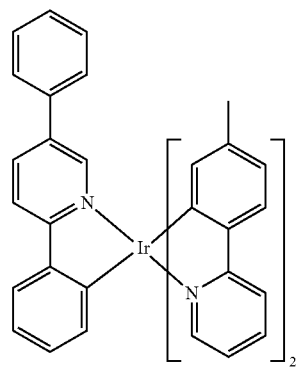

-continued
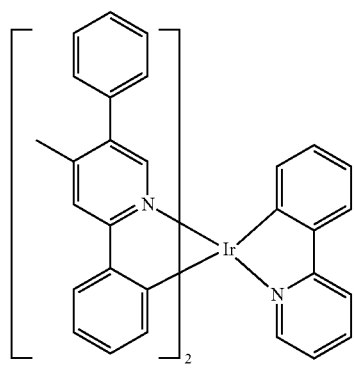
D-9
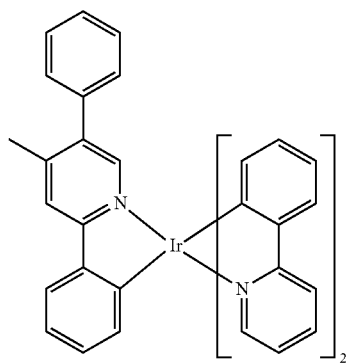
D-13
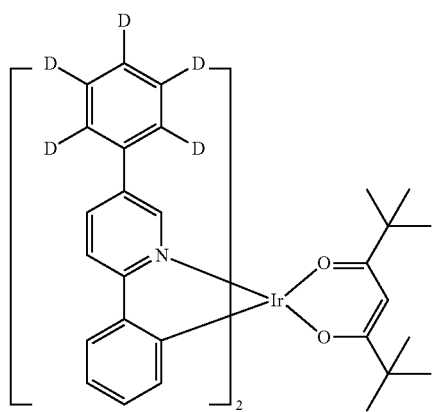
D-10
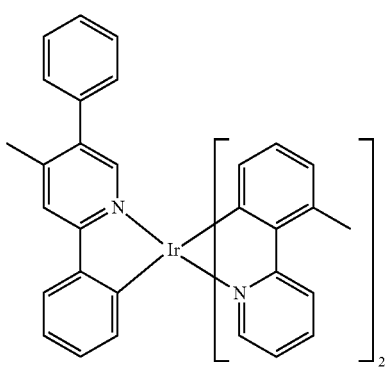
D-14
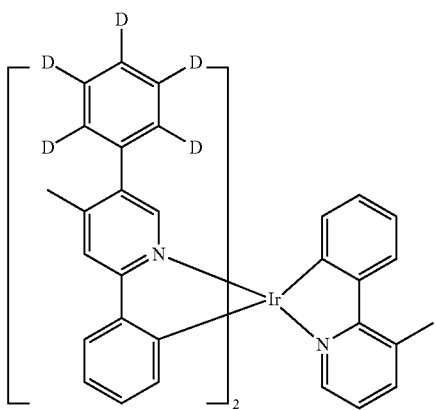
D-11
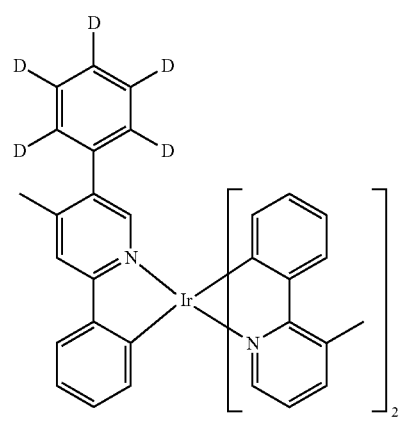
D-15
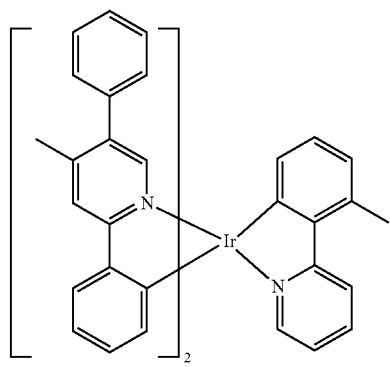
D-12
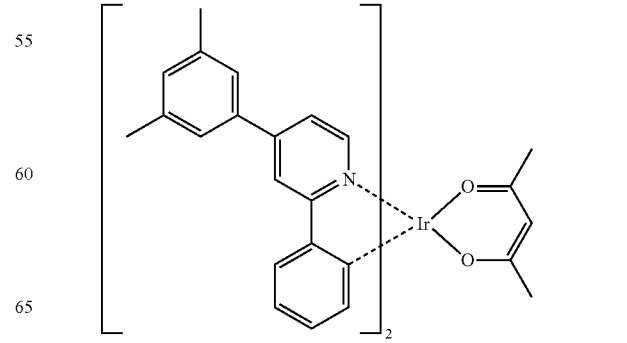
D-16

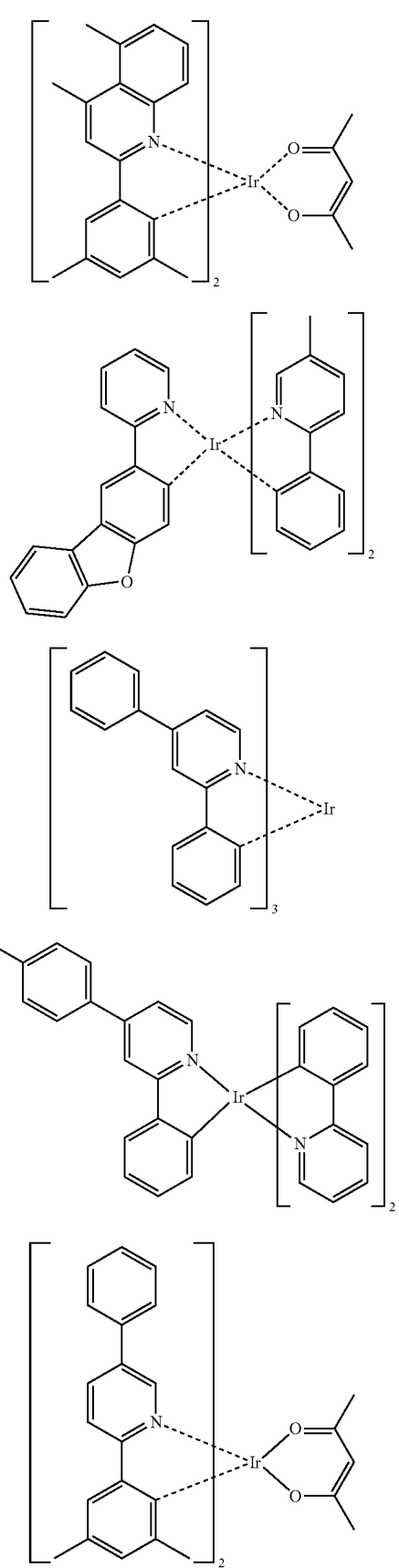
D-17
D-18
D-19
D-20
D-21
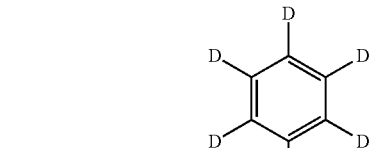
D-22
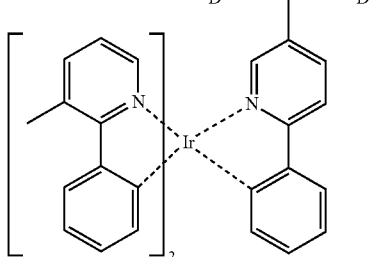
D-23
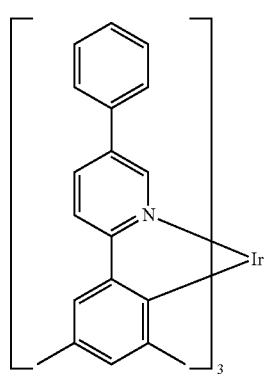
D-24
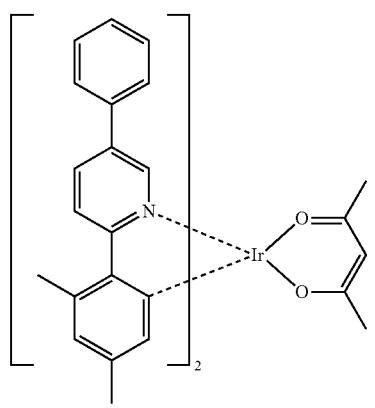
D-25
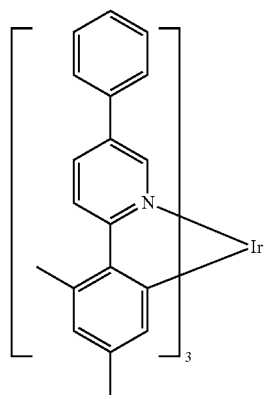

D-26 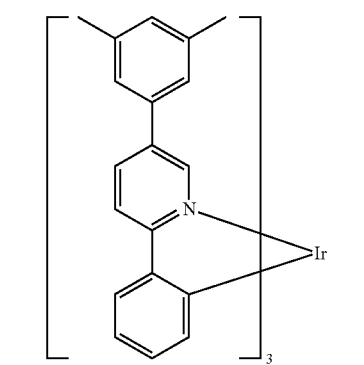
D-27 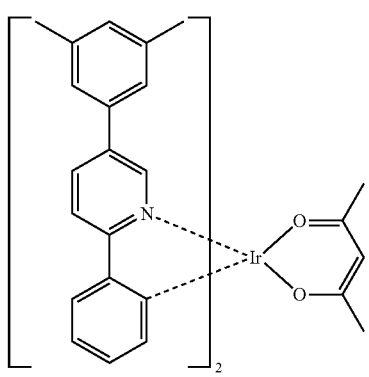
D-28 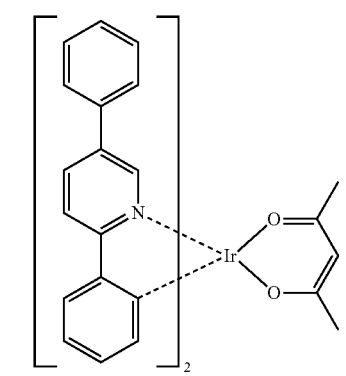
D-29 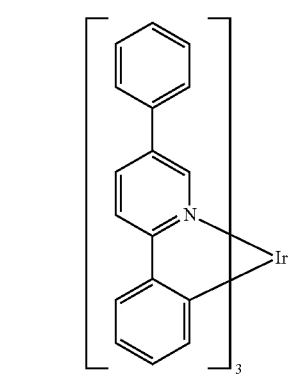
D-30 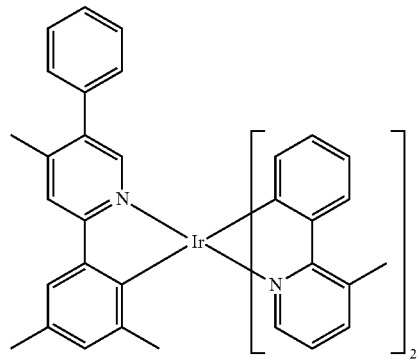
D-31 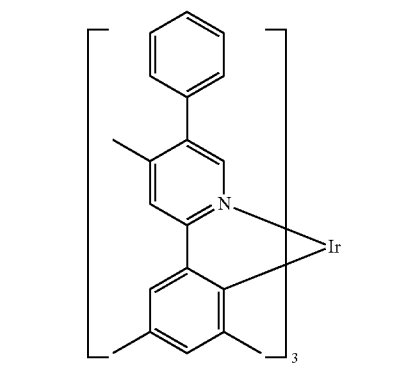
D-32 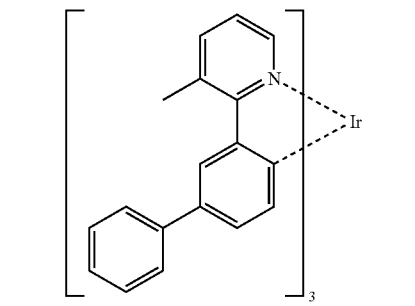
D-33 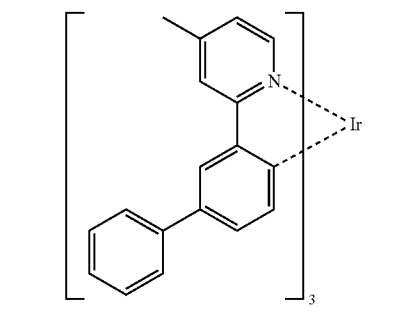
D-34 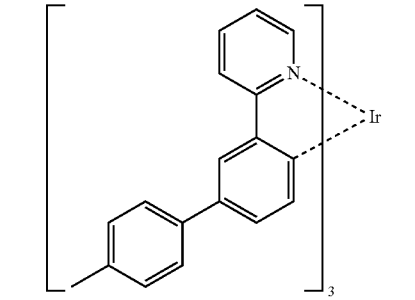

-continued
D-35
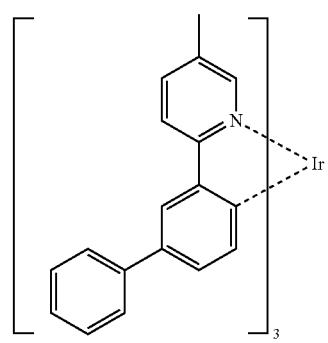
D-36
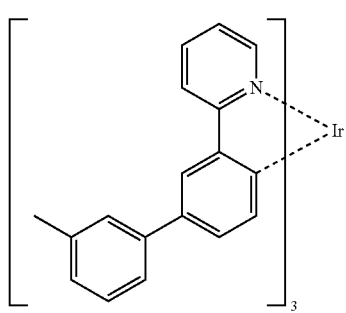
D-37
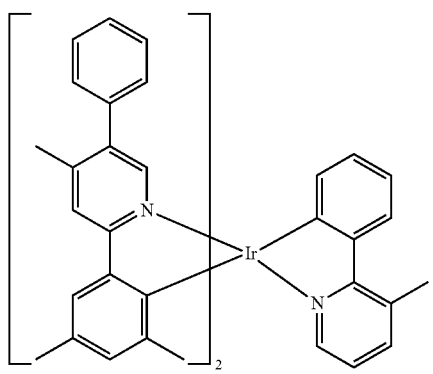
D-38
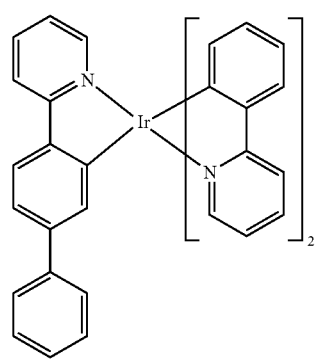
-continued
D-39
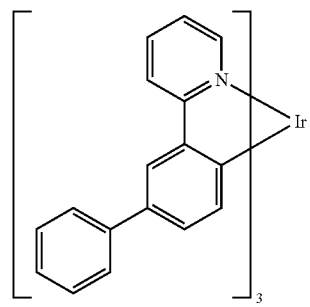
D-40
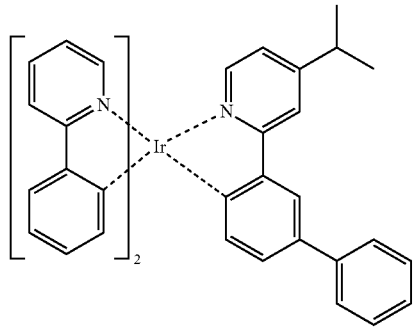
D-41
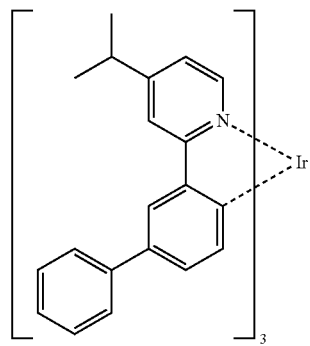
D-42
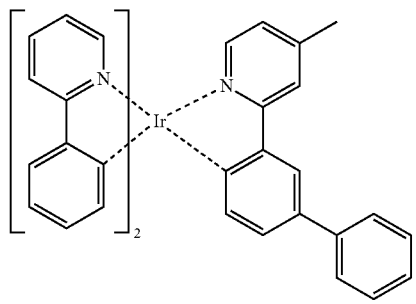
D-43
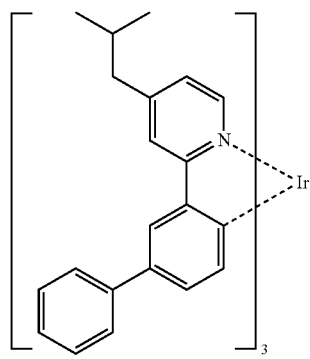

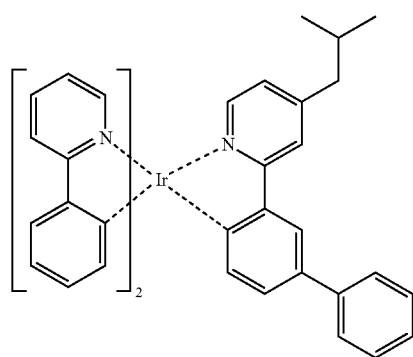
D-44
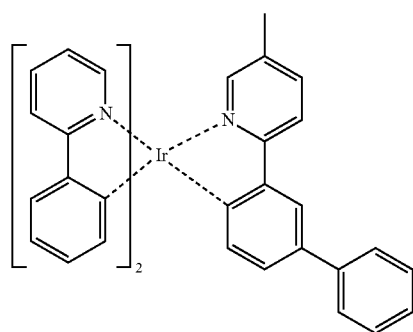
D-45
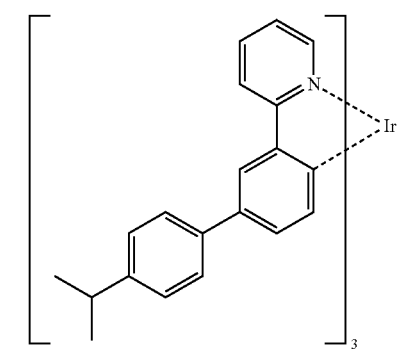
D-46
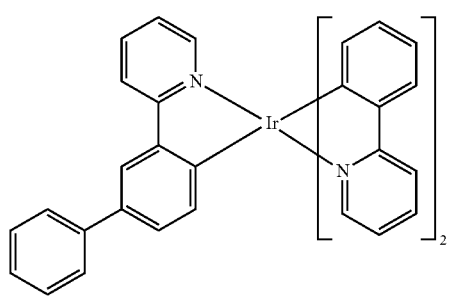
D-47
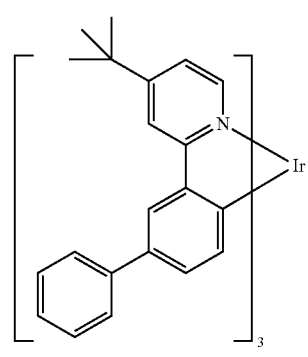
D-48
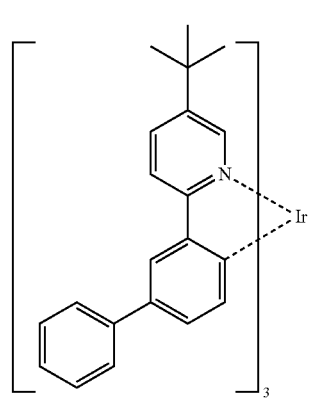
D-49
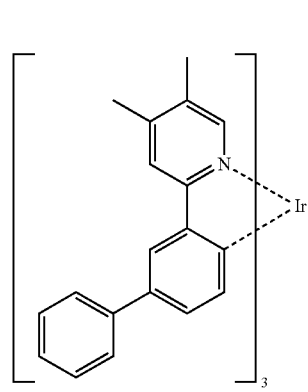
D-50
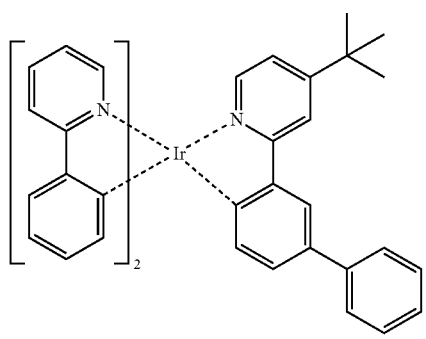
D-51

D-52
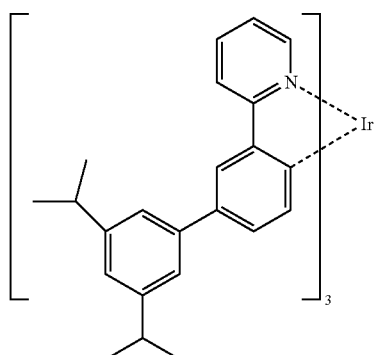
D-53
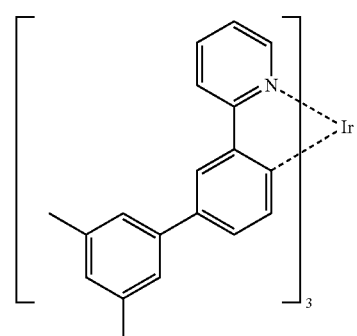
D-54
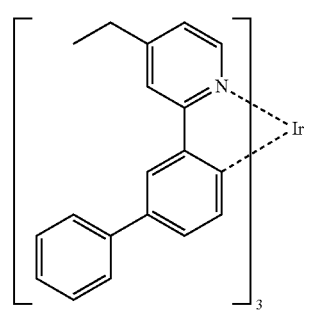
D-55
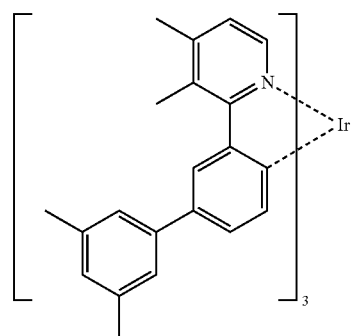
D-56
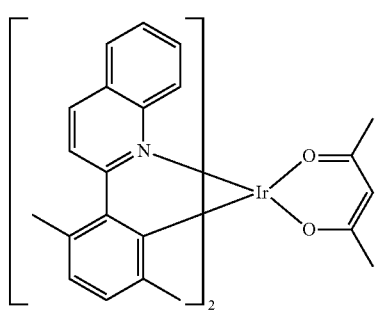
D-57
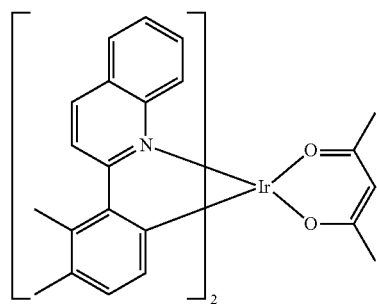
D-58
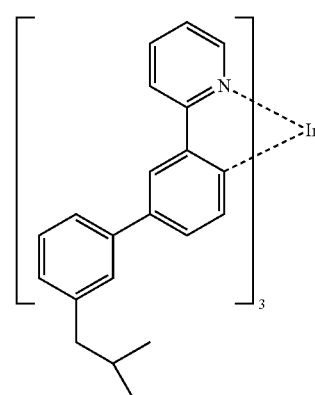
D-59
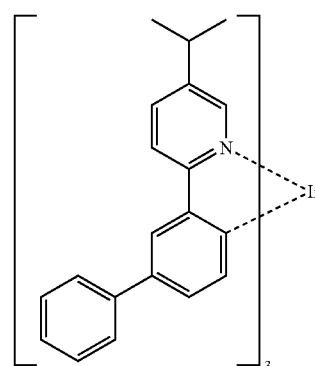
D-60
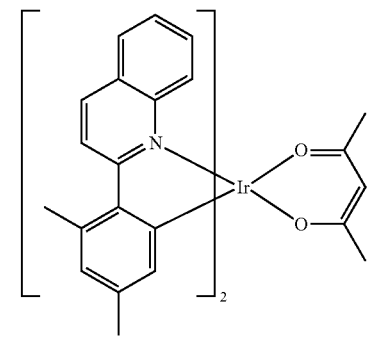
D-61
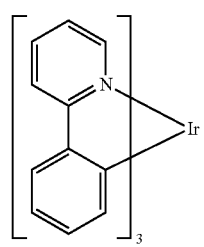

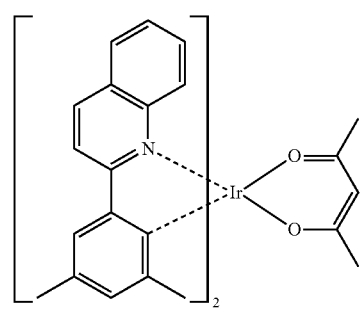
D-62
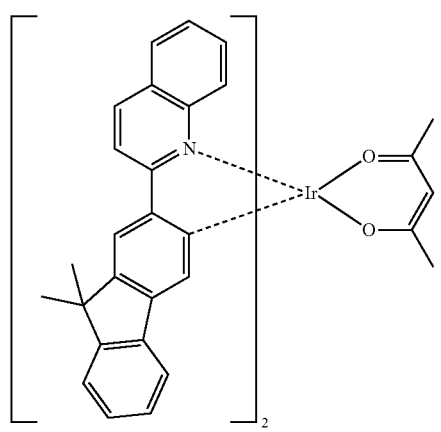
D-63
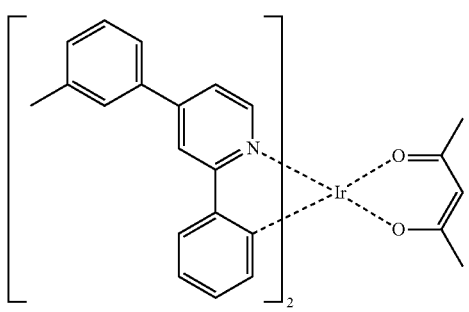
D-64
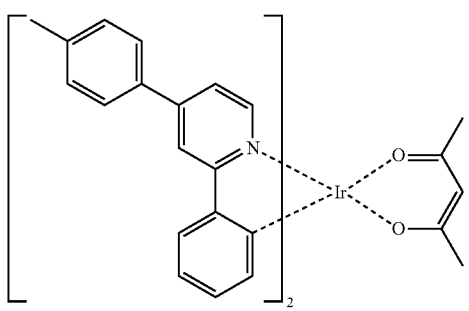
D-65
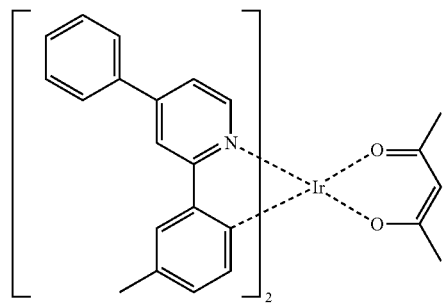
D-66
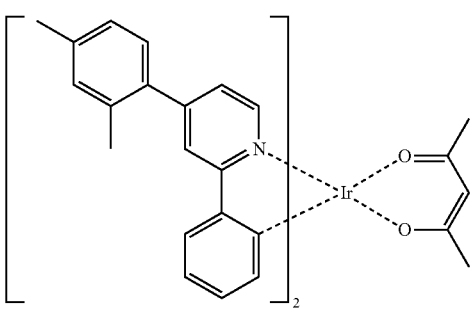
D-67
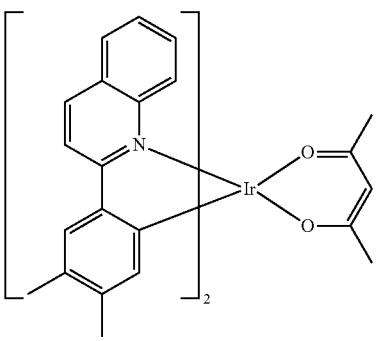
D-68
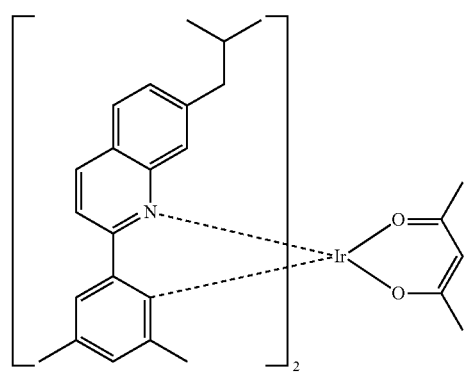
D-69
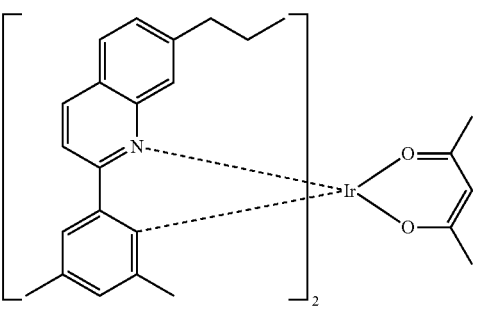
D-70

-continued
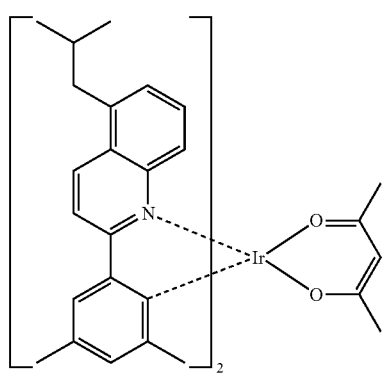
D-71
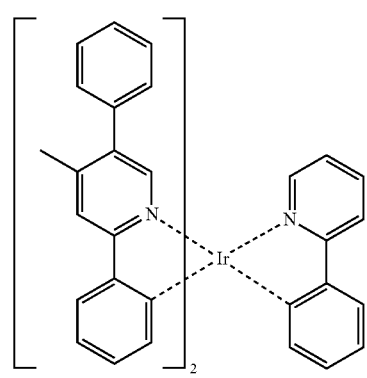
D-75
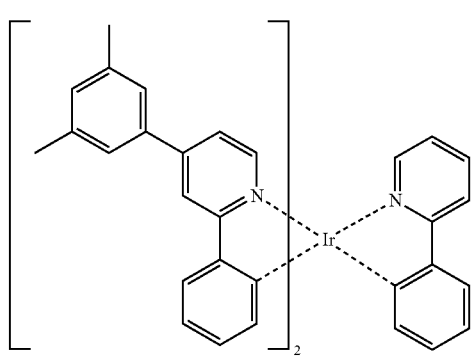
D-72
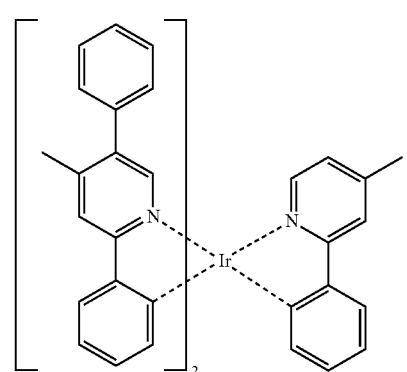
D-76
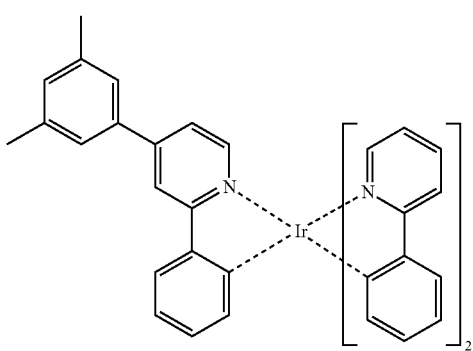
D-73
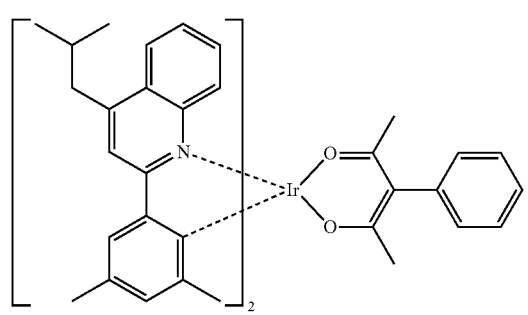
D-77
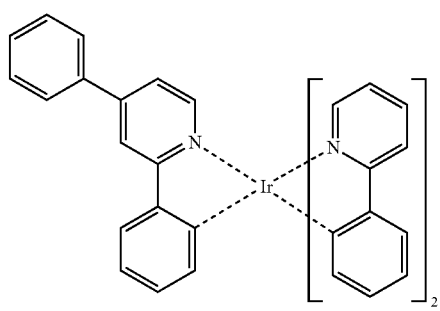
D-74
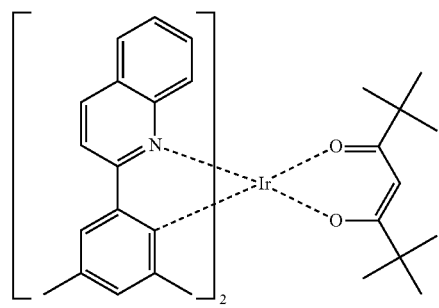
D-78

D-79 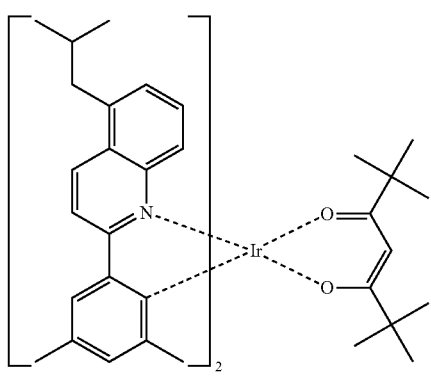
D-80 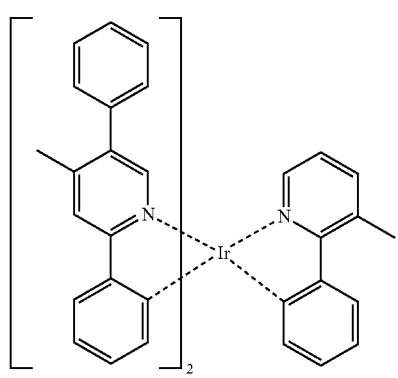
D-81 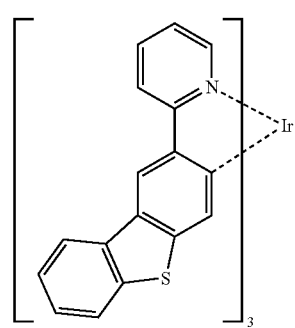
D-82 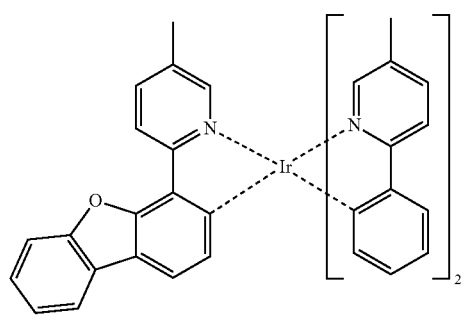
D-83 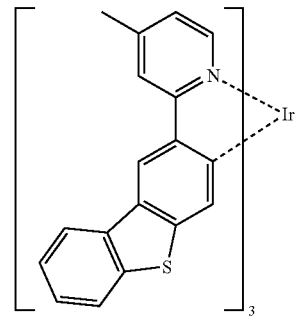
D-84 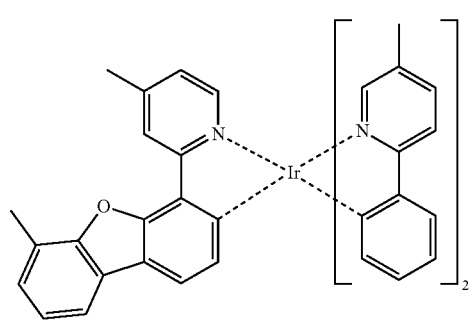
D-85 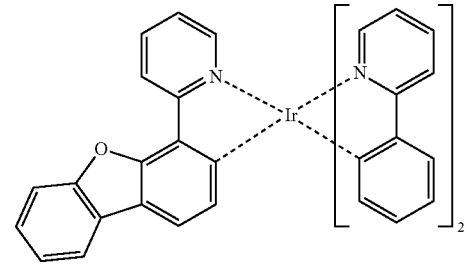
D-86
D-87 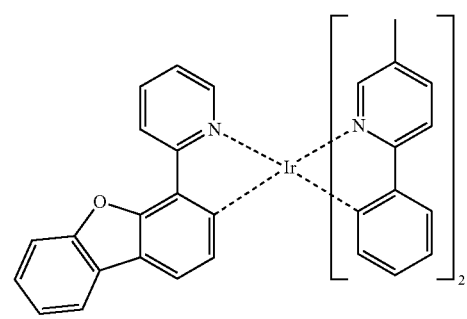

D-88
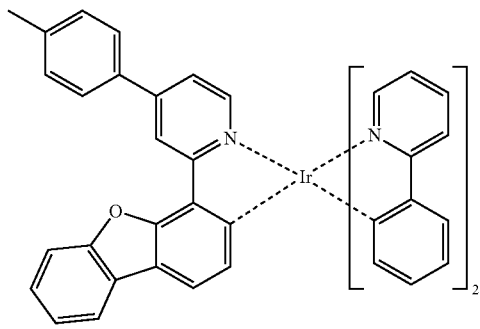
D-89
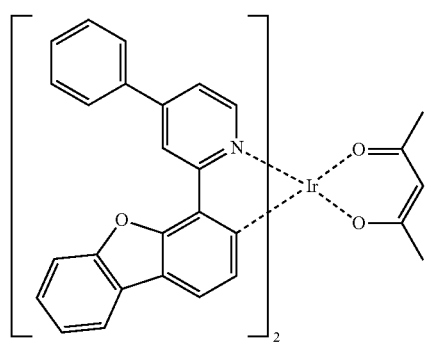
D-90
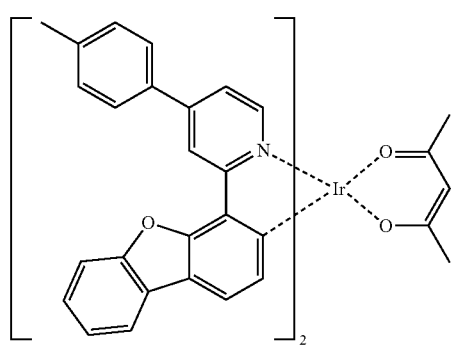
D-91
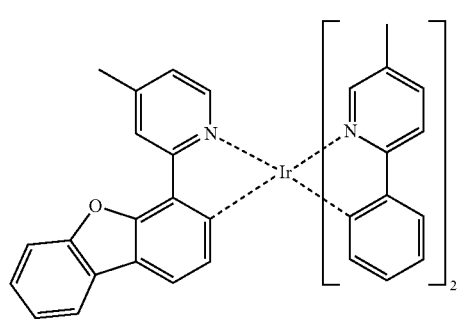
D-92
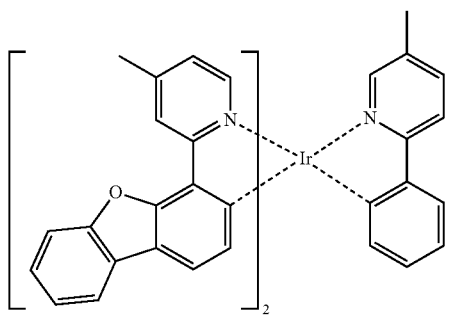
D-93
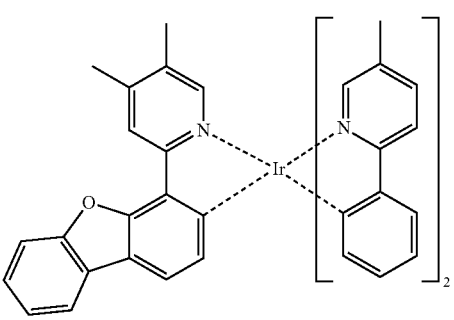
D-94
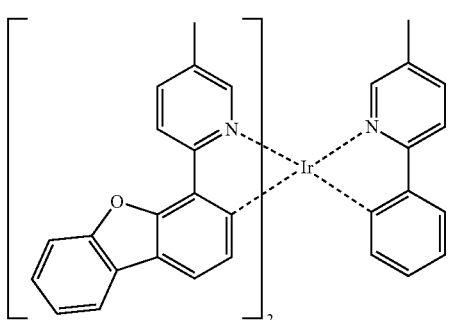
D-95
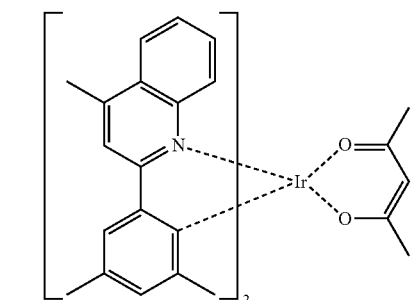
D-96
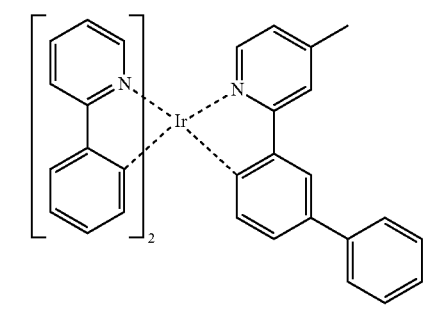

-continued
D-97
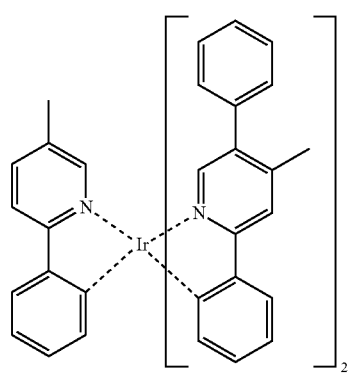
D-98
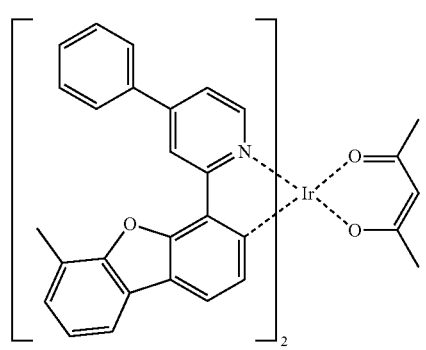
D-99
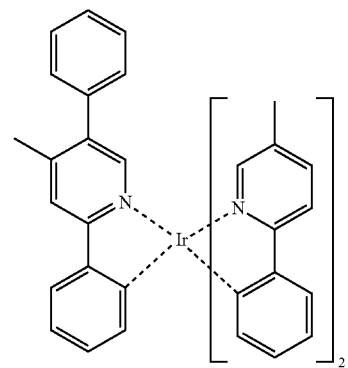
D-100
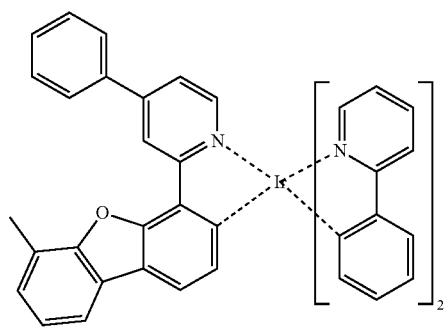
-continued
D-101
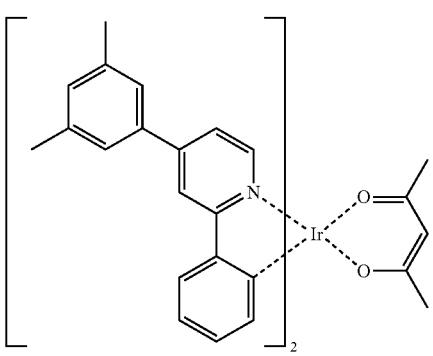
D-102
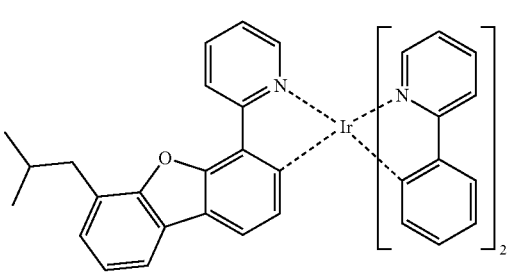
D-103
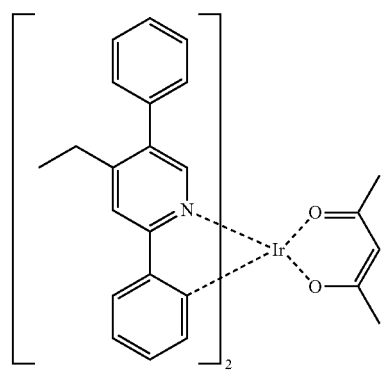
D-104
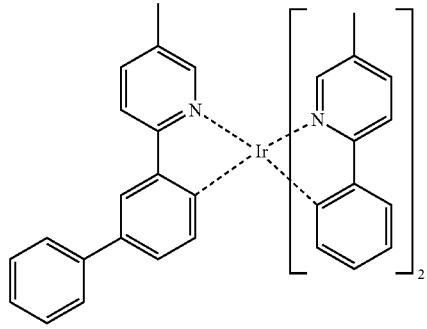

-continued
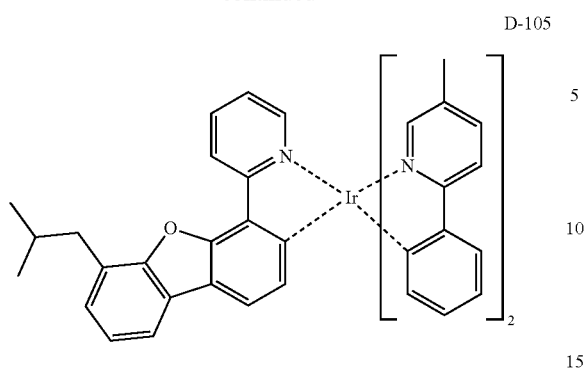
D-105
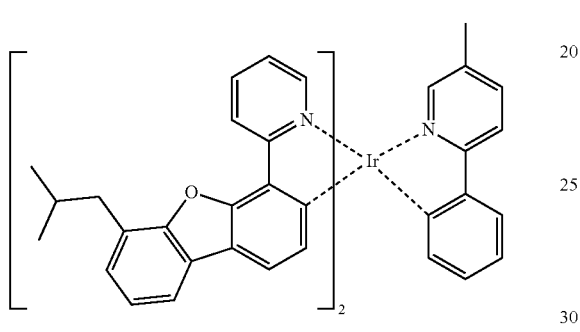
D-106
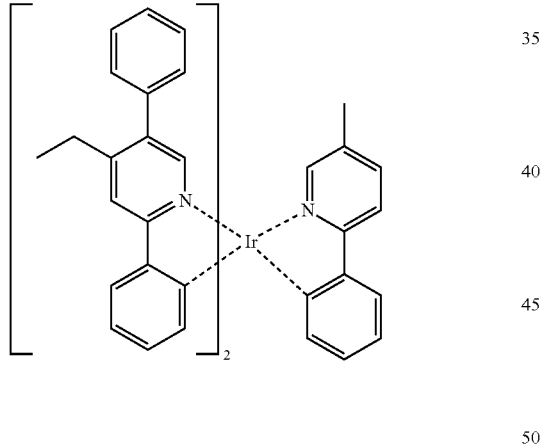
D-107
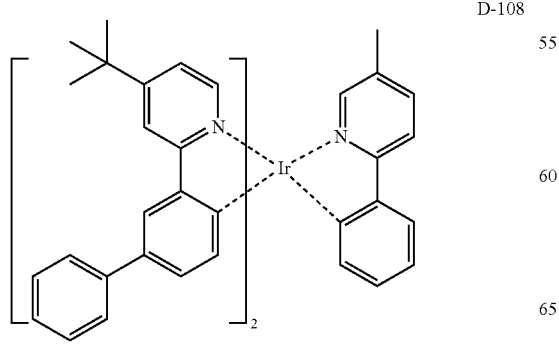
D-108
-continued
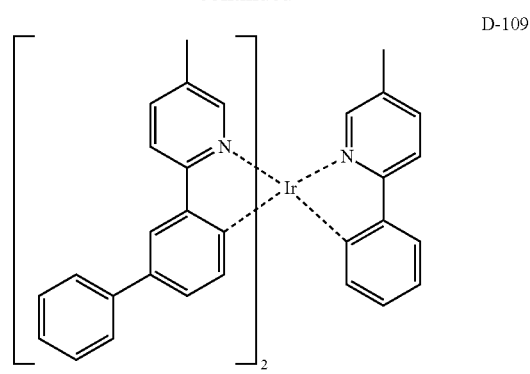
D-109
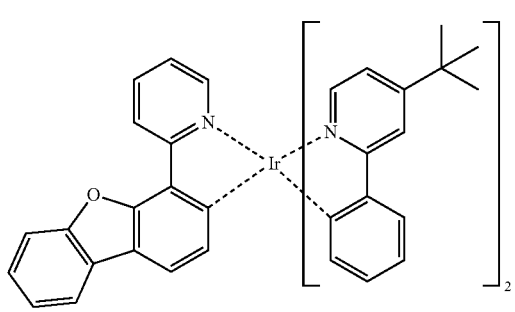
D-110
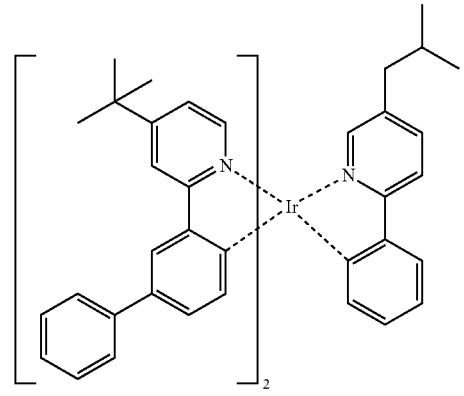
D-111
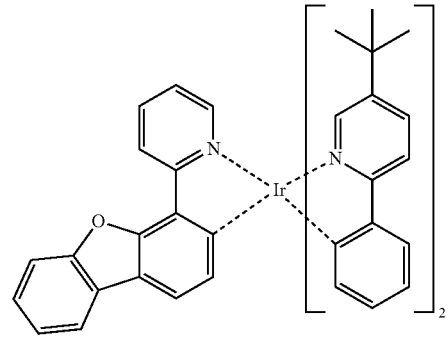
D-112

-continued
D-113
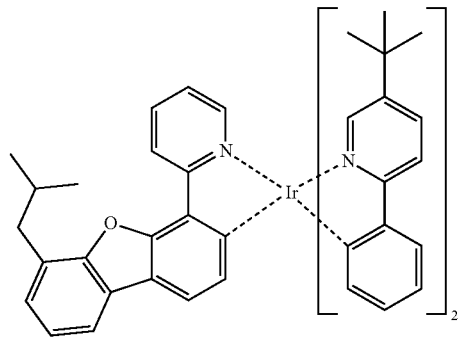
D-114
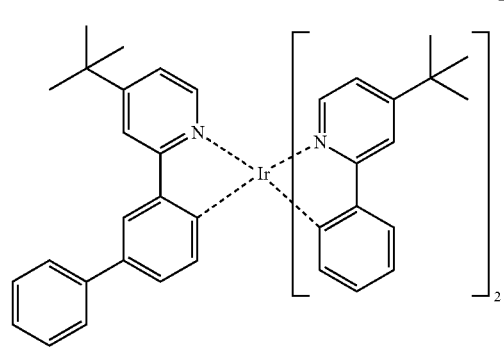
D-115
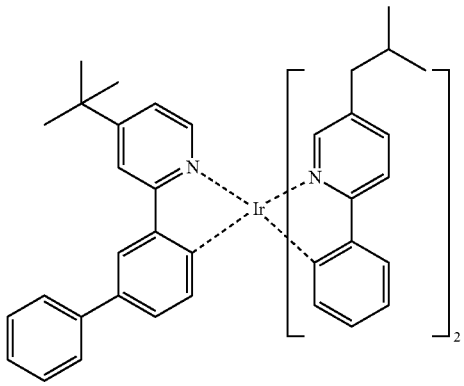
D-116
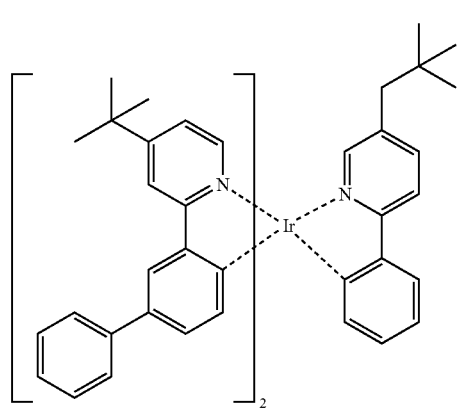
-continued
D-117
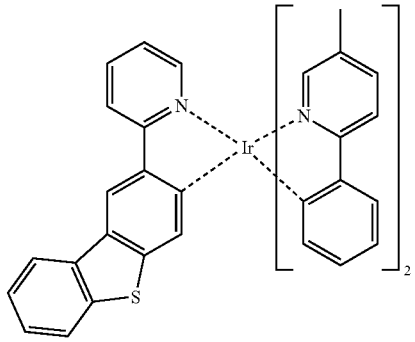
D-118
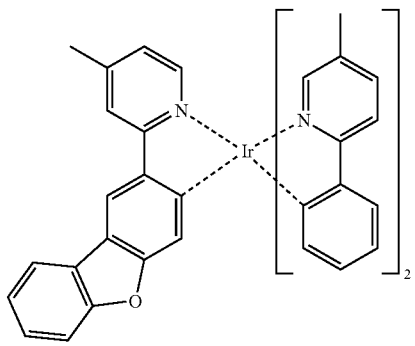
D-119
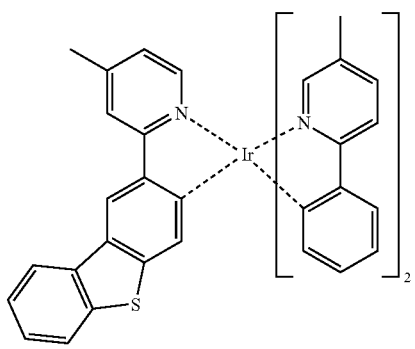
D-120
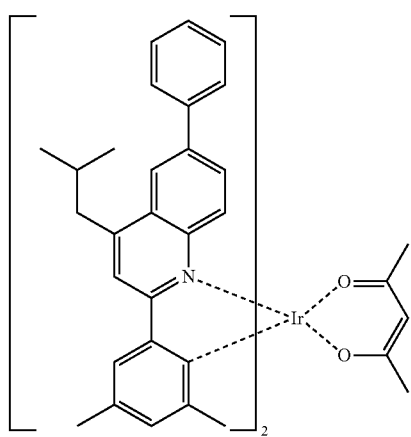

D-121
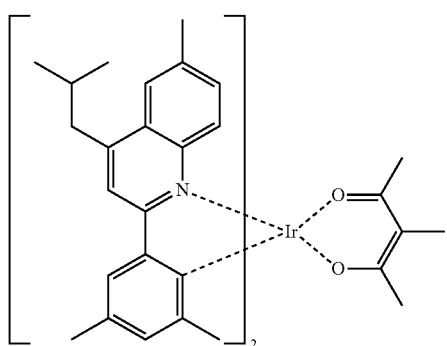
D-122
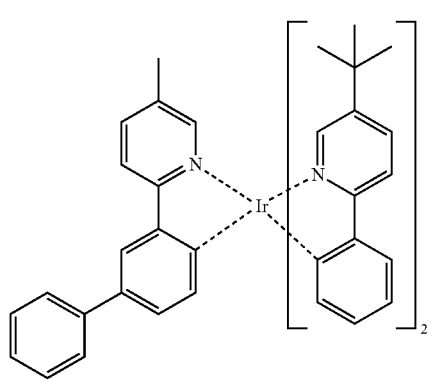
D-123
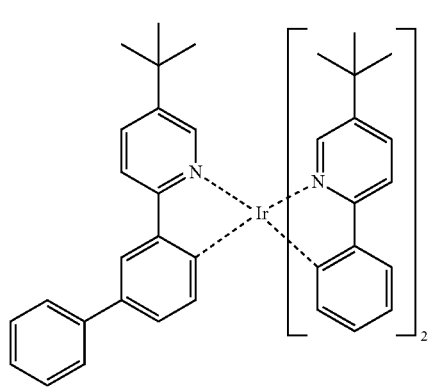
D-124
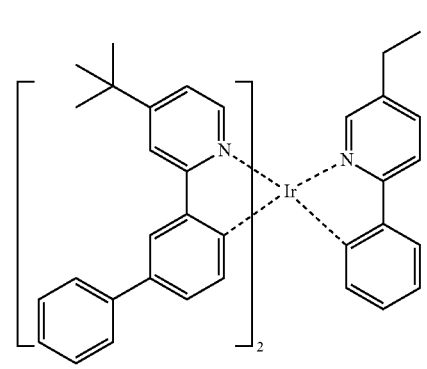
D-125
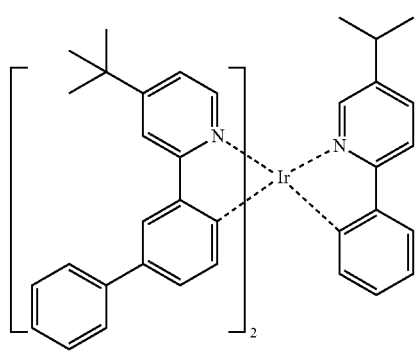
D-126
D-127
D-128
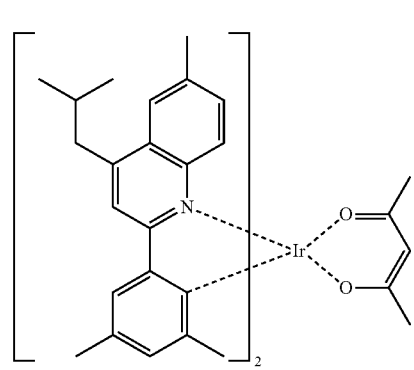

-continued
D-129
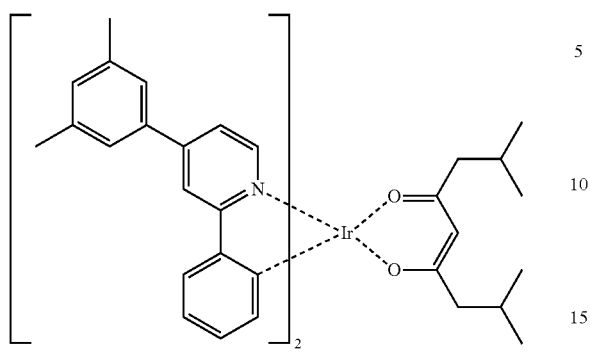
D-130
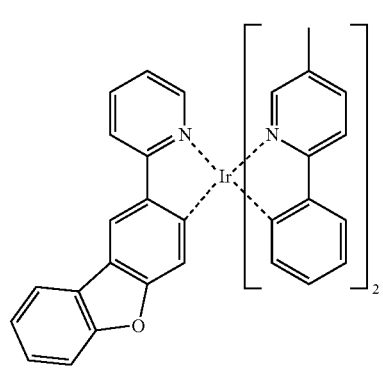
D-131
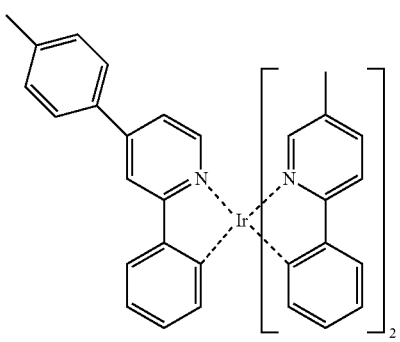
D-132
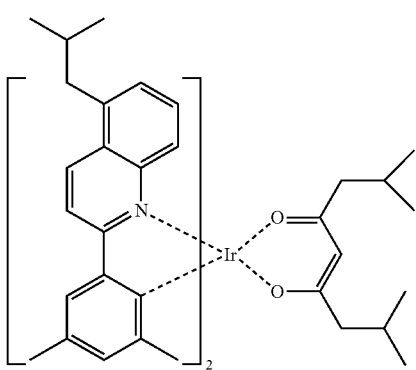
-continued
D-133
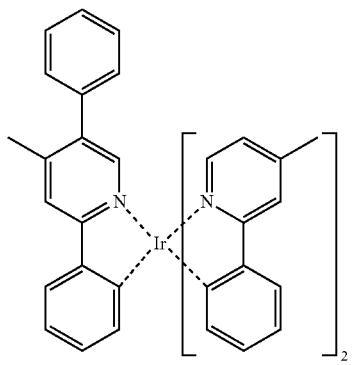
D-134
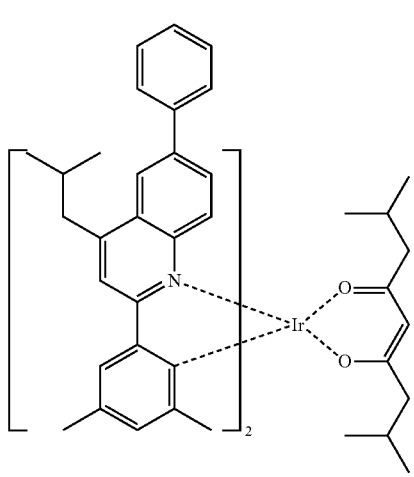
D-135
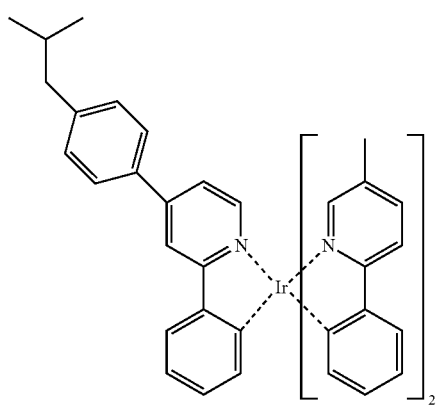
D-136
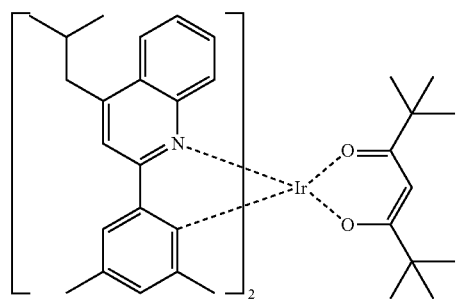

D-137
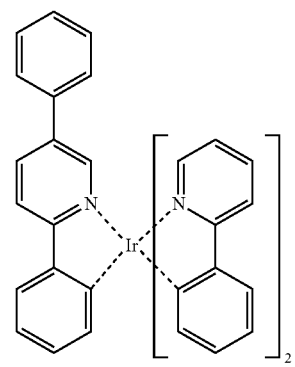
D-140
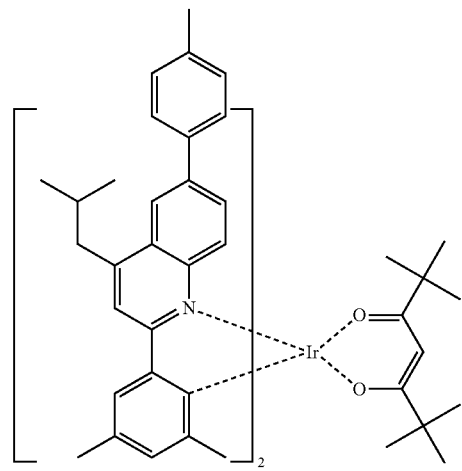
D-138
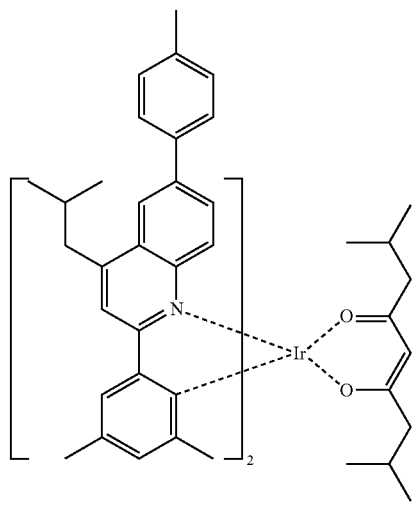
D-141
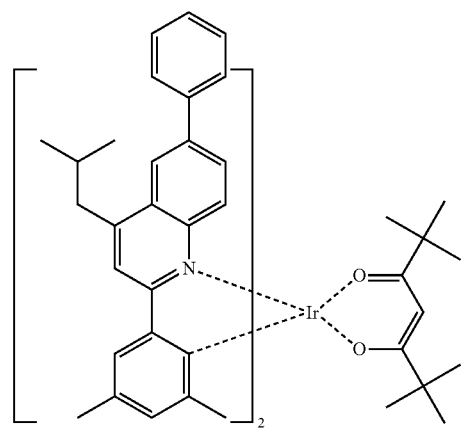
D-142
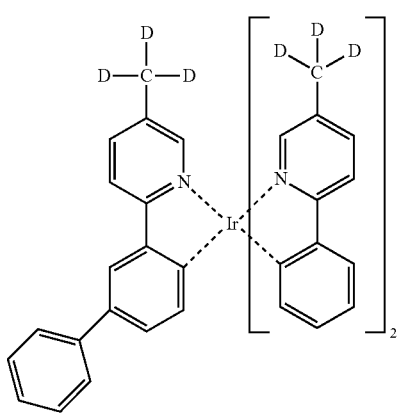
D-139
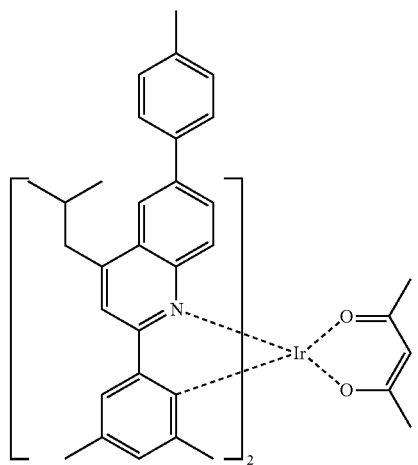
D-143
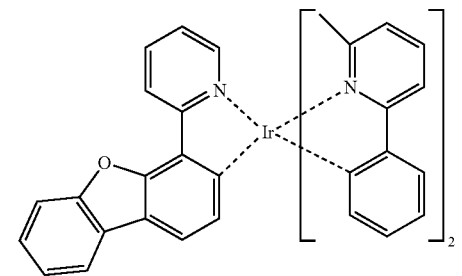

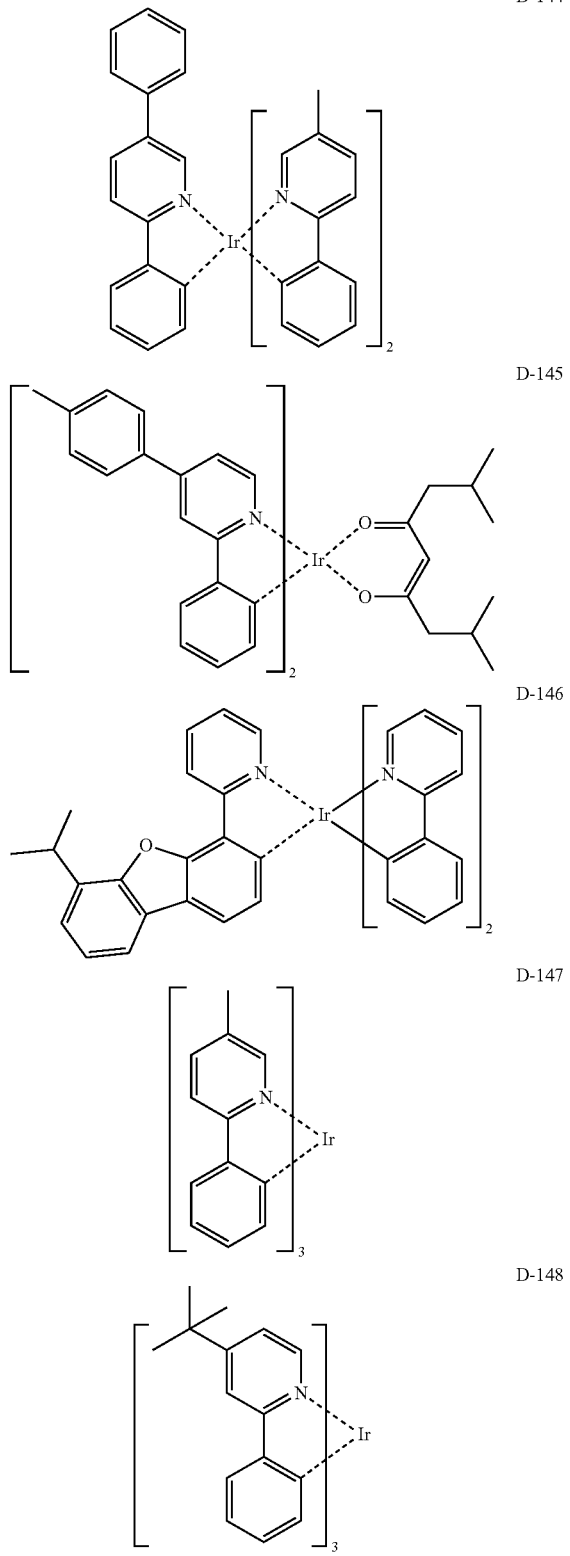

The organic electroluminescent device of the present disclosure may further comprise, in addition to the compound of formula 1, at least one compound selected from the group consisting of arylamine-based compounds and styrylarylamine-based compounds.

In the organic electroluminescent device of the present disclosure, the organic layer may further comprise, in addition to the compound of formula 1, at least one metal selected from the group consisting of metals of Group 1, metals of Group 2, transition metals of the $4^{th}$ period, transition metals of the $5^{th}$ period, lanthanides, and organic metals of the d-transition elements of the Periodic Table, or at least one complex compound comprising the metal. The organic layer may further comprise one or more additional light-emitting layers and a charge generating layer.

In addition, the organic electroluminescent device of the present disclosure may emit white light by further comprising at least one light-emitting layer, which comprises a blue, a red, or a green electroluminescent compound known in the field, besides the compound of the present disclosure. If necessary, it may further comprise a yellow or an orange light-emitting layer.

In the organic electroluminescent device of the present disclosure, preferably, at least one layer (hereinafter, "a surface layer") may be placed on an inner surface(s) of one or both electrode(s), selected from a chalcogenide layer, a metal halide layer, and a metal oxide layer. Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

In the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to an electroluminescent medium. Furthermore, the hole transport compound is oxidized to a cation, and thus it becomes easier to inject and transport holes from the mixed region to the electroluminescent medium. Preferably, the oxidative dopant includes various Lewis acids and acceptor compounds, and the reductive dopant includes alkali metals, alkali metal compounds, alkaline earth metals, rare-earth metals, and mixtures thereof. A reductive dopant layer may be employed as a charge generating layer to prepare an electroluminescent device having two or more light-emitting layers and emitting white light.

In order to form each layer of the organic electroluminescent device of the present disclosure, dry film-forming methods such as vacuum evaporation, sputtering, plasma, and ion plating methods, or wet film-forming methods such as ink jet printing, nozzle printing, slot coating, spin coating, dip coating, and flow coating methods can be used.

When using a wet film-forming method, a thin film can be formed by dissolving or diffusing materials forming each layer into any suitable solvent such as ethanol, chloroform, tetrahydrofuran, dioxane, etc. The solvent can be any solvent where the materials forming each layer can be dissolved or diffused, and where there are no problems in film-formation capability.

Hereinafter, the organic electroluminescent compounds of the present disclosure, the preparation method thereof, and the properties of the device comprising the compounds will be explained in detail with reference to the representative compounds of the present disclosure.

Example 1: Preparation of Compound C-24

2) Preparation of Compound 1-2

After introducing compound 1-1 (45.6 g, 130 mmol), (methoxymethyl)triphenylphosphonium chloride (74.3 g, 217 mmol), and tetrahydrofuran (1500 mL) into a reaction vessel, the mixture was stirred for 5 minutes. Potassium

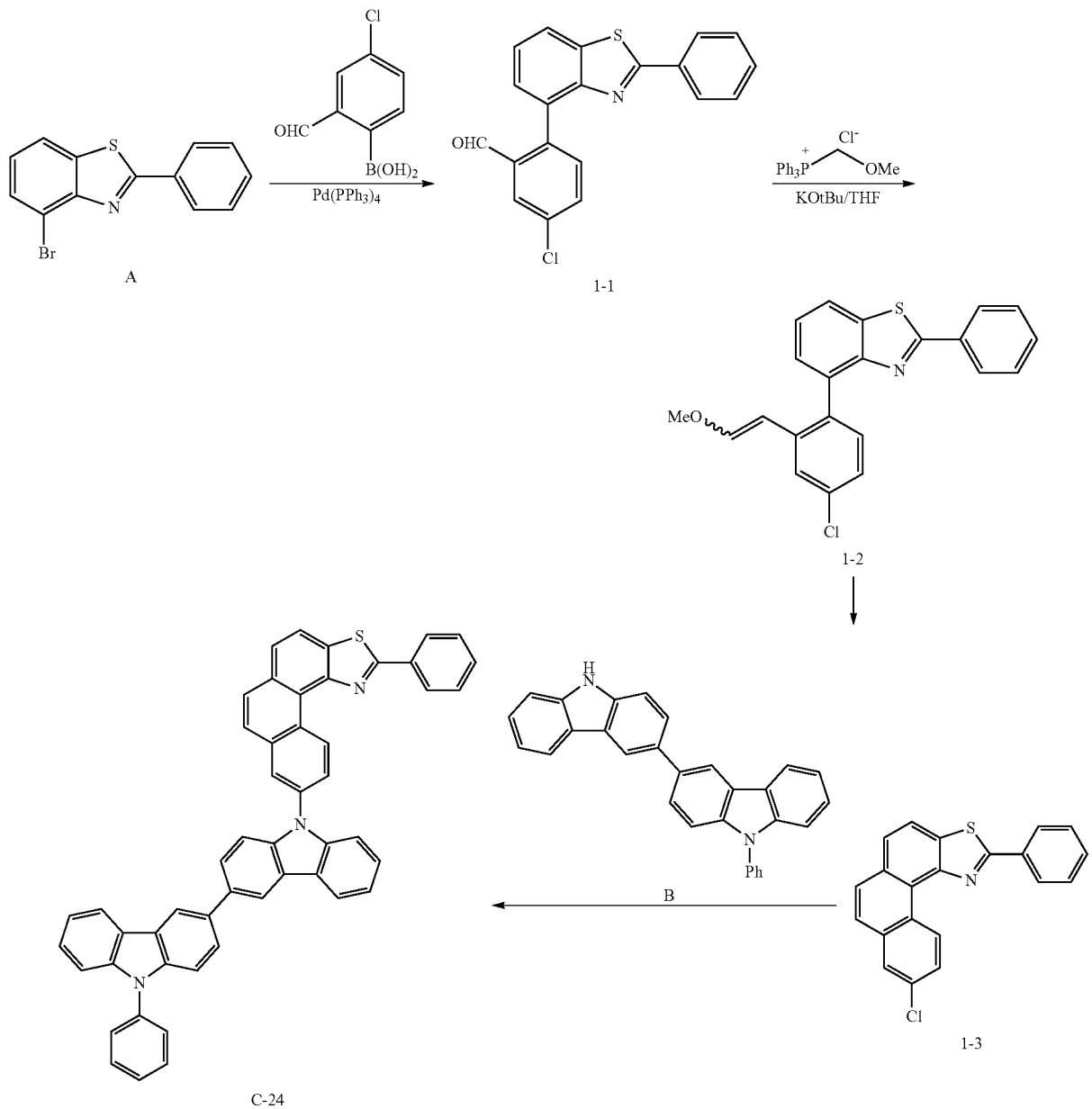

1) Preparation of Compound 1-1

After introducing compound A (CAS: 1044146-16-8, 36 g, 124 mmol), 4-chloro-2-formylbenzene boronic acid (25.2 g, 136 mmol), tetrakis(triphenylphosphine)palladium (5.7 g, 5.0 mmol), sodium carbonate (33 g, 150 mmol), toluene (600 mL), ethanol (150 mL), and distilled water (150 mL) into a reaction vessel, the mixture was stirred for 3 hours at 140° C. After completing the reaction, the precipitated solid was washed with distilled water and methanol. The obtained compound 1-1 was used in the next reaction without any further purification.

tert-butoxide (1M in THF, 220 mL) was then slowly added dropwise to the mixture at 0° C. The temperature of the mixture was slowly raised, and the mixture was stirred at room temperature for 3 hours. After completing the reaction by adding distilled water to the reaction solution, an organic layer was extracted with ethyl acetate. The extracted organic layer was dried with magnesium sulfate, and the solvent was removed therefrom using a rotary evaporator. Thereafter, the remaining product was purified by column chromatography to obtain compound 1-2 (48 g, 97%).

3) Preparation of Compound 1-3

After introducing compound 1-2 (44.8 g, 119 mmol), Eaton's reagent (4.5 mL), and chlorobenzene (600 mL) into a reaction vessel, the mixture was refluxed for 2 hours. After completing the reaction, the mixure was cooled to room temperature, and an organic layer was extracted with methylene chloride (MC). After drying the extracted organic layer with magnesium sulfate, the solvent was removed by using a rotary evaporator. Thereafter, the obtained product was purified by column chromatography to obtain compound 1-3 (36.3 g, 89%).

4) Preparation of Compound C-24

After introducing compound 1-3 (8 g, 23 mmol), compound B (CAS: 1060735-14-9, 9.5 g, 23 mmol), tris(dibenzylidyneacetone)dipalladium (1 g, 1.16 mmol), 2-dicyclohexylphosphino-2',6'-dimethoxybiphenyl (s-phos) (0.95 g, 2.31 mmol), sodium tert-butoxide (4.5 g, 46.3 mmol), and o-xylene (150 mL) into a reaction vessel, the mixture was stirred for 3 hours at 170° C. After completing the reaction, the mixture was added dropwise to methanol, and the obtained solid was filtered. The obtained solid was purified by column chromatography to obtain compound C-24 (8.7 g, 68%).

Example 2: Preparation of Compound C-1

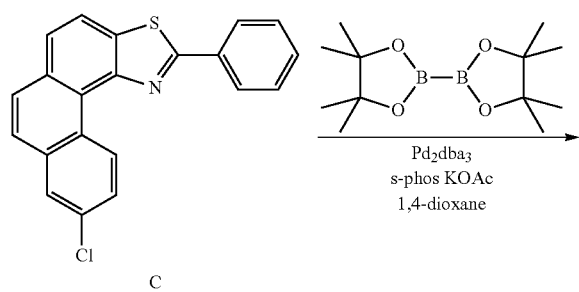

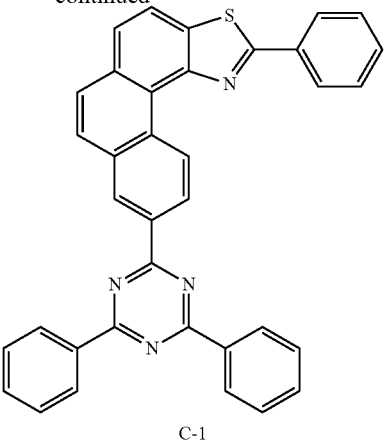

C-1

1) Preparation of Compound 2-1

After introducing compound C (10 g, 29 mmol), bis (pinacolato)diborane (8.8 g, 34.8 mmol), tris(dibenzylidyneacetone)dipalladium (1.3 g, 1.45 mmol), 2-dicyclohexylphosphino-2',6'-dimethoxybiphenyl (s-phos) (1.2 g, 2.9 mmol), potassium acetate (8.5 g, 87 mmol), and 1,4-dioxane (150 mL) into a reaction vessel, the mixture was stirred for 3 hours at 140° C. After completing the reaction, the mixture was cooled to room temperature, and an organic layer was extracted with ethyl acetate. After drying the extracted organic layer with magnesium sulfate, the solvent was removed by using a rotary evaporator. Thereafter, the obtained product was purified by column chromatography to obtain compound 2-1 (10.4 g, 82%).

2) Preparation of Compound C-1

After introducing compound 2-1 (10 g, 23.8 mmol), 2-chloro-4,6-diphenyltriazine (CAS: 3842-55-5, 6.4 g, 23.8 mmol), tris(dibenzylidyneacetone)dipalladium (1 g, 1.16 mmol), 2-dicyclohexylphosphino-2',6'-dimethoxybiphenyl (s-phos) (1 g, 2.31 mmol), sodium tert-butoxide (4.5 g, 46.3 mmol), and o-xylene (150 mL) into a reaction vessel, the mixture was stirred for 3 hours at 170° C. After completing the reaction, the mixture was added dropwise to methanol, and the obtained solid was filtered. The obtained solid was purified by column chromatography to obtain compound C-1 (8.2 g, 55%).

Example 3: Preparation of Compound C-17

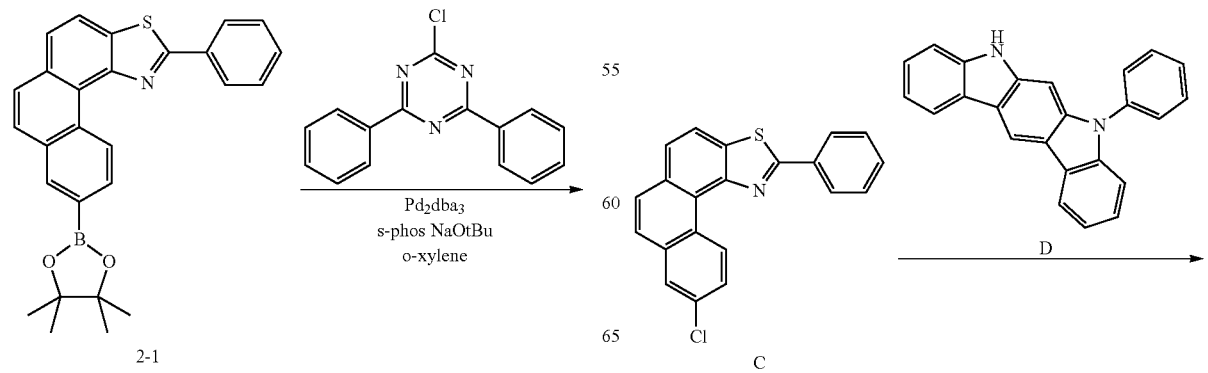

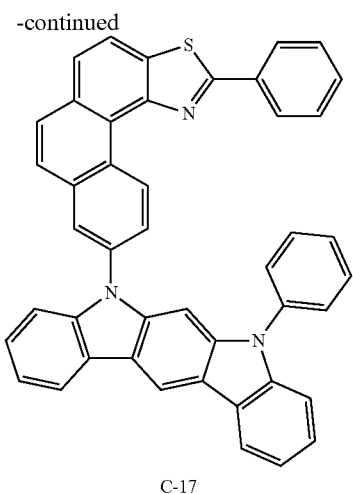

C-17

After introducing compound C (8 g, 23.1 mmol), compound D (CAS: 1448296-00-1, 7.7 g, 23.1 mmol), tetrakis(triphenylphosphine)palladium (1.4 g, 1.19 mmol), potassium carbonate (8.2 g, 60 mmol), toluene (90 mL), ethanol (30 mL), and distilled water (30 mL) into a reaction vessel, the mixture was stirred for 3 hours at 140° C. After completing the reaction, the precipitated solid was washed with distilled water and methanol. The obtained compound was purified by column chromatography to obtain compound C-17 (8.7 g, 77%).

Example 4: Preparation of Compound C-39

1) Preparation of Compound 3-1

After introducing compound E (CAS: 913835-76-4, 40 g, 212.7 mmol), benzaldehyde (27 g, 255.29 mmol), sodium cyanide (10.4 g, 212.7 mmol), and N,N-dimethylformamide (DMF) (1000 mL) into a reaction vessel, the mixture was stirred for 3 hours at 100° C. The reaction solution cooled to room temperature was extracted with ethyl acetate. The obtained compound 3-1 was used in the next reaction without any further purification.

2) Preparation of Compound 3-2

After introducing compound 3-1 (35 g, 128 mmol), 4-chloro-2-formylbenzene boronic acid (26 g, 141 mmol), tetrakis(triphenylphosphine)palladium (6 g, 5.1 mmol), sodium carbonate (34 g, 320 mmol), toluene (600 mL), ethanol (150 mL), and distilled water (150 mL) into a reaction vessel, the mixture was stirred for 3 hours at 140° C. After completing the reaction, the precipitated solid was washed with distilled water and methanol. The obtained compound 3-2 was used in the next reaction without further purification.

3) Preparation of Compound 3-3

After introducing compound 3-2 (19 g, 56.9 mmol), (methoxymethyl)triphenylphosphonium chloride (29.3 g, 85.4 mmol), and tetrahydrofuran (500 mL) into a reaction vessel, the mixture was stirred for 5 minutes. Potassium tert-butoxide (1M in THF, 85 mL) was then slowly added dropwise to the mixture at 0° C. The temperature of the mixture was slowly raised, and the mixture was stirred at room temperature for 3 hours. After completing the reaction by adding distilled water to the reaction solution, an organic layer was extracted with ethyl acetate. The obtained organic layer was dried with magnesium sulfate, and the solvent was

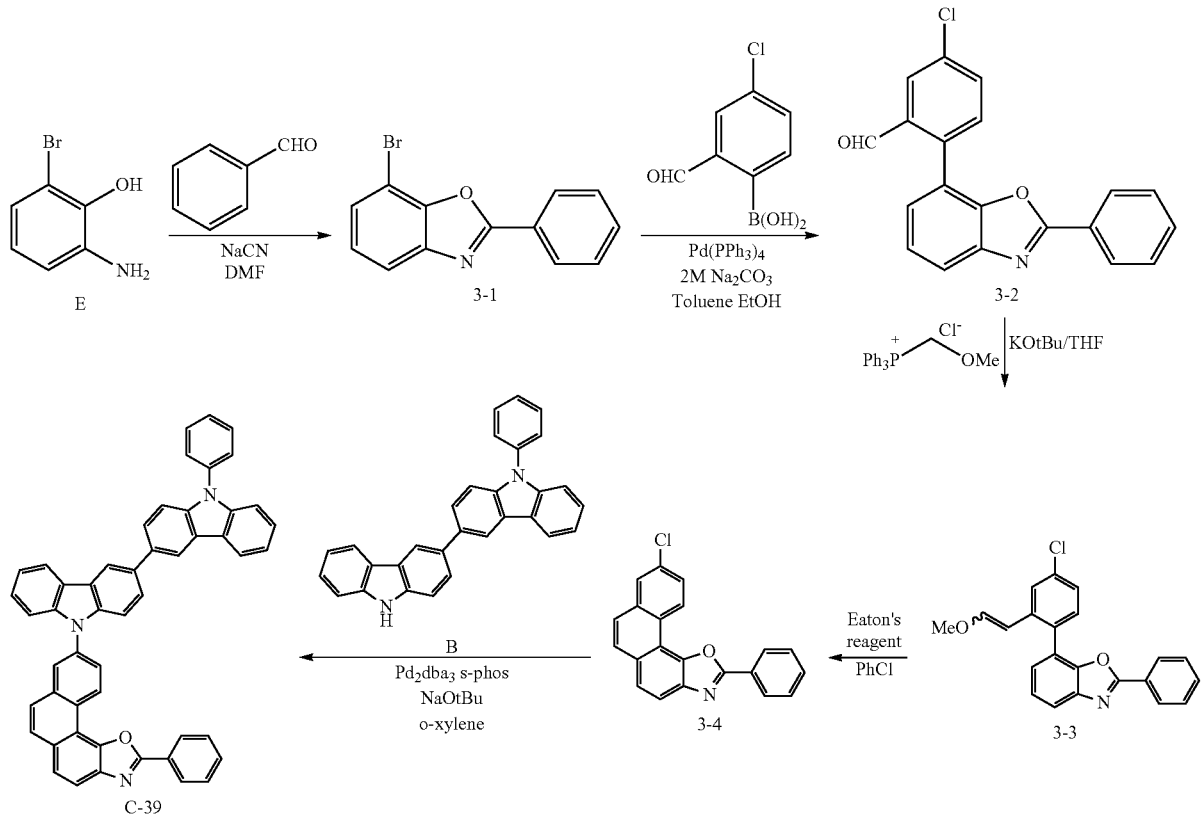

removed therefrom using a rotary evaporator. Thereafter, the remaining product was purified by column chromatography to obtain compound 3-3 (16.4 g, 80%).

4) Preparation of Compound 3-4

After introducing compound 3-3 (14.4 g, 39.8 mmol), Eaton's reagent (1.4 mL), and chlorobenzene (200 mL) into a reaction vessel, the mixture was refluxed for 2 hours. After completing the reaction, the mixure was cooled to room temperature, and an organic layer was extracted with methylene chloride (MC). After drying the extracted organic layer with magnesium sulfate, the solvent was removed by using a rotary evaporator. Thereafter, the obtained product was purified by column chromatography to obtain compound 3-4 (11.1 g, 79%).

5) Preparation of Compound C-39

After introducing compound 3-4 (4 g, 12.1 mmol), compound B (CAS: 1060735-14-9, 4.9 g, 12.1 mmol), tris(dibenzylidyneacetone)dipalladium (0.5 g, 0.61 mmol), 2-dicyclohexylphosphino-2',6'-dimethoxybiphenyl (s-phos) (0.5 g, 1.21 mmol), sodium tert-butoxide (2.33 g, 24.3 mmol), and o-xylene (100 mL) into a reaction vessel, the mixture was stirred for 3 hours at 170° C. After completing the reaction, the mixture was added dropwise to methanol, and the obtained solid was filtered. The obtained solid was purified by column chromatography to obtain compound C-39 (8.7 g, 47%).

Example 5: Preparation of Compound C-49

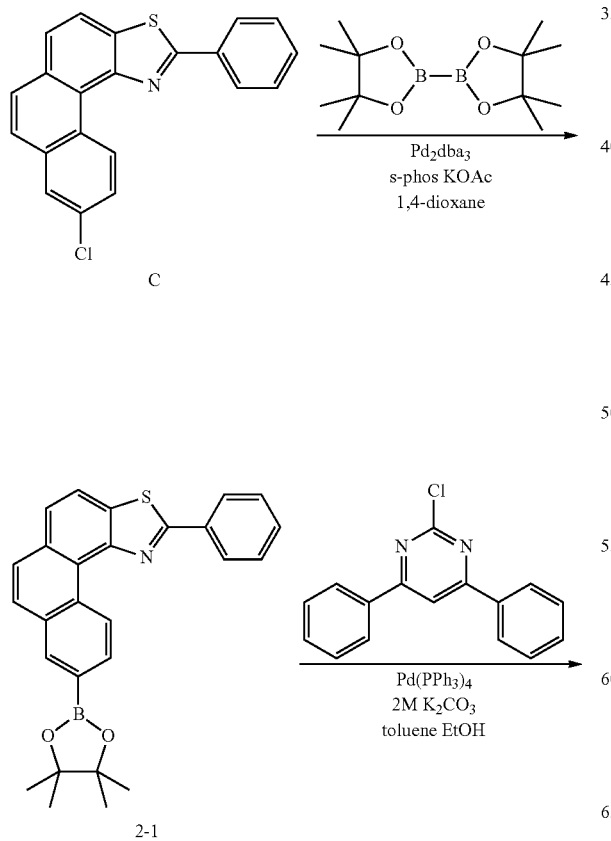

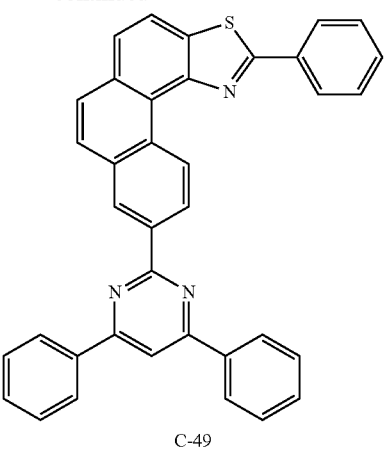

C-49

1) Preparation of Compound 2-1

Compound 2-1 was prepared in the same manner as described in Example 2.

2) Preparation of Compound C-49

After introducing compound 2-1 (4.5 g, 10 mmol), 2-chloro-4,6-diphenylpyrimidine (CAS: 2915-16-4, 2.7 g, 10 mmol), tetrakis(triphenylphosphine)palladium (0.47 g, 0.4 mmol), potassium carbonate (3.6 g, 26 mmol), toluene (50 mL), ethanol (13 mL), and distilled water (13 mL) into a reaction vessel, the mixture was stirred for 4 hours at 120° C. After completing the reaction, the mixture was added dropwise to methanol, and the obtained solid was filtered. The obtained solid was purified by column chromatography to obtain compound C-49 (4.5 g, 73%).

Example 6: Preparation of Compound C-75

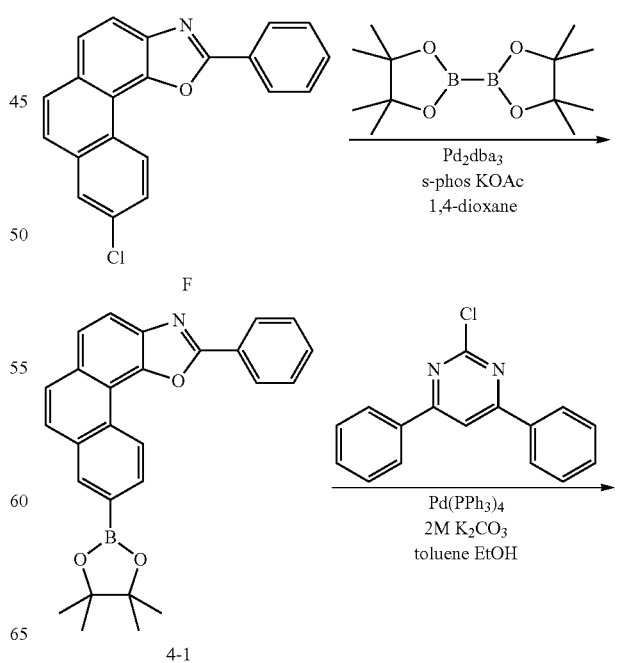

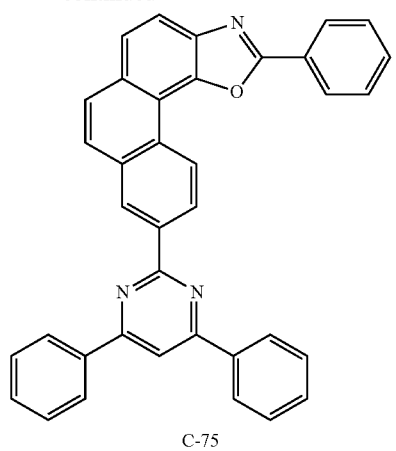

C-75

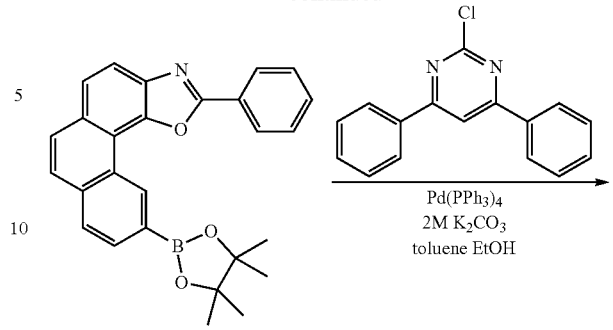

5-1

1) Preparation of Compound 4-1

After introducing compound F (7.2 g, 21.8 mmol), bis(pinacolato)diborane (6.6 g, 26.2 mmol), tris(dibenzylidyneacetone)dipalladium (1.0 g, 1.1 mmol), 2-dicyclohexylphosphino-2',6'-dimethoxybiphenyl (s-phos) (0.89 g, 2.2 mmol), potassium acetate (6.4 g, 65 mmol), and 1,4-dioxane (150 mL) into a reaction vessel, the mixture was stirred for 3 hours at 140° C. After completing the reaction, the mixture was cooled to room temperature, and an organic layer was extracted with ethyl acetate. After drying the extracted organic layer with magnesium sulfate, the solvent was removed by using a rotary evaporator. Thereafter, the obtained product was purified by column chromatography to obtain compound 4-1 (5.2 g, 57%).

2) Preparation of Compound C-75

After introducing compound 4-1 (5.2 g, 12.3 mmol), 2-chloro-4,6-diphenylpyrimidine (CAS: 2915-16-4, 3.3 g, 12.3 mmol), tetrakis(triphenylphosphine)palladium (0.71 g, 0.62 mmol), potassium carbonate (4.2 g, 30 mmol), toluene (60 mL), ethanol (20 mL), and distilled water (20 mL) into a reaction vessel, the mixture was stirred for 4 hours at 120° C. After completing the reaction, the mixture was added dropwise to methanol, and the obtained solid was filtered. The obtained solid was purified by column chromatography and recrystallization to obtain compound C-75 (5.3 g, 82%).

Example 7: Preparation of Compound C-87

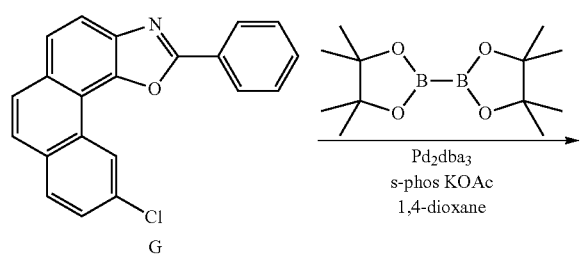

G

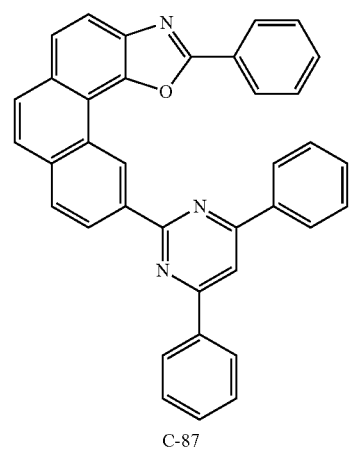

C-87

1) Preparation of Compound G

Compound G was prepared in the same manner as the preparation of compound 3-2 described in Example 4, except for using 5-chloro-2-formylboronic acid instead of 4-chloro-2-formylbenzene boronic acid.

2) Preparation of Compound 5-1

After introducing compound G (15 g, 45.5 mmol), bis(pinacolato)diborane (13.9 g, 54.6 mmol), tris(dibenzylidyneacetone)dipalladium (1.6 g, 1.8 mmol), 2-dicyclohexylphosphino-2',6'-dimethoxybiphenyl (s-phos) (0.9 g, 3.64 mmol), potassium acetate (13 g, 136 mmol), and 1,4-dioxane (350 mL) into a reaction vessel, the mixture was stirred for 3 hours at 140° C. After completing the reaction, the mixure was cooled to room temperature, and an organic layer was extracted with ethyl acetate. After drying the extracted organic layer with magnesium sulfate, the solvent was removed by using a rotary evaporator. Thereafter, the obtained product was purified by column chromatography to obtain compound 5-1 (20 g, 99%).

3) Preparation of Compound C-87

After introducing compound 5-1 (10 g, 22.7 mmol), 2-chloro-4,6-diphenylpyrimidine (CAS: 2915-16-4, 5.5 g, 20.6 mmol), tetrakis(triphenylphosphine)palladium (1.2 g, 1.0 mmol), potassium carbonate (7.1 g, 56 mmol), toluene (90 mL), ethanol (30 mL), and distilled water (30 mL) into a reaction vessel, the mixture was stirred for 4 hours at 120° C. After completing the reaction, the mixture was added dropwise to methanol, and the obtained solid was filtered. The obtained solid was purified by column chromatography and recrystallization to obtain compound C-87 (5.5 g, 51%).

Example 8: Preparation of Compound C-88

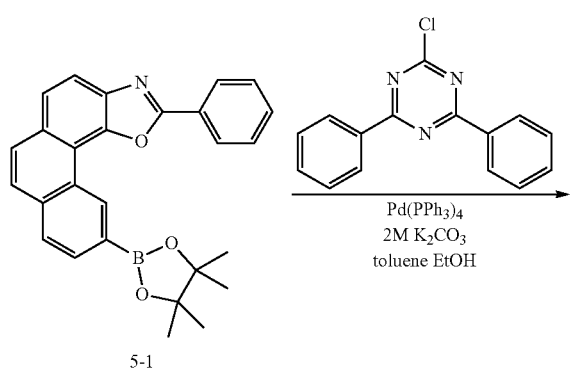

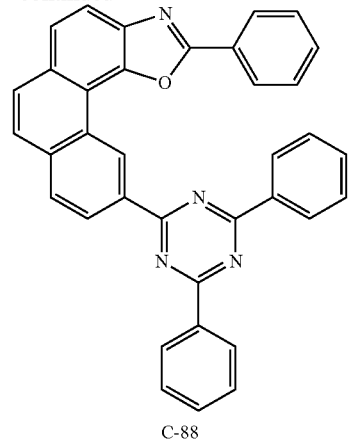

C-88

After introducing compound 5-1 (10 g, 23.7 mmol), 2-chloro-4,6-diphenyltriazine (CAS: 3842-55-5, 5.8 g, 21.6 mmol), tetrakis(triphenylphosphine)palladium (1.2 g, 1.0 mmol), potassium carbonate (7.5 g, 59 mmol), toluene (90 mL), ethanol (30 mL), and distilled water (30 mL) into a reaction vessel, the mixture was stirred for 4 hours at 120° C. After completing the reaction, the mixture was added dropwise to methanol, and the obtained solid was filtered. The obtained solid was purified by column chromatography and recrystallization to obtain compound C-88 (5.7 g, 50%).

Example 9: Preparation of Compound C-45

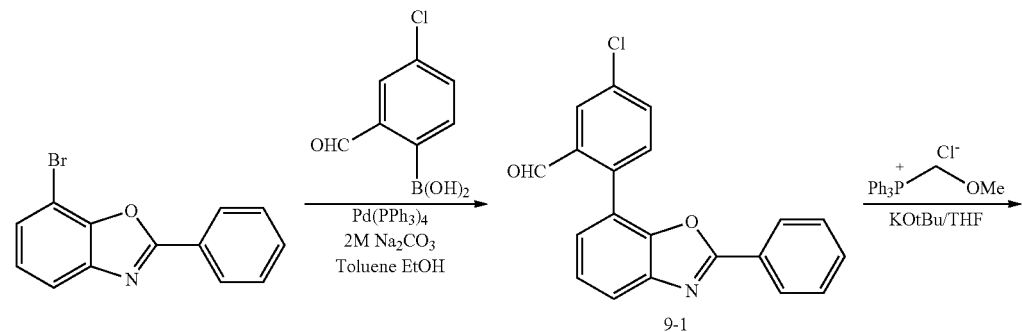

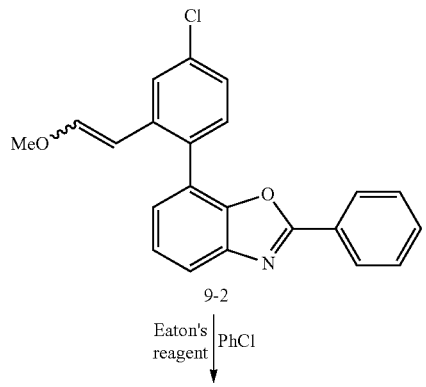

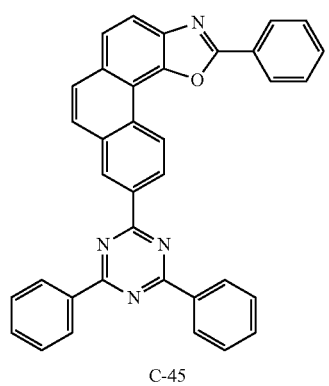
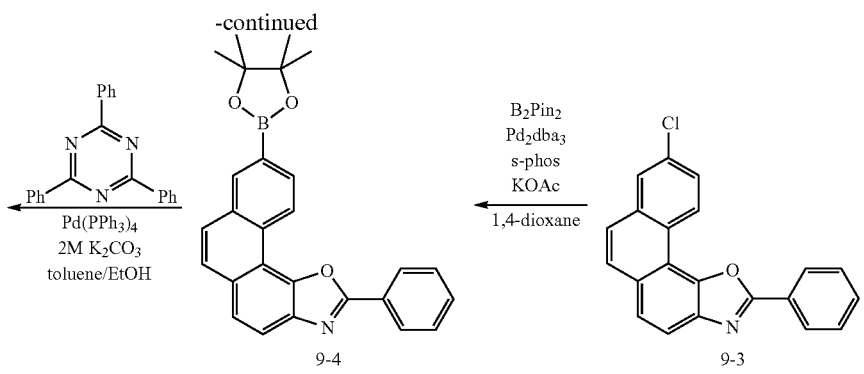

1) Preparation of Compound 9-1

After introducing compound 7-bromo-2-phenyl-benzoxazole (37 g, 135 mmol), 4-chloro-2-formylbenzene boronic acid (25 g, 135 mmol), tetrakis(triphenylphosphine)palladium (7.8 g, 6.7 mmol), sodium carbonate (35 g, 338 mmol), toluene (680 mL), ethanol (170 mL), and distilled water (170 mL) into a reaction vessel, the mixture was stirred for 3 hours at 130° C. After completing the reaction, the precipitated solid was washed with distilled water and methanol. The obtained compound was purified by column chromatography to obtain compound 9-1 (26 g, 60%).

2) Preparation of Compound 9-2

After introducing compound 9-1 (26 g, 80.2 mmol), (methoxymethyl)triphenylphosphonium chloride (41 g, 120 mmol), and tetrahydrofuran (800 mL) into a reaction vessel, the mixture was stirred for 5 minutes. Potassium tert-butoxide (1 M in THF, 120 mL) was then slowly added dropwise to the mixture at 0° C. The temperature of the mixture was slowly raised, and the mixture was stirred at room temperature for 3 hours. After completing the reaction by adding distilled water to the reaction solution, an organic layer was extracted with ethyl acetate. The extracted organic layer was dried with magnesium sulfate, and the solvent was removed therefrom using a rotary evaporator. Thereafter, the remaining product was purified by column chromatography to obtain compound 9-2 (25 g, 87%).

3) Preparation of Compound 9-3

After introducing compound 9-2 (25 g, 70.2 mmol), Eaton's reagent (3 mL), and chlorobenzene (350 mL) into a reaction vessel, the mixture was refluxed for 2 hours. After completing the reaction, the mixure was cooled to room temperature, and an organic layer was extracted with methylene chloride (MC). After drying the extracted organic layer with magnesium sulfate, the solvent was removed by using a rotary evaporator. Thereafter, the obtained product was purified by column chromatography to obtain compound 9-3 (13 g, 56%).

4) Preparation of Compound 9-4

After introducing compound 9-3 (13 g, 39 mmol), bis(pinacolato)dibororane (12 g, 47 mmol), tris(dibenzylidyneacetone)dipalladium (1.8 g, 1.9 mmol), 2-dicyclohexylphosphino-2',6'-dimethoxybiphenyl (s-phos) (1.6 g, 3.9 mmol), potassium acetate (11 g, 118 mmol), and 1,4-dioxane (330 mL) into a reaction vessel, the mixture was stirred for 4 hours at 130° C. After completing the reaction, the mixure was cooled to room temperature, and an organic layer was extracted with ethyl acetate. After drying the extracted organic layer with magnesium sulfate, the solvent was removed by using a rotary evaporator. Thereafter, the obtained product was purified by column chromatography to obtain compound 9-4 (13 g, 81%).

5) Preparation of Compound C-45

After introducing compound 9-4 (13 g, 31 mmol), 2-chloro-4,6-diphenyltriazine (8 g, 30 mmol), tetrakis(triphenylphosphine)palladium (1.7 g, 1.5 mmol), potassium carbonate (10 g, 75 mmol), toluene (140 mL), ethanol (35 mL), and distilled water (35 mL) into a reaction vessel, the mixture was stirred for 4 hours at 130° C. After completing the reaction, the precipitated solid was washed with distilled water and methanol. Thereafter, the obtained product was purified by column chromatography to obtain compound C-45 (7.7 g, 49%).

Example 10: Preparation of Compound C-100

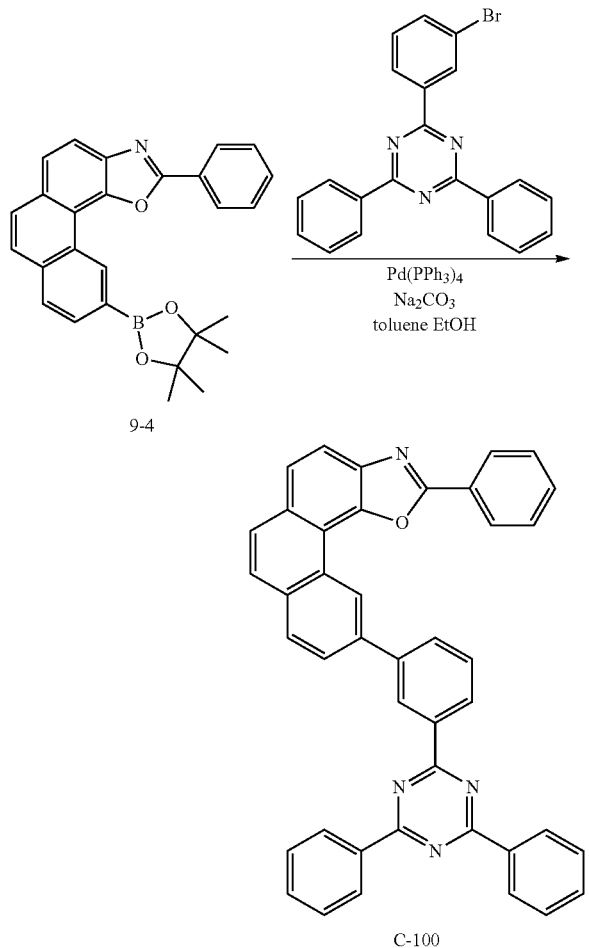

After introducing compound 9-4 (3 g, 7.1 mmol), 2-(3-bromophenyl)-4,6-diphenyl-1,3,5-triazine (CAS: 864377-31-1, 3.04 g, 7.8 mmol), tetrakis(triphenylphosphine)palladium (0.41 g, 0.36 mmol), sodium carbonate (1.9 g, 17.8 mmol), toluene (24 mL), ethanol (6 mL), and distilled water (6 mL) into a reaction vessel, the mixture was stirred for 4 hours at 120° C. After completing the reaction, the mixture was added dropwise to methanol, and the obtained solid was filtered. The obtained solid was purified by column chromatography and recrystallization to obtain compound C-100 (2.3 g, 54%).

Example 11: Preparation of Compound C-101

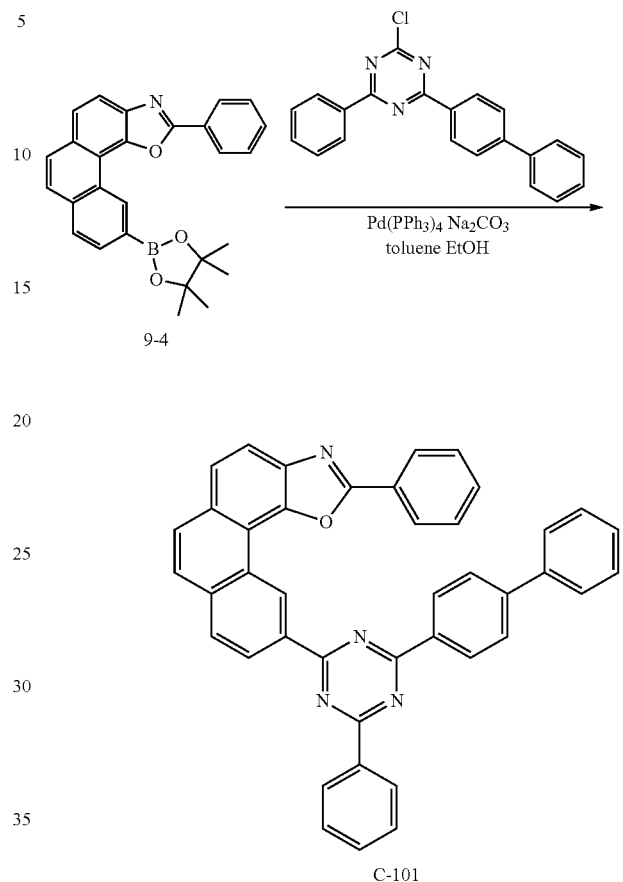

After introducing compound 9-4 (3.48 g, 8.3 mmol), 2-([1,1'-biphenyl]-4-yl)-4-chloro-6-phenyl-1,3,5-triazine (CAS: 1472062-94-4, 3.53 g, 9.1 mmol), tetrakis(triphenylphosphine)palladium (0.48 g, 0.41 mmol), sodium carbonate (2.2 g, 20.7 mmol), toluene (28 mL), ethanol (7 mL), and distilled water (7 mL) into a reaction vessel, the mixture was stirred for 5 hours at 120° C. After completing the reaction, the mixture was added dropwise to methanol, and the obtained solid was filtered. The obtained solid was purified by column chromatography and recrystallization to obtain compound C-101 (3.7 g, 74%).

The properties of the above synthesized compounds are shown in Table 1 below.

TABLE 1

| Compound | Yield (%) | UV Spectrum (in toluene, nm) | PL Spectrum (in toluene, nm) | MP (° C.) | MS/EIMS Measured Value | MS/EIMS Calculated Value |
|---|---|---|---|---|---|---|
| C-24 | 68 | 306 | 418 | 240 | 718.1 | 717.22 |
| C-1 | 55 | 306 | 426 | 276 | 543.2 | 542.16 |
| C-17 | 77 | 306 | 426 | 276 | 642.0 | 641.19 |
| C-39 | 47 | 304 | 400 | 230 | 702.1 | 701.25 |
| C-49 | 73 | 362 | 420 | 279 | 542.0 | 541.66 |
| C-75 | 82 | 260 | 392 | 300 | 526.1 | 525.18 |
| C-87 | 51 | 296 | 402 | 278 | 526.1 | 525.18 |
| C-88 | 50 | 290 | 427 | 291 | 527.1 | 526.18 |
| C-45 | 49 | 345 | 426 | 309 | 526.6 | 526.18 |

TABLE 1-continued

| Compound | Yield (%) | UV Spectrum (in toluene, nm) | PL Spectrum (in toluene, nm) | MP (° C.) | MS/EIMS Measured Value | MS/EIMS Calculated Value |
|---|---|---|---|---|---|---|
| C-100 | 54 | 358 | 401 | 298 | 602.7 | 602.21 |
| C-101 | 74 | 324 | 429 | 299 | 602.7 | 602.21 |

Hereinafter, the luminescent properties of the organic electroluminescent device comprising the organic electroluminescent compound of the present disclosure will be explained in detail with reference to the following examples.

Device Example 1: Preparation of an OLED Device Comprising the Organic Electroluminescent Compounds of the Present Disclosure as a Host An OLED device was produced by using the organic electroluminescent compound according to the present disclosure. A transparent electrode indium tin oxide (ITO) thin film (10 Ω/sq) on a glass substrate for an organic light-emitting diode (OLED) device (Geomatec) was subjected to an ultrasonic washing with acetone, ethanol, and distilled water, sequentially, and then was stored in isopropanol. The ITO substrate was then mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 80 nm on the ITO substrate. Next, compound HI-2 was introduced into another cell of said vacuum vapor depositing apparatus, and was evaporated by applying an electric current to the cell, thereby forming a second hole injection layer having a thickness of 5 nm on the first hole injection layer. Compound HT-1 was then introduced into the cell of said vacuum vapor depositing apparatus, and was evaporated by applying an electric current to the cell, thereby forming a first hole transport layer having a thickness of 10 nm on the second hole injection layer. Compound HT-3 was then introduced into another cell of said vacuum vapor depositing apparatus, and was evaporated by applying an electric current to the cell, thereby forming a second hole transport layer having a thickness of 60 nm on the first hole transport layer. After forming the hole injection layer and the hole transport layer, a light-emitting layer was formed thereon as follows: compound C-24 was introduced into one cell of said vacuum vapor depositing apparatus as a host, and compound D-71 was introduced into another cell as a dopant. The dopant was deposited in a doping amount of 3 wt % based on the total amount of the host and dopant to form a light-emitting layer having a thickness of 40 nm on the second hole transport layer. Compound ET-1 and compound EI-1 were then introduced into another two cells, and evaporated at a rate of 1:1 to form an electron transport layer having a thickness of 30 nm on the light-emitting layer. After depositing compound EI-1 as an electron injection layer having a thickness of 2 nm on the electron transport layer, an Al cathode having a thickness of 80 nm was deposited by another vacuum vapor deposition apparatus. Thus, an OLED device was produced.

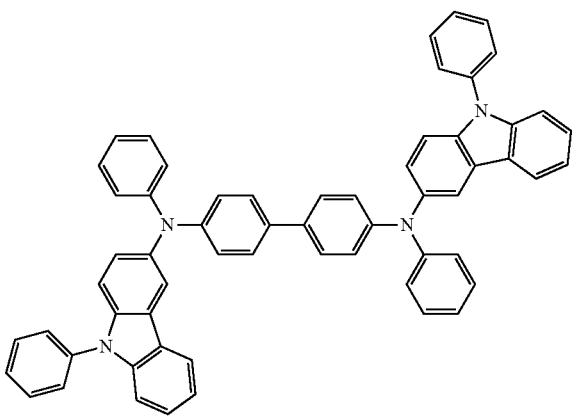

HI-1

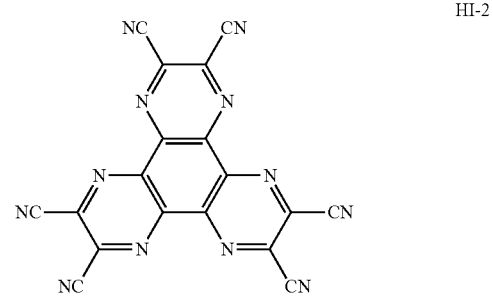

HI-2

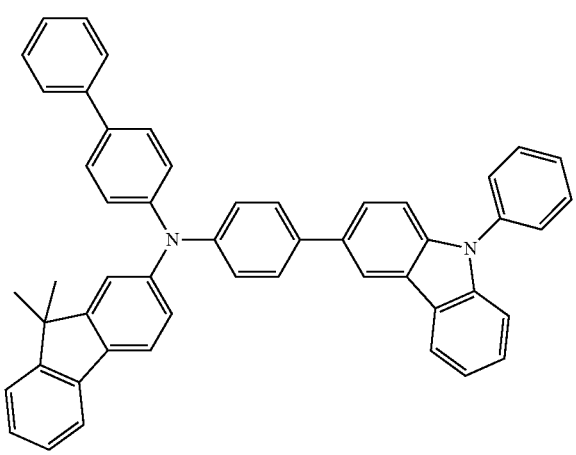

HT-1

HT-3

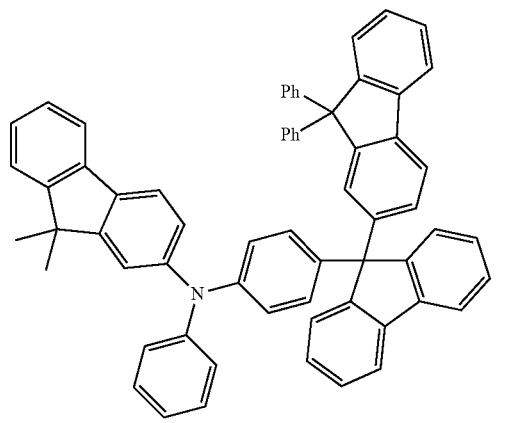

ET-1

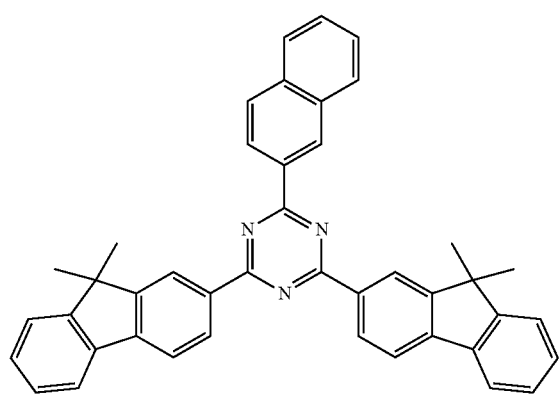

EI-1

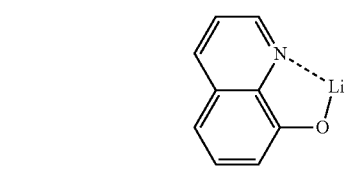

The produced OLED device showed a red emission having a luminance of 1,000 cd/m², and a luminous efficiency of 24.4 cd/A at 4.4 V. The time taken to be reduced to 90% of the luminance, where the early luminance is 100%, at 5,000 nits and a constant current was 43 hours or more.

Device Example 2: Preparation of an OLED Device Comprising the Organic Electroluminescent Compounds of the Present Disclosure as a Host An OLED device was produced in the same manner as in Device Example 1, except for using compound C-1 as a host of the light-emitting material. The produced OLED device showed a red emission having a luminance of 1,000 cd/m², and a luminous efficiency of 27.8 cd/A at 6.0 V. The time taken to be reduced to 90% of the luminance, where the early luminance is 100%, at 5,000 nits and a constant current was 37 hours or more.

Device Example 3: Preparation of an OLED Device Comprising the Organic Electroluminescent Compounds of the Present Disclosure as a Host An OLED device was produced in the same manner as in Device Example 1, except for using the compound C-39 as a host of the light-emitting material. The produced OLED device showed a red emission having a luminance of 1,000 cd/m², and a luminous efficiency of 22.9 cd/A at 4.5 V. The time taken to be reduced to 90% of the luminance, where the early luminance is 100%, at 5,000 nits and a constant current was 38 hours or more.

Comparative Device Example 1: Preparation of an OLED Device Comprising Conventional Organic Electroluminescent Compounds An OLED device was produced in the same manner as in Device Example 1, except for using the following compound K as a host of the light-emitting material.

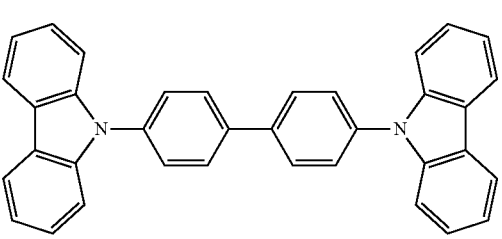

K

The produced OLED device showed a red emission having a luminance of 1,000 cd/m², and a luminous efficiency of 14.3 cd/A at 10.0 V. The time taken to be reduced to 90% of the luminance, where the early luminance is 100%, at 5,000 nits and a constant current was less than 1 hour.

The invention claimed is:
1. An organic electroluminescent compound represented by the following formula 3:

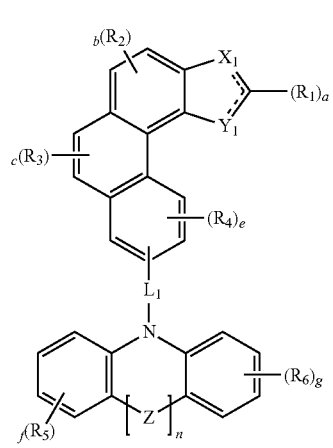

(3)

wherein
$X_1$ represents —N=, —$NR_7$—, —O—, or —S—;
$Y_1$ represents —N=, —$NR_8$—, —O—, or —S—;
with the provisos that when $X_1$ represents —N=, then $Y_1$ represents —O—, or —S—, and when $X_1$ represents —$NR_7$—, then $Y_1$ represents —O—, or —S—, with the provisos that $X_1$ and $Y_1$ are not simultaneously —O—; $X_1$ and $Y_1$ are not simultaneously —S—; $X_1$ and $Y_1$ are not —O— and —S—, respectively; and $X_1$ and $Y_1$ are not —S— and —O—, respectively;

R₁ represents a substituted or unsubstituted (C6-C30)aryl, or a substituted or unsubstituted (3- to 30-membered) heteroaryl;

R₂ represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30) alkylsilyl, a substituted or unsubstituted di(C1-C30)alkyl(C6-C30)arylsilyl, a substituted or unsubstituted (C1-C30)alkyldi(C6-C30)arylsilyl, or a substituted or unsubstituted tri(C6-C30) arylsilyl;

R₃, R₄, R₇ and R₈, each independently, represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di- (C1-C30)alkylamino, a substituted or unsubstituted mono- or di- (C6-C30)arylamino, or a substituted or unsubstituted (C1-C30)alkyl(C6-C30)arylamino; or are linked to an adjacent substituent(s) to form a substituted or unsubstituted, mono- or polycyclic, (C3-C30) alicyclic or aromatic ring, whose carbon atom(s) may be replaced with at least one heteroatom selected from nitrogen, oxygen, and sulfur;

a represents 1; b and c, each independently, represent 1 or 2; d represents an integer of 1 to 4;

L₁ represents a single bond, a substituted or unsubstituted (C6-C30)arylene, or a substituted or unsubstituted (3- to 30-membered)heteroarylene;

Z represents a single bond, or a substituted or unsubstituted (C1-C6)alkylene;

R₅ and R₆, each independently, have the same definition as R₃ to R₄;

n represents 0 or 1; e represents an integer of 1 to 3; f and g, each independently, represent an integer of 1 to 4; and the heteroaryl contains at least one heteroatom selected from B, N, O, S, Si, and P.

2. The organic electroluminescent compound according to claim 1, wherein the compound represented by formula 3 is selected from the group consisting of:

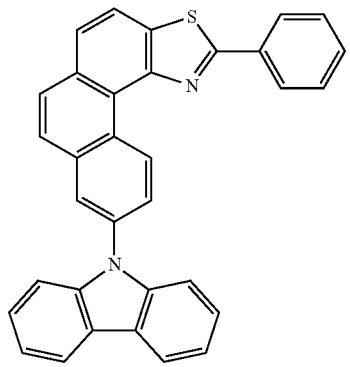

C-13

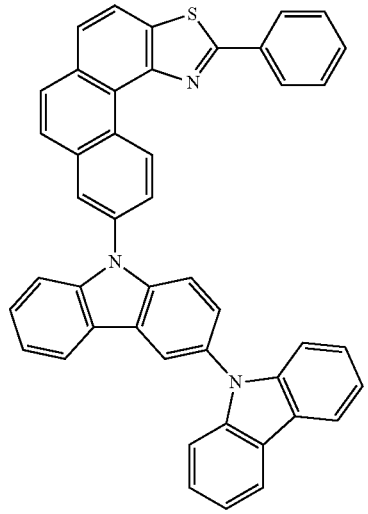

C-14

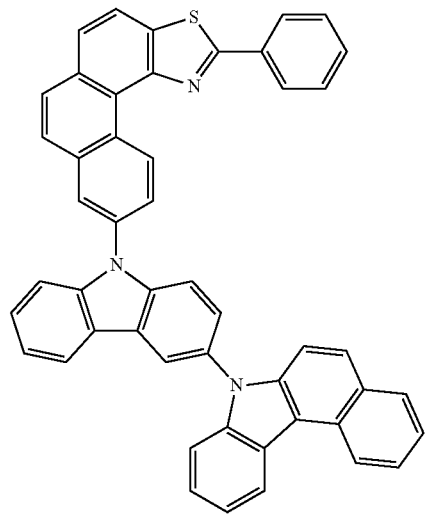

C-15

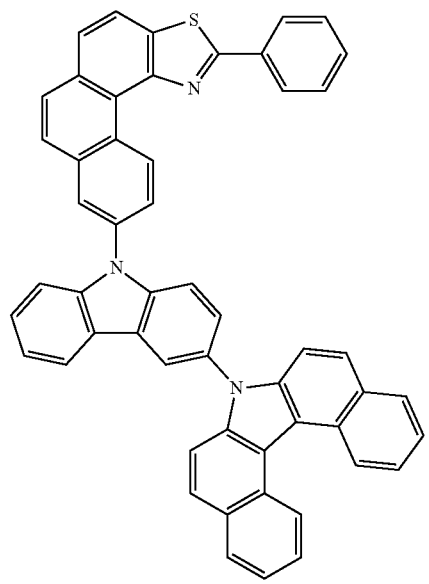

C-16

-continued
C-17
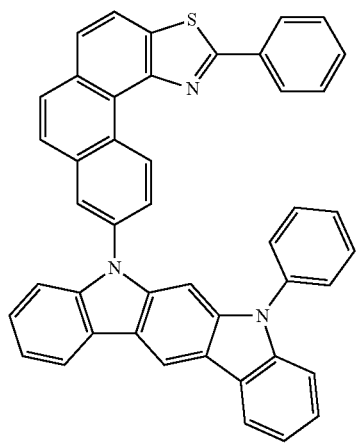
C-18
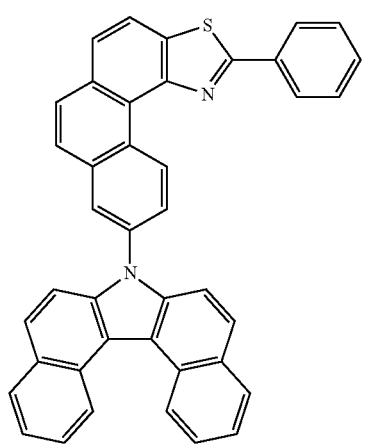
C-19
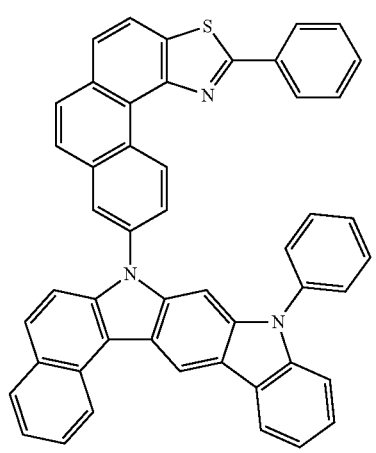
-continued
C-20
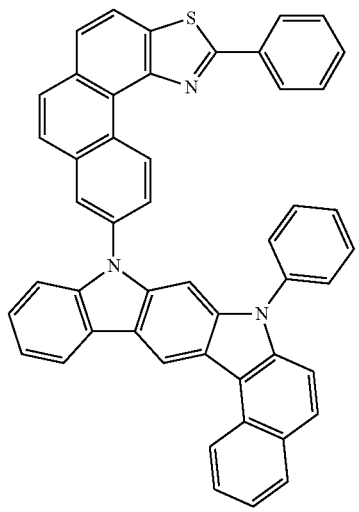
C-21
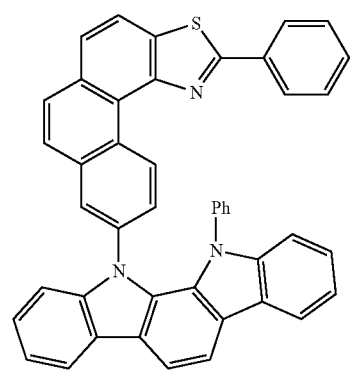
C-22
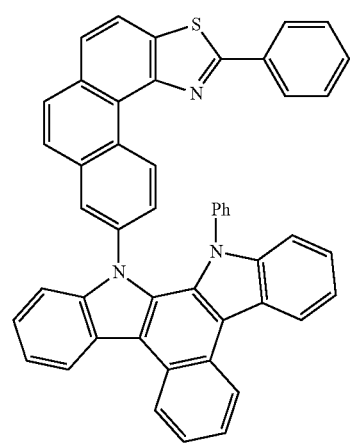

C-23
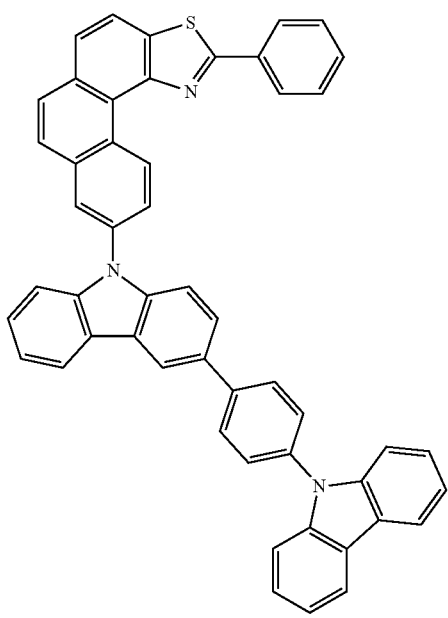
C-24
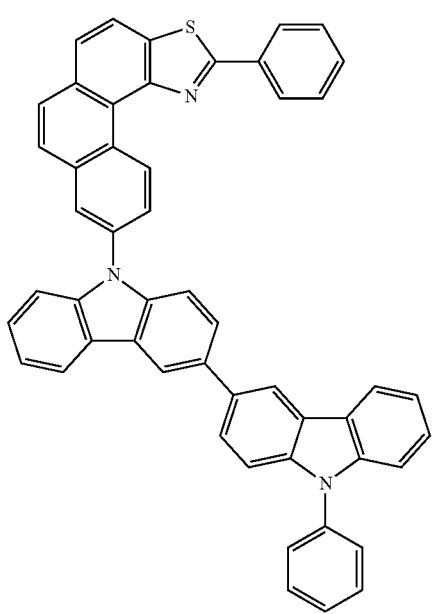
C-25
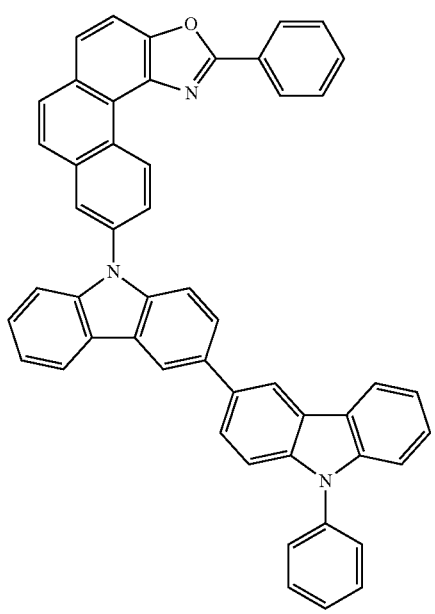
C-26
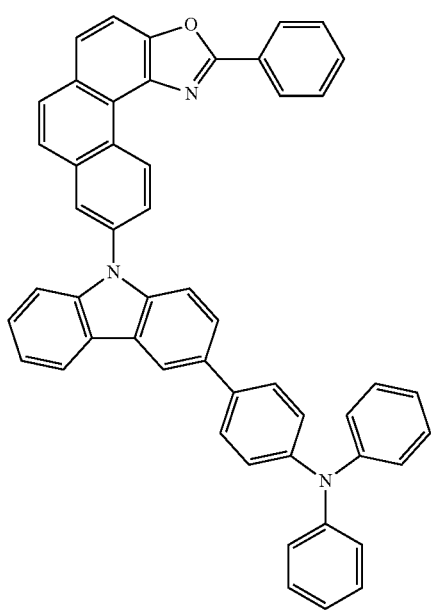

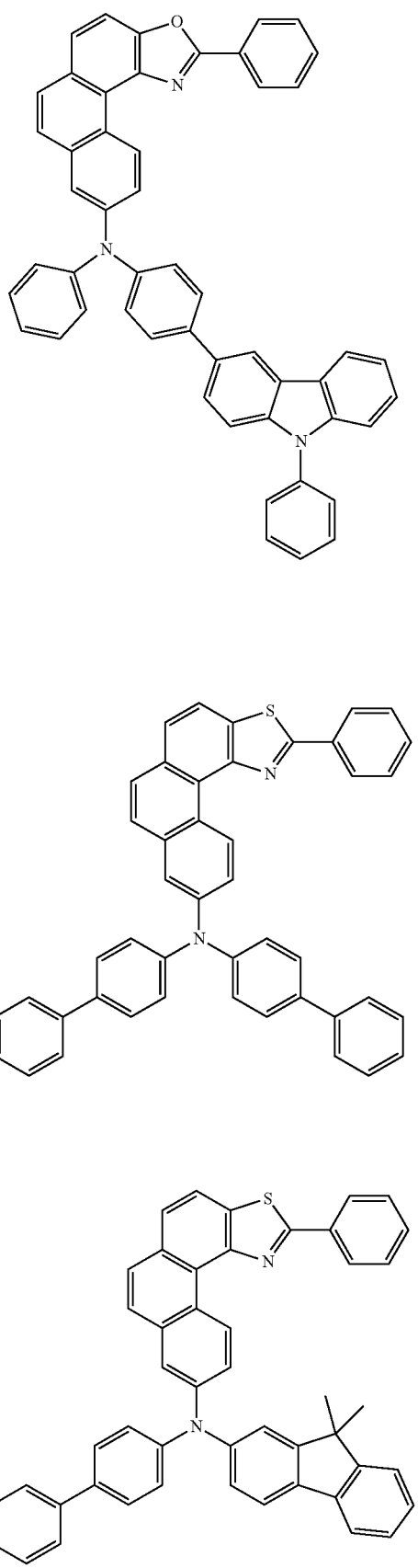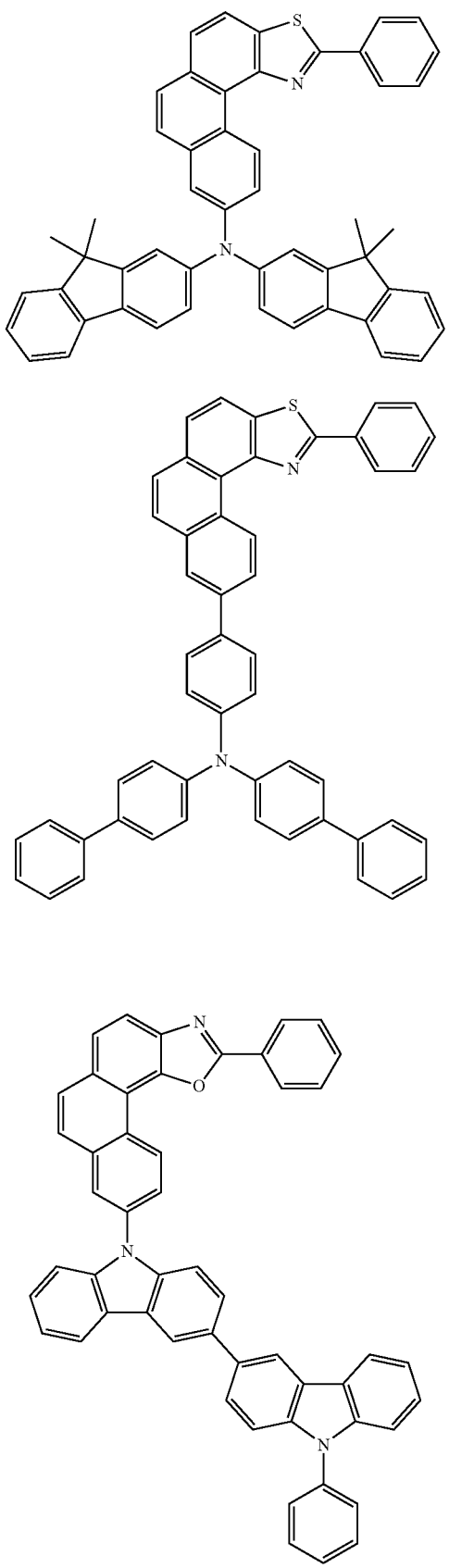

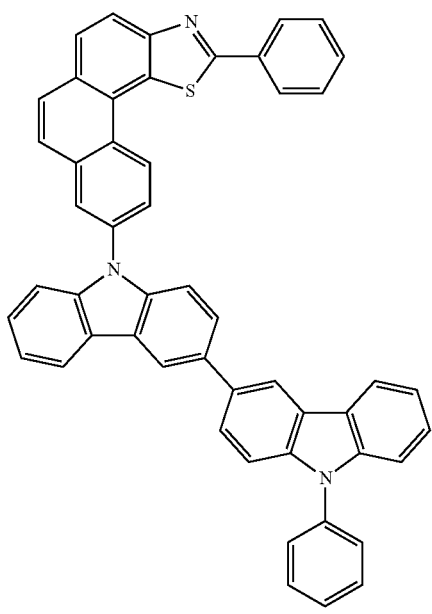
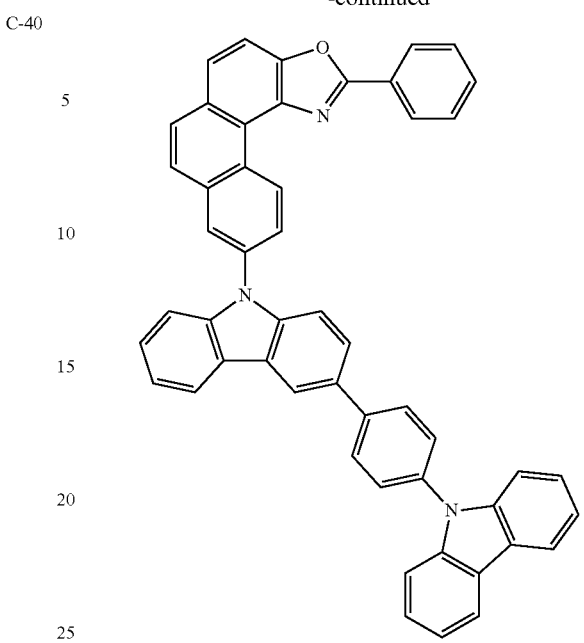

-continued
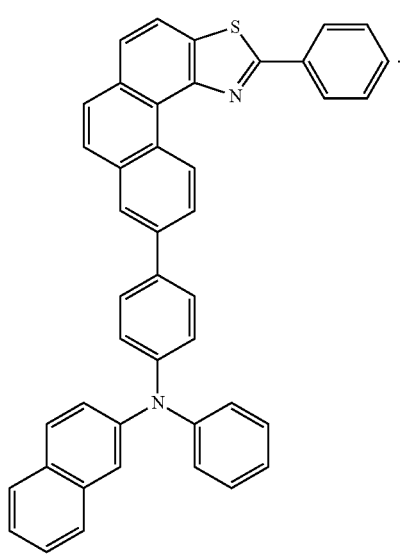
C-54
3. An organic electroluminescent device comprising the organic electroluminescent compound according to claim 1 as a host material.
* * * * *